US007927608B2

(12) United States Patent
Harel et al.

(10) Patent No.: US 7,927,608 B2
(45) Date of Patent: Apr. 19, 2011

(54) ***STREPTOCOCCUS SUIS* POLYPEPTIDES AND POLYNUCLEOTIDES ENCODING SAME AND THEIR USE IN VACCINAL AND DIAGNOSTIC APPLICATIONS**

(75) Inventors: Josée Harel, St-Bruno (CA); Marcelo Gottschalk, St-Hyacinthe (CA); Yuanyi Li, St-Basile-le-Grand (CA)

(73) Assignee: Valorisation—Recherche Limited Partnership, Montreal, Quebec ( * ) Notice: Subject to any disclaimer, the term of this patent is extended or adjusted under 35 U.S.C. 154(b) by 283 days.

(21) Appl. No.: 12/065,592

(22) PCT Filed: Sep. 1, 2006

(86) PCT No.: PCT/CA2006/001454
§ 371 (c)(1),
(2), (4) Date: Mar. 3, 2008

(87) PCT Pub. No.: WO2007/025390
PCT Pub. Date: Mar. 8, 2007

(65) Prior Publication Data
US 2009/0220513 A1    Sep. 3, 2009

Related U.S. Application Data

(60) Provisional application No. 60/713,328, filed on Sep. 2, 2005.

(51) Int. Cl.
*A61K 39/09* (2006.01)
(52) U.S. Cl. ............... 424/244.1; 424/185.1; 424/190.1; 424/193.1; 530/350
(58) Field of Classification Search .................. None
See application file for complete search history.

(56) References Cited

U.S. PATENT DOCUMENTS
5,610,011 A    3/1997    Smith et al.

OTHER PUBLICATIONS

Greenspan et al (Nature Biotechnology 7: 936-937, 1999).*
Chothia et al (The EMBO Journal, 1986, 5/4:823-26).*
Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Arends, J. P., and H. C. Zanen. 1988. Meningitis caused by *Streptococcus suis* in humans. Rev Infect Dis 10:131-7.
Arulanandam, B. P., J. M. Lynch, D. E. Briles, S. Hollingshead, and D. W. Metzger. 2001. Intranasal vaccination with pneumococcal surface protein A and interleukin-12 augments antibody-mediated opsonization and protective immunity against *Streptococcus pneumoniae* infection. Infect Immun 69:6718-24.
Berthelot-Herault, F., R. Cariolet, A. Labbe, M. Gottschalk, J. Y. Cardinal, and M. Kobisch. 2001. Experimental infection of specific pathogen free piglets with French strains of *Streptococcus suis* capsular type 2. Can J Vet Res 65:196-200.
Buchanan, R. M., D. E. Briles, B. P. Arulanandam, M. A. Westerink, R. H. Raeder, and D. W. Metzger. 2001. IL-12—mediated increases in protection elicited by pneumococcal and meningococcal conjugate vaccines. Vaccine 19:2020-8.
Burnette, W. N. 1981. "Western blotting": electrophoretic transfer of proteins from sodium dodecyl sulfate—polyacrylamide gels to unmodified nitrocellulose and radiographic detection with antibody and radioiodinated protein A. Anal Biochem 112:195-203.
Crawley, A., and B. N. Wilkie. 2003. Porcine Ig isotypes: function and molecular characteristics. Vaccine 21:2911-22.
Elliott, S. D., F. Clifton-Hadley, and J. Tai. 1980. Streptococcal infection in young pigs. V. An immunogenic polysaccharide from *Streptococcus suis* type 2 with particular reference to vaccination against Streptococcal meningitis in pigs. J Hyg (Lond) 85:275-85.
Galina, L., U. Vecht, H. J. Wisselink, and C. Pijoan. 1996. Prevalence of various phenotypes of *Streptococcus suis* isolated from swine in the U.S.A. based on the presence of muraminidase-released protein and extracellular factor. Can J Vet Res 60:72-4.
Gottschalk, M., R. Higgins, M. Jacques, M. Beaudoin, and J. Henrichsen. 1991. Characterization of six new capsular types (23 through 28) of *Streptococcus suis*. J Clin Microbiol 29:2590-4.
Gottschalk, M., R. Higgins, M. Jacques, M. Beaudoin, and J. Henrichsen. 1991. Isolation and characterization of *Streptococcus suis* capsular types 9-22. J Vet Diagn Invest 3:60-5.
Gottschalk, M., R. Higgins, M. Jacques, K. R. Mittal, and J. Henrichsen. 1989. Description of 14 new capsular types of *Streptococcus suis* . J Clin Microbiol 27:2633-6.
Gottschalk, M., A. Lebrun, H. Wisselink, J. D. Dubreuil, H. Smith, and U. Vecht. 1998. Production of virulence-related proteins by Canadian strains of *Streptococcus suis* capsular type 2. Can J Vet Res 62:75-9.
Gottschalk, M., and M. Segura. 2000. The pathogenesis of the meningitis caused by *Streptococcus suis*: the unresolved questions. Vet Microbiol 76:259-72.
Higgins, R., and M. Gottschalk. 1998. Distribution of *Streptococcus suis* capsular types in 1997. Can Vet J 39:299-300.
Higgins, R., M. Gottschalk, M. Boudreau, A. Lebrun, and J. Henrichsen. 1995. Description of six new capsular types (29-34) of *Streptococcus suis*. J Vet Diagn Invest 7:405-6.
Higgins, R., M. Gottschalk. 2005. Streptococcal diseases (In press). In B. E. Straw, S. D'Allaire, W. L. Mengeling, and D. J. Taylor (9th ed), Diseases of swine. Iowa State University Press, Ames.
Hill, J. E., M. Gottschalk, R. Brousseau, J. Harel, S. M. Hemmingsen, and S. H. Goh. 2005. Biochemical analysis, cpn60 and 16S rDNA sequence data indicate that *Streptococcus suis* serotypes 32 and 34, isolated from pigs, are *Streptococcus orisratti*. Vet Microbiol 107:63-9.

(Continued)

*Primary Examiner* — Jennifer E Graser
(74) *Attorney, Agent, or Firm* — Choate Hall & Stewart LLP; Charles E. Lyon

(57) ABSTRACT

The present invention relates to the field of *Streptococcus*. More specifically, the present invention relates to the identification of polypeptides and polynucleotide sequences encoding the same which are involved in the pathogenic mechanism of *S. suis*. The present invention also relates to the use of such polypeptides in compositions and methods for the prevention, the treatment and diagnosis of *S. suis*-associated diseases and infections caused by *S. suis*.

20 Claims, 25 Drawing Sheets

OTHER PUBLICATIONS

Holt, M. E., M. R. Enright, and T. J. Alexander. 1988. Immunisation of pigs with live cultures of *Streptococcus suis* type 2. Res Vet Sci 45:349-52.

Ioannou, X. P., P. Griebel, R. Hecker, L. A. Babiuk, and S. van Drunen Littel-13 van den Hurk. 2002. The immunogenicity and protective efficacy of bovine herpesvirus 1 glycoprotein D plus Emulsigen are increased by formulation with CpG oligodeoxynucleotides. J Virol 76:9002-10.

Jacobs, A. A., A. J. van den Berg, and P. L. Loeffen. 1996. Protection of experimentally infected pigs by suilysin, the thiol-activated haemolysin of *Streptococcus suis*. Vet Rec 139:225-8.

Laemmli, U. K. 1970. Cleavage of structural proteins during the assembly of the head of bacteriophage T4. Nature 227:680-5.

Lefeber, D. J., B. Benaissa-Trouw, J. F. Vliegenthart, J. P. Kamerling, W. T. Jansen, K. Kraaijeveld, and H. Snippe. 2003. Th1-directing adjuvants increase the immunogenicity of oligosaccharide-protein conjugate vaccines related to *Streptococcus pneumoniae* type 3. Infect Immun 71:6915-20.

Lofthouse, S. A., A. E. Andrews, A. D. Nash, and V. M. Bowles. 1995. Humoral and cellular responses induced by intradermally administered cytokine and conventional adjuvants. Vaccine 13:1131-7.

Lynch, J. M., D. E. Briles, and D. W. Metzger. 2003. Increased protection against pneumococcal disease by mucosal administration of conjugate vaccine plus interleukin-12, Infect Immun 71:4780-8.

Marques, M. B., D. L. Kasper, A. Shroff, F. Michon, H. J. Jennings, and M. R. Wessels. 1994. Functional activity of antibodies to the group B polysaccharide of group B streptococci elicited by a polysaccharide-protein conjugate vaccine. Infect Immun 62:1593-9.

McArthur, J., E. Medina, A. Mueller, J. Chin, B. J. Currie, K. S. Sriprakash, S. R. Talay, G. S. Chhatwal, and M. J. Walker. 2004. Intranasal vaccination with streptococcal fibronectin binding protein Sfb1 fails to prevent growth and dissemination of *Streptococcus pyogenes* in a murine skin Infection model. Infect Immun 72:7342-5.

Miyaji, E. N., D. M. Ferreira, A. P. Lopes, M. C. Brandileone, W. O. Dias, and L. C. Leite. 2002. Analysis of serum cross-reactivity and cross-protection elicited by immunization with DNA vaccines against *Streptococcus pneumoniae* expressing PspA fragments from different clades. Infect Immun 70:5086-90.

Nichani, A. K., R. S. Kaushik, A. Mena, Y. Popowych, D. Dent, H. G. Townsend, G. Mutwiri, R. Hecker, L. A. Babiuk, and P. J. Griebel. 2004. CpG oligodeoxynucleotide induction of antiviral effector molecules in sheep. Cell immunol 227:24-37.

Okwumabua, O., O. Abdelmagid, and M. M. Chengappa. 1999. Hybridization analysis of the gene encoding a hemolysin (suilysin) of *Streptococcus suis* type 2: evidence for the absence of the gene in some isolates. FEMS Microbiol Lett 181:113-21.

Pallares, F. J., C. S. Schmitt, J. A. Roth, R. B. Evans, J. M. Kinyon, and P. G. Halbur. 2004. Evaluation of a ceftiofur-washed whole cell *Streptococcus suis* bacterin in pigs. Can J Vet Res 68:236-40.

Perch, B., K. B. Pedersen, and J. Henrichsen. 1983. Serology of capsulated streptococci pathogenic for pigs: six new serotypes of *Streptococcus suis*. J Clin Microbiol 17:993-6.

Segura, M., M. Gottschalk, and M. Olivier. 2004. Encapsulated *Streptococcus suis* inhibits activation of signaling pathways involved in phagocytosis. Infect Immun 72:5322-30.

Serhir, B., D. Dugourd, M. Jacques, R. Higgins, and J. Harel. 1997. Cloning and characterization of a dextranase gene (dexS) from *Streptococcus suis*. Gene 190:257-61.

Sheoran, A. S., S. Artiushin, and J. F. Timoney. 2002. Nasal mucosal Immunogenicity for the horse of a SeM peptide of *Streptococcus equi* genetically coupled to cholera toxin. Vaccine 20:1653-9.

Torremorell, M., C. Pijoan, and S. Dee. 1999. Experimental exposure of young pigs using a pathogenic strain of *Streptococcus suis* serotype 2 and evaluation of this method for disease prevention. Can J Vet Res 63:269-75.

Trottier, S., R. Higgins, G. Brochu, and M. Gottschalk. 1991. A case of human endocarditls due to *Streptococcus suis* in North America. Rev Infect Dis 13:1251-2.

Willson, P. J., A. Rossi-Campos, and A. A. Potter. 1995. Tissue reaction and immunity in swine immunized with *Actinobacillus pleuropneumoniae* vaccines. Can J Vet Res 59:299-305.

Wisselink, H. J., N. Stockhofe-Zurwieden, L. A. Hilgers, and H. E. Smith. 2002. Assessment of protective efficacy of live and killed vaccines based on a non-encapsulated mutant of *Streptococcus suis* serotype 2. Vet Microbiol 84:155-68.

Wisselink, H. J., U. Vecht, N. Stockhofe-Zurwleden, and H. E. Smith. 2001. Protection of pigs against challenge with virulent *Streptococcus suis* serotype 2 strains by a muramidase-released protein and extracellular factor vaccine. Vet Rec 148:473-7.

Wortham, C., L. Grinberg, D. C. Kaslow, D. E. Briles, L. S. McDaniel, A. Lees, M. Flora, C. M. Snapper, and J. J. Mond. 1998. Enhanced protective antibody responses to PspA after intranasal or subcutaneous injections of PspA genetically fused to granulocyte-macrophage colony-stimulating factor or interleukin-2. Infect Immun 66:1513-20.

Yang, B., W. Zhu, L. B. Johnson, and F. F. White. 2000. The virulence factor AvrXa7 of *Xanthomonas oryzae* pv. *oryzae* is a type III secretion pathway-dependent nuclear-localized double-stranded DNA-binding protein. Proc Natl Acad Sci U S A 97:9807-12.

Pollack, M., N. L. Koles, M. J. Preston, B. J. Brown, and G. B. Pier. 1995. Functional properties of isotype-switched immunoglobulin M (IgM) and IgG monoclonal antibodies to *Pseudomonas aeruginosa* lipopolysaccharide. Infect Immun 63:4481-8.

Unkeless, J. C., E. Scigliano, and V. H. Freedman. 1988. Structure and function of human and murine receptors for IgG. Annu Rev Immunol 6:251-81.

Li, Y et al., Identification of a surface protein of *Streptococcus suis* and evaluation of its immunogenic and protective capacity in pigs. Infect Immun. Jan. 2006, vol. 74, No. 1, pp. 305-312, ISSN 0019-9567.

Copeland, A. et al., GenBank Accession No. ZP 00874910. Surface proteins from gram-positive cocci, anchor region [*Streptococcus suis* 89/1591], 2005.

* cited by examiner

Figure 2

```
Ctttgagaaaggaaaaaaggata ATGAATACTAAGAAATGGAGAACATCGCTCCTAATACCAGGAATAGTATTATTTGGAACTGTTGCT    90
                        M  N  T  K  K  W  R  T  S  L  L  I  P  G  I  V  L  F  G  T  V  A     22

CTAGTGAATAATGTATCGGCACAAGAAGTAAAAAATACCATCATCAGCGCAAAACAACCTGATGGGGACAGGCTACTTCAAAGGCGTT    180
 L  V  N  N  V  S  A  Q  E  V  K  N  T  I  I  S  A  K  Q  P  D  G  G  Q  A  T  S  K  A  V     52

AATGTCAAAATACCAGCAGTAGTACGACTATTTGGTCGTGAGCTTCTAGAAAATGAATTTAAATTTGAGCTTAGAGAAGCGAATGGCGAG    270
 N  V  K  I  P  A  V  V  R  L  F  G  R  E  L  L  E  N  E  F  K  F  E  L  R  E  A  N  G  E     82

GAACTCCCTGTCCTTGATACAGCTCAAAATACAAAAGAGGGTCAAGTTAGATTTAAAAATCTATCATTCGATAAGCCTGGCAAATACTGG    360
 E  L  P  V  L  D  T  A  Q  N  T  K  E  G  Q  V  R  F  K  N  L  S  F  D  K  P  G  K  Y  W    112

TATACAATTTCAGAAGTAAAAGATGAGCTTGGTGGTATTGAGTATGATTCGAAATATATTGTAGCAAAAATAACTGTAGAAGATCGAAAC    450
 Y  T  I  S  E  V  K  D  E  L  G  G  I  E  Y  D  S  K  Y  I  V  A  K  I  T  V  E  D  R  N    142

GGGCAATTACAGGCAATGATCGAATTTATTGATAATGACAATGTCTTTAACAATTTCTATACACCTGCTCCAGCTGCTGCTAGTCTTTCG    540
 G  Q  L  Q  A  M  I  E  F  I  D  N  D  N  V  F  N  N  F  Y  T  P  A  P  A  A  A  S  L  S    172

ATAAAAAAAGTCCTCGAGGGACGTACCTTAAACACCGGTGAATTCGAATTTGTTTTAAAAAATGAAAAGGCGATGAAATCGAAAGGTA    630
 I  K  K  V  L  E  G  R  T  L  N  T  G  E  F  E  F  V  L  K  N  E  K  G  D  E  I  E  K  V    202

AGCAATCAAGCAGATGGTTCTGTAAACTTTAGTGCCCTAACATTTACAAAAGAGGGAACCTATACCTACACTGTTTCAGAAGTTGATGGT    720
 S  N  Q  A  D  G  S  V  N  F  S  A  L  T  F  T  K  E  G  T  Y  T  Y  T  V  S  E  V  D  G    232

GGACTTGGCGATATTATCTATGACAAATCAGATATTAAGGCCACTGTTACTGTGAAAGATAACAATCACGGACAACTAGTCTCAACAGTG    810
 G  L  G  D  I  I  Y  D  K  S  D  I  K  A  T  V  T  V  K  D  N  N  H  G  Q  L  V  S  T  V    262

ACTTATGAAAATAGCGATCAAATCTTCGAGAATATTTTGAATCCTGGGAAGTTAATAGCGCCAACCACGGATAGCGTTATTACTGATAAT    900
 T  Y  E  N  S  D  Q  I  F  E  N  I  L  N  P  G  K  L  I  A  P  T  T  D  S  V  I  T  D  N    292

GAAGTCTCTAAGGAAGCAATGACCGGTAAAGAGAAGGGAAATATCGAACCCCCTGAAAAGCAAATGACTAATAAAGAGAAGGATAATATT    990
 E  V  S  K  E  A  M  T  G  K  E  K  G  N  I  E  P  P  E  K  Q  M  T  N  K  E  K  D  N  I    322
       └──▶R1

GAAACCCTCTGAAAAACAGATGCCGAGTGTTGTGAACGAAAATGCCGTAACACCTGAAAAGCAAATGACTAATAAAGAGAACGATAAGGTT   1080
 E  T  S  E  K  Q  M  P  S  V  V  N  E  N  A  V  T  P  E  K  Q  M  T  N  K  E  N  D  K  V    352
    └──▶R2

GTAATCTCTGAAAAACAAATGCCGAGTGTTGTGAACGAAAATGCCGTAACACCTGAAAAGCAAATGACTAATAAAGAGAACGATAATATT   1170
 V  I  S  E  K  Q  M  P  S  V  V  N  E  N  A  V  T  P  E  K  Q  M  T  N  K  E  N  D  N  I    382
    └──▶R3

GAAACCTCTGAAAAACAGATGCCGAGTGTTGTGAACGAAAATGCCGTAACACCTGAAAAGCAAATGACTAATAAAGAGAAGGATAATATT   1260
 E  T  S  E  K  Q  M  P  S  V  V  N  E  N  A  V  T  P  E  K  Q  M  T  N  K  E  K  D  N  I    412
    └──▶R4

GAAACCTCTGAAAAACAGATGCCGAGTGTTGTGAACGAAAATGCCGTAACACCTGAAAAGCAAATGACTAATAAAGAGAAGGATAATATT   1350
 E  T  S  E  K  Q  M  P  S  V  V  N  E  N  A  V  T  P  E  K  Q  M  T  N  K  E  K  D  N  I    442
    └──▶R5

GAAACCTCTGAAAAACAAATGCCAAGCATTGTGAACGACATGGTCGTAACACCTCAAGAGCAAATGGCTAATAAAGAGAACGATAAGGTT   1440
 E  T  S  E  K  Q  M  P  S  I  V  N  D  M  V  V  T  P  Q  E  Q  M  A  N  K  E  N  D  K  V    472
    └──▶R6

GTAATCTCTGAAAAACAGATGCCAAGCATTGTGAACGACATGGTCGTAACACCTCAAGAACAAATGGCTAATAAAGAGAACGATAAGGTT   1530
 V  I  S  E  K  Q  M  P  S  I  V  N  D  M  V  V  T  P  Q  E  Q  M  A  N  K  E  N  D  K  V    502
    └──▶R7

GTAATCTCTGAAAAACAGATGCCAAGCATTGTGAACGACATGGTCGTAACACCTCAAGAACAAATGGCTAATAAAGAGAACGATAAGGTT   1620
 V  I  S  E  K  Q  M  P  S  I  V  N  D  M  V  V  T  P  Q  E  Q  M  A  N  K  E  N  D  K  V    532
    └──▶R8

GTAATCTCTGAAAAACAGATGCCAAGCATTGTGAACGACATGGTCGTAACACCTCAAGAACAAATGGCTAATAAAGAGAACGATAAGGTT   1710
 V  I  S  E  K  Q  M  P  S  I  V  N  D  M  V  V  T  P  Q  E  Q  M  A  N  K  E  N  D  K  V    562
    └──▶R9

GAAACCTCTGAAAAACAGATGCCTGTTAATGAGAAGGACAATGCCGTAACACCTGAAAAGCAAATGGCTAATAAAGAGAAGGAAAATATC   1800
 E  T  S  E  K  Q  M  P  V  N  E  K  D  N  A  V  T  P  E  K  Q  M  A  N  K  E  K  E  N  I    592
    └──▶R10

GAAACCCTCTAAAAAACAGATACCTGTTAATGAGAACAACCAAAATGGTACAGTCGAAGAAAATTCAAACACTAAACCAACAACTGAAAAA   1890
 E  T  S  K  K  Q  I  P  V  N  E  N  N  Q  N  G  T  V  E  E  N  S  N  T  K  P  T  T  E  K    622

ACAGACAAGCAGGAGACTTCAACATTTAAAACCGAAACTGCTAAGCAAATCTTACCAGTAACTGGTGAGAAAGGAAGTTTATGGTTATTG   1980
 T  D  K  Q  E  T  S  T  F  K  T  E  T  A  K  Q  I  L  P  V  T  G  E  K  G  S  L  W  L  L    652

ACAAGTGGTATTATCGGGCTTGCAATTGCGTTATTTACACGTAAACGTAAATTATAA                                    2037
 T  S  G  I  I  G  L  A  I  A  L  F  T  R  K  R  K  L  *                                     670
                                  + + +  +
```

Figure 3

```
 52  kqaletvqrllpvlcqahgltpeqvvaiashdggkqaletvqrllpvlcq       Avr/PthA
     |..:||.::.:|.:....::|||:.:....:|  |...:.  ::..:|.:..
319  KDNIETSEKQMPSVVNENAVTPEKQMTNKEND--KVVIS--EKQMPSVVN        SP1/Lys319-Val601

102  ahgltpdqvvaiashdggkqaletvqrllpvlcqahgltpeqvvaiasni        Avr/PthA
     .:.:||::.:.....:|.    :||.::.:|.:.....:|||:.:....
365  ENAVTPEKQMTNKENDN----IETSEKQMPSVVNENAVTPEKQMTNKE--        SP1/Lys319-Val601

152  ggkqaletvqrllpvlcqahgltpdqvvaiashdggkqaletvqrllpvl        Avr/PthA
     |...:||.::.:|.:....::|||::.:......|.   :||.::..:|.:
409  --KDNIETSEKQMPSVVNENAVTPEKQMTNKEKDN----IETSEKQMPSI        SP1/Lys319-Val601

202  cqahgltpeqvvaiasn----iggkqaletvqrllpvlcqahgltpqqvv        Avr/PthA
     .....:||::.:|...|   |..||        :|.:......:|||:.:
453  VNDMVVTPQEQMANKENDKVVISEKQ--------MPSIVNDMVVTPQEQM        SP1/Lys319-Val601

248  aiasngggkqaletvqrllpvlceqhgltpdqvvaiasn----iggkqal        Avr/PthA
     |...|   ..:....::..:|.:......:||.:.:|...|   |..||
495  ANKEN----DKVVISEKQMPSIVNDMVVTPQEQMANKENDKVVISEKQ--        SP1/Lys319-Val601

296  etvqrllpvlceqhgltpeqvvaiasnnggkqaletvqrllpvlcqahgl        Avr/PthA
     :|.:......:||::.:|...|:    .:||.:::.:||..:.:..:
539  ------MPSIVNDMVVTPQEQMANKEND----KVETSEKQMPVNEKDNAV        SP1/Lys319-Val601

346  tpdqvvaiashdggkqaletvqrllpv      373   Avr/PthA
     ||::.:|    :..|.:||.::.:||
579  TPEKQMA----NKEKENIETSKKQIPV      601   SP1/Lys319-Val601
```

Figure 4
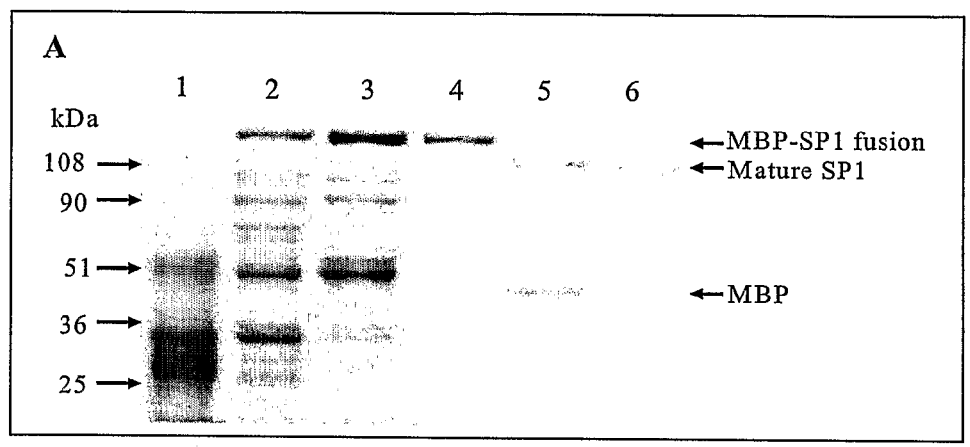
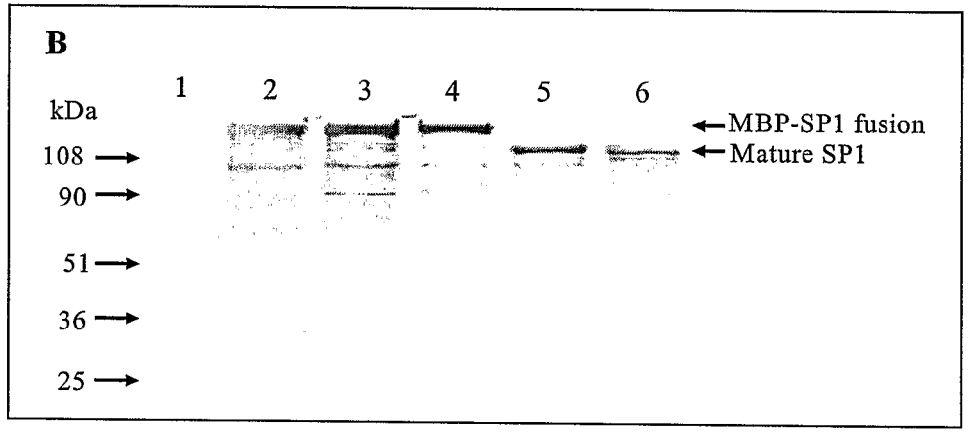

A B

```
tcggcacaagaagtaaaaaataccatcatcagcgcaaaacaacctgatgggggacaggct
 S   A   Q   E   V   K   N   T   I   I   S   A   K   Q   P   D   G   G   Q   A
acttcaaaggcggttaatgtcaaaataccagcagtagtacgactatttggtcgtgagctt
 T   S   K   A   V   N   V   K   I   P   A   V   V   R   L   F   G   R   E   L
ctagaaaatgaatttaaatttgagcttagagaagcgaatggcgaggaactccctgtcctt
 L   E   N   E   F   K   F   E   L   R   E   A   N   G   E   E   L   P   V   L
gatacagctcaaaatacaaaagagggtcaagttagatttaaaaatctatcattcgataag
 D   T   A   Q   N   T   K   E   G   Q   V   R   F   K   N   L   S   F   D   K
cctggcaaatactggtatacaatttcagaagtaaaagatgagcttggtggtattgagtat
 P   G   K   Y   W   Y   T   I   S   E   V   K   D   E   L   G   G   I   E   Y
gattcgaaatatattgtagcaaaaataactgtagaagatcgaaacgggcaattacaggca
 D   S   K   Y   I   V   A   K   I   T   V   E   D   R   N   G   Q   L   Q   A
atgatcgaatttattgataatgacaatgtctttaacaatttctatacacctgctccagct
 M   I   E   F   I   D   N   D   N   V   F   N   N   F   Y   T   P   A   P   A
gctgctagtctttcgataaaaaaagtcctcgagggacgtaccttaaacaccggtgaattc
 A   A   S   L   S   I   K   K   V   L   E   G   R   T   L   N   T   G   E   F
gaatttgttttaaaaaatgaaaaaggcgatgaaatcgaaaaggtaagcaatcaagcagat
 E   F   V   L   K   N   E   K   G   D   E   I   E   K   V   S   N   Q   A   D
ggttctgtaaactttagtgccctaacatttacaaaagagggaacctataccctacactgtt
 G   S   V   N   F   S   A   L   T   F   T   K   E   G   T   Y   T   Y   T   V
tcagaagttgatggtggacttggcgatattatctatgacaaatcagatattaaggccact
 S   E   V   D   G   G   L   G   D   I   I   Y   D   K   S   D   I   K   A   T
gttactgtgaaagataacaatcacggacaactagtctcaacagtgacttatgaaaatagc
 V   T   V   K   D   N   N   H   G   Q   L   V   S   T   V   T   Y   E   N   S
gatcaaatcttcgagaatatttttgaatcctgggaagttaatagcgccaaccacggatagc
 D   Q   I   F   E   N   I   L   N   P   G   K   L   I   A   P   T   T   D   S
gttattactgataatgaagtctctaaggaagcaatggccggtaaagagaagggaaatatc
 V   I   T   D   N   E   V   S   K   E   A   M   A   G   K   E   K   G   N   I
gaaccccctaaagagcaaatagctaatgaagagaaggataatattgaagcctctgaaaaa
 E   P   P   K   E   Q   I   A   N   E   E   K   D   N   I   E   A   S   E   K
cagatgccaagcattgtgaacgacatggtcgtaacacctgaaaag
 Q   M   P   S   I   V   N   D   M   V   V   T   P   E   K
```

Figure 11

```
atgaaacgtaagagaacaaataaaccacaacatatgcgtcgcaagagaaaaacacctatc  60
 M  K  R  K  R  T  N  K  P  Q  H  M  R  R  K  R  K  T  P  I   20
atgaaaaacaataagaagatgttatacacatcttcattggctctttccctcttagtaca  120
 M  K  N  N  K  K  M  L  Y  T  S  S  L  A  L  S  L  F  S  T   40
gggatgatttcgacaaatgttttagccatcgaatgggctccacgtactgtttctgaaatt 180
 G  M  I  S  T  N  V  L  A  I  E  W  A  P  R  T  V  S  E  I   60
agcccagaaattgtacaagaagaaggaaggatgacctatactgttcagtatggagatacc 240
 S  P  E  I  V  Q  E  E  G  R  M  T  Y  T  V  Q  Y  G  D  T   80
ttatctgccatcgcctcagctatgaatattgatatggacttgctggcgaaaataaatcaa 300
 L  S  A  I  A  S  A  M  N  I  D  M  D  L  L  A  K  I  N  Q  100
attgcagatgtcaacttgattttccctgatacggtactgacgacgactgttgaccaaaac 360
 I  A  D  V  N  L  I  F  P  D  T  V  L  T  T  T  V  D  Q  N  120
aatcaagtgactcaggttgagattgaagctcctgttcagggaaacacaaatgagaccgtt 420
 N  Q  V  T  Q  V  E  I  E  A  P  V  Q  G  N  T  N  E  T  V  140
caggcaactgttgacctaacaaccaatcaagtaacggttgaggatacggttgttcccttg 480
 Q  A  T  V  D  L  T  T  N  Q  V  T  V  E  D  T  V  V  P  L  160
gatcaaatttcatcagttaccgactcagcgcccgtagaggaagttgtagaacagcctgta 540
 D  Q  I  S  S  V  T  D  S  A  P  V  E  E  V  V  E  Q  P  V  180
gcagaagcacctgtagaggaagttgtagaacaacctgtagtagaagcgcccgtagaggaa 600
 A  E  A  P  V  E  E  V  V  E  Q  P  V  V  E  A  P  V  E  E  200
gttgtagaacagcctgtagtagaagcacctgtagaggaagttgcagaacaacctgtggtt 660
 V  V  E  Q  P  V  V  E  A  P  V  E  E  V  A  E  Q  P  V  V  220
gaggcacctgtagaggaagtggtggagcaacctgtggttgaggcacctgtagaggaagtt 720
 E  A  P  V  E  E  V  V  E  Q  P  V  V  E  A  P  V  E  E  V  240
gcagaacaacctgtagtagaagcacctgtagaacagcctgtagttgaaactccacaagtg 780
 A  E  Q  P  V  V  E  A  P  V  E  Q  P  V  V  E  T  P  Q  V  260
acagccctatcaactactacaacaagtacaagtgcttatgatgtcggtttgcaacctcag 840
 T  A  L  S  T  T  T  S  T  S  A  Y  D  V  G  L  Q  P  Q  280
gtagcagccttccgcgcagaagtagctaatgccttcggtattacttctttctcaggttac 900
 V  A  A  F  R  A  E  V  A  N  A  F  G  I  T  S  F  S  G  Y  300
cgtcctggtgattctggcgaccatggtaagggattggcaattgactttatggtgcctgag 960
 R  P  G  D  S  G  D  H  G  K  G  L  A  I  D  F  M  V  P  E  320
agctcagctctaggagatcaagtggcagcttatgcagttgcaaacttagcttctaaaaat 1020
 S  S  A  L  G  D  Q  V  A  A  Y  A  V  A  N  L  A  S  K  N  340
atcaactacatcatttggaaacagcgcttctatgcgccgtatgacagtatctatggtcca 1080
 I  N  Y  I  I  W  K  Q  R  F  Y  A  P  Y  D  S  I  Y  G  P  360
gcctatacatggaatctgatgccagaccgtggtagcattacagaaaaccactacgatcat 1140
 A  Y  T  W  N  L  M  P  D  R  G  S  I  T  E  N  H  Y  D  H  380
gtgcatgtatcttttaattag                                         1158
 V  H  V  S  F  N  -                                           386
```

Figure 13

86.6% identity in 670 residues overlap; Score: 5248.0; Gap frequency: 13.4%

```
SEQ ID NO 1     1  MNTKKWRTSLLIPGIVLFGTVALVNNVSAQEVKNTIISAKQPDGGQATSKAVNVKIPAVV
SEQ ID NO 2     1  MNTKKWRTSLLIPGIVLFGTVALVNNVSAQEVKNTIISAKQPDGGQATSKAVNVKIPAVV
                   ************************************************************

SEQ ID NO 1    61  RLFGRELLENEFKFELREANGEELPVLDTAQNTKEGQVRFKNLSFDKPGKYWYTISEVKD
SEQ ID NO 2    61  RLFGRELLENEFKFELREANGEELPVLDTAQNTKEGQVRFKNLSFDKPGKYWYTISEVKD
                   ************************************************************

SEQ ID NO 1   121  ELGGIEYDSKYIVAKITVEDRNGQLQAMIEFIDNDNVFNNFYTPAPAAASLSIKKVLEGR
SEQ ID NO 2   121  ELGGIEYDSKYIVAKITVEDRNGQLQAMIEFIDNDNVFNNFYTPAPAAASLSIKKVLEGR
                   ************************************************************

SEQ ID NO 1   181  TLNTGEFEFVLKNEKGDEIEKVSNQADGSVNFSALTFTKEGTYTYTVSEVDGGLGDIIYD
SEQ ID NO 2   181  TLNTGEFEFVLKNEKGDEIEKVSNQADGSVNFSALTFTKEGTYTYTVSEVDGGLGDIIYD
                   ************************************************************

SEQ ID NO 1   241  KSDIKATVTVKDNNHGQLVSTVTYENSDQIFENILNPGKLIAPTTDSVITDNEVSKEAMA
SEQ ID NO 2   241  KSDIKATVTVKDNNHGQLVSTVTYENSDQIFENILNPGKLIAPTTDSVITDNEVSKEAMA
                   ************************************************************

SEQ ID NO 1   301  GKEKGNIEPPKEQIANEEKDNIEASEKQMPSIVNDMVVTPEKQMTNKENDKVVISEKQMP
SEQ ID NO 2   301  GKEKGNIEPPKEQIANEEKDNIEASEKQMPS-----------------------------
                   ******************************

SEQ ID NO 1   361  SVVNENAVTPEKQMTNKENDNIETSEKQMPSVVNENAVTPEKQMTNKEKDNIETSEKQMP
SEQ ID NO 2   332  ------------------------------------------------------------

SEQ ID NO 1   421  SVVNENAVTPEKQMTNKEKDNIETSEKQMPSIVNDMVVTPQEQMANKENDKVVISEKQMP
SEQ ID NO 2   331  -VVNENAVTPEKQMTNKEKDNIETSEKQMPSIVNDMVVTPQEQMANKENDKVVISEKQMP
                    ***********************************************************

SEQ ID NO 1   481  SIVNDMVVTPQEQMANKENDKVVISEKQMPSIVNDMVVTPQEQMANKENDKVVISEKQMP
SEQ ID NO 2   390  SIVNDMVVTPQEQMANKENDKVVISEKQMPSIVNDMVVTPQEQMANKENDKVVISEKQMP
                   ************************************************************

SEQ ID NO 1   541  SIVNDMVVTPQEQMANKENDKVETSEKQMPVNEKDNAVTPEKQMANKEKENIETSKKQIP
SEQ ID NO 2   450  SIVNDMVVTPQEQMANKENDKVETSEKQMPVNEKDNAVTPEKQMANKEKENIETSKKQIP
                   ************************************************************

SEQ ID NO 1   601  VNENNQNGTVEENSNTKPTTEKTDKQETSTFKTETAKQILPVTGEKGSLWLLTSGIIGLA
SEQ ID NO 2   510  VNENNQNGTVEENSNTKPTTEKTDKQETSTFKTETAKQILPVTGEKGSLWLLTSGIIGLA
                   ************************************************************

SEQ ID NO 1   661  IALFTRKRKL
SEQ ID NO 2   570  IALFTRKRKL
                   **********
```

Figure 25

```
77.6% identity in 670 residues overlap; Score: 4412.0; Gap frequency: 22.4%

SEQ ID NO 1    1 MNTKKWRTSLLIPGIVLFGTVALVNNVSAQEVKNTIISAKQPDGGQATSKAVNVKIPAVV
SEQ ID NO 3    1 MNTKKWRTSLLIPGIVLFGTVALVNNVSAQEVKNTIISAKQPDGGQATSKAVNVKIPAVV
                 ************************************************************

SEQ ID NO 1   61 RLFGRELLENEFKFELREANGEELPVLDTAQNTKEGQVRFKNLSFDKPGKYWYTISEVKD
SEQ ID NO 3   61 RLFGRELLENEFKFELREANGEELPVLDTAQNTKEGQVRFKNLSFDKPGKYWYTISEVKD
                 ************************************************************

SEQ ID NO 1  121 ELGGIEYDSKYIVAKITVEDRNGQLQAMIEFIDNDNVFNNFYTPAPAAASLSIKKVLEGR
SEQ ID NO 3  121 ELGGIEYDSKYIVAKITVEDRNGQLQAMIEFIDNDNVFNNFYTPAPAAASLSIKKVLEGR
                 ************************************************************

SEQ ID NO 1  181 TLNTGEFEFVLKNEKGDEIEKVSNQADGSVNFSALTFTKEGTYTYTVSEVDGGLGDIIYD
SEQ ID NO 3  181 TLNTGEFEFVLKNEKGDEIEKVSNQADGSVNFSALTFTKEGTYTYTVSEVDGGLGDIIYD
                 ************************************************************

SEQ ID NO 1  241 KSDIKATVTVKDNNHGQLVSTVTYENSDQIFENILNPGKLIAPTTDSVITDNEVSKEAMA
SEQ ID NO 3  241 KSDIKATVTVKDNNHGQLVSTVTYENSDQIFENILNPGKLIAPTTDSVITDNEVSKEAMA
                 ************************************************************

SEQ ID NO 1  301 GKEKGNIEPPKEQIANEEKDNIEASEKQMPSIVNDMVVTPEKQMTNKENDKVVISEKQMP
SEQ ID NO 3  301 GKEKGNIEPPKEQIANEEKDNIEASEKQMPSIVNDMVVTPEKQMTNKENDKVVISEKQMP
                 ************************************************************

SEQ ID NO 1  361 SVVNENAVTPEKQMTNKENDNIETSEKQMPSVVNENAVTPEKQMTNKEKDNIETSEKQMP
SEQ ID NO 3  361 SVVNENAVTPEKQMTNKENDNIETSEKQMPSVVNENAVTPEKQMTNKEKDNIETSEKQMP
                 ************************************************************

SEQ ID NO 1  421 SVVNENAVTPEKQMTNKEKDNIETSEKQMPSIVNDMVVTPQEQMANKENDKVVISEKQMP
SEQ ID NO 3  421 SVVNENAVTPEKQMTNKEKDNIETSEKQ--------------------------------
                 ***************************

SEQ ID NO 1  481 SIVNDMVVTPQEQMANKENDKVVISEKQMPSIVNDMVVTPQEQMANKENDKVVISEKQMP
SEQ ID NO 3  449 ------------------------------------------------------------

SEQ ID NO 1  541 SIVNDMVVTPQEQMANKENDKVETSEKQMPVNEKDNAVTPEKQMANKEKENIETSKKQIP
SEQ ID NO 3  448 ----------------------------------------------------------IP
                                                                           **

SEQ ID NO 1  601 VNENNQNGTVEENSNTKPTTEKTDKQETSTFKTETAKQILPVTGEKGSLWLLTSGIIGLA
SEQ ID NO 3  450 VNENNQNGTVEENSNTKPTTEKTDKQETSTFKTETAKQILPVTGEKGSLWLLTSGIIGLA
                 ************************************************************

SEQ ID NO 1  661 IALFTRKRKL
SEQ ID NO 3  510 IALFTRKRKL
                 **********
```

Figure 26

84.3% identity in 580 residues overlap; Score: 4463.0; Gap frequency: 10.3%

```
SEQ ID NO 3   1 MNTKKWRTSLLIPGIVLFGTVALVNNVSAQEVKNTIISAKQPDGGQATSKAVNVKIPAVV
SEQ ID NO 2   1 MNTKKWRTSLLIPGIVLFGTVALVNNVSAQEVKNTIISAKQPDGGQATSKAVNVKIPAVV
                ************************************************************

SEQ ID NO 3  61 RLFGRELLENEFKFELREANGEELPVLDTAQNTKEGQVRFKNLSFDKPGKYWYTISEVKD
SEQ ID NO 2  61 RLFGRELLENEFKFELREANGEELPVLDTAQNTKEGQVRFKNLSFDKPGKYWYTISEVKD
                ************************************************************

SEQ ID NO 3 121 ELGGIEYDSKYIVAKITVEDRNGQLQAMIEFIDNDNVFNNFYTPAPAAASLSIKKVLEGR
SEQ ID NO 2 121 ELGGIEYDSKYIVAKITVEDRNGQLQAMIEFIDNDNVFNNFYTPAPAAASLSIKKVLEGR
                ************************************************************

SEQ ID NO 3 181 TLNTGEFEFVLKNEKGDEIEKVSNQADGSVNFSALTFTKEGTYTYTVSEVDGGLGDIIYD
SEQ ID NO 2 181 TLNTGEFEFVLKNEKGDEIEKVSNQADGSVNFSALTFTKEGTYTYTVSEVDGGLGDIIYD
                ************************************************************

SEQ ID NO 3 241 KSDIKATVTVKDNNHGQLVSTVTYENSDQIFENILNPGKLIAPTTDSVITDNEVSKEAMA
SEQ ID NO 2 241 KSDIKATVTVKDNNHGQLVSTVTYENSDQIFENILNPGKLIAPTTDSVITDNEVSKEAMA
                ************************************************************

SEQ ID NO 3 301 GKEKGNIEPPKEQIANEEKDNIEASEKQMPS-----------------------------
SEQ ID NO 2 301 GKEKGNIEPPKEQIANEEKDNIEASEKQMPSVVNENAVTPEKQMTNKEKDNIETSEKQMP
                ******************************

SEQ ID NO 3 332 -IVNDMVVTPEKQMTNKENDKVVISEKQMPSVVNENAVTPEKQMTNKENDNIETSEKQMP
SEQ ID NO 2 361 SIVNDMVVTPQEQMANKENDKVVISEKQMPSIVNDMVVTPQEQMANKENDKVVISEKQMP
                 ********* **  *************** ***  ** *****       ******

SEQ ID NO 3 391 SVVNENAVTPEKQMTNKEKDNIETSEKQMPSVVNE-------------------------
SEQ ID NO 2 421 SIVNDMVVTPQEQMANKENDKVVISEKQMPSIVNDMVVTPQEQMANKENDKVETSEKQMP
                * **   ***  ** *** *        *******  **

SEQ ID NO 3 426 -----NAVTPEKQMTNKEKDNIETSEKQIPVNENNQNGTVEENSNTKPTTEKTDKQETST
SEQ ID NO 2 481 VNEKDNAVTPEKQMANKEKENIETSKKQIPVNENNQNGTVEENSNTKPTTEKTDKQETST
                     *********  ***** *****  *******************************

SEQ ID NO 3 481 FKTETAKQILPVTGEKGSLWLLTSGIIGLAIALFTRKRKL
SEQ ID NO 2 541 FKTETAKQILPVTGEKGSLWLLTSGIIGLAIALFTRKRKL
                ****************************************
```

CLUSTAL (-like) formatted alignment by MAFFT (v5.860)

```
SEQ ID NO 1    MNTKKWRTSLLIPGIVLFGTVALVNNVSAQEVKNTIISAKQPDGGQATSKAVNVKIPAVV
SEQ ID NO 2    MNTKKWRTSLLIPGIVLFGTVALVNNVSAQEVKNTIISAKQPDGGQATSKAVNVKIPAVV
SEQ ID NO 3    MNTKKWRTSLLIPGIVLFGTVALVNNVSAQEVKNTIISAKQPDGGQATSKAVNVKIPAVV
               ************************************************************

SEQ ID NO 1    RLFGRELLENEFKFELREANGEELPVLDTAQNTKEGQVRFKNLSFDKPGKYWYTISEVKD
SEQ ID NO 2    RLFGRELLENEFKFELREANGEELPVLDTAQNTKEGQVRFKNLSFDKPGKYWYTISEVKD
SEQ ID NO 3    RLFGRELLENEFKFELREANGEELPVLDTAQNTKEGQVRFKNLSFDKPGKYWYTISEVKD
               ************************************************************

SEQ ID NO 1    ELGGIEYDSKYIVAKITVEDRNGQLQAMIEFIDNDNVFNNFYTPAPAAASLSIKKVLEGR
SEQ ID NO 2    ELGGIEYDSKYIVAKITVEDRNGQLQAMIEFIDNDNVFNNFYTPAPAAASLSIKKVLEGR
SEQ ID NO 3    ELGGIEYDSKYIVAKITVEDRNGQLQAMIEFIDNDNVFNNFYTPAPAAASLSIKKVLEGR
               ************************************************************

SEQ ID NO 1    TLNTGEFEFVLKNEKGDEIEKVSNQADGSVNFSALTFTKEGTYTYTVSEVDGGLGDIIYD
SEQ ID NO 2    TLNTGEFEFVLKNEKGDEIEKVSNQADGSVNFSALTFTKEGTYTYTVSEVDGGLGDIIYD
SEQ ID NO 3    TLNTGEFEFVLKNEKGDEIEKVSNQADGSVNFSALTFTKEGTYTYTVSEVDGGLGDIIYD
               ************************************************************

SEQ ID NO 1    KSDIKATVTVKDNNHGQLVSTVTYENSDQIFENILNPGKLIAPTTDSVITDNEVSKEAMA
SEQ ID NO 2    KSDIKATVTVKDNNHGQLVSTVTYENSDQIFENILNPGKLIAPTTDSVITDNEVSKEAMA
SEQ ID NO 3    KSDIKATVTVKDNNHGQLVSTVTYENSDQIFENILNPGKLIAPTTDSVITDNEVSKEAMA
               ************************************************************

SEQ ID NO 1    GKEKGNIEPPKEQIANEEKDNIEASEKQMPSIVNDMVVTPEKQMTNKENDKVVISEKQMP
SEQ ID NO 2    GKEKGNIEPPKEQIANEEKDNIEA------------------------------------
SEQ ID NO 3    GKEKGNIEPPKEQIANEEKDNIEA------------------------------------
               ************************

SEQ ID NO 1    SVVNENAVTPEKQMTNKENDNIETSEKQMPSVVNENAVTPEKQMTNKEKDNIETSEKQMP
SEQ ID NO 2    ------------------------------------------------------SEKQMP
SEQ ID NO 3    ------------------------------------------------------------

SEQ ID NO 1    SVVNENAVTPEKQMTNKEKDNIETSEKQMPSIVNDMVVTPQEQMANKENDKVVISEKQMP
SEQ ID NO 2    SVVNENAVTPEKQMTNKEKDNIETSEKQMPSIVNDMVVTPQEQMANKENDKVVISEKQMP
SEQ ID NO 3    ------------------------------------------------------SEKQMP
                                                                     ******
```

Figure 28 (continuation)

```
SEQ ID NO 1    SIVNDMVVTPQEQMANKENDKVVISEKQMPSIVNDMVVTPQEQMANKENDKVVISEKQMP
SEQ ID NO 2    SIVNDMVVTPQEQMANKENDKVVISEKQMPSIVNDMVVTPQEQMANKENDKVVISEKQMP
SEQ ID NO 3    SIVNDMVVTPEKQMTNKENDKVVISEKQMPSVVNENAVTPEKQMTNKENDNIETSEKQMP
               **********::**:****************:**: .***::**:****::  ******

SEQ ID NO 1    SIVNDMVVTPQEQMANKENDKVETSEKQMPVNEKDNAVTPEKQMANKEKENIETSKKQIP
SEQ ID NO 2    SIVNDMVVTPQEQMANKENDKVETSEKQMPVNEKDNAVTPEKQMANKEKENIETSKKQIP
SEQ ID NO 3    SVVNENAVTPEKQMTNKEKDNIETSEKQMPSVVNENAVTPEKQMTNKEKDNIETSEKQIP
               *:**: .***::**:***:*::********   ::*********:****:*****:****

SEQ ID NO 1    VNENNQNGTVEENSNTKPTTEKTDKQETSTFKTETAKQILPVTGEKGSLWLLTSGIIGLA
SEQ ID NO 2    VNENNQNGTVEENSNTKPTTEKTDKQETSTFKTETAKQILPVTGEKGSLWLLTSGIIGLA
SEQ ID NO 3    VNENNQNGTVEENSNTKPTTEKTDKQETSTFKTETAKQILPVTGEKGSLWLLTSGIIGLA
               ************************************************************

SEQ ID NO 1    IALFTRKRKL
SEQ ID NO 2    IALFTRKRKL
SEQ ID NO 3    IALFTRKRKL
               **********
```

STREPTOCOCCUS SUIS POLYPEPTIDES AND POLYNUCLEOTIDES ENCODING SAME AND THEIR USE IN VACCINAL AND DIAGNOSTIC APPLICATIONS

FIELD OF THE INVENTION

The present invention relates to the field of *Streptococcus*. More specifically, the present invention relates to the identification of polypeptides and polynucleotide sequences encoding the same which are involved in the pathogenic mechanism of *S. suis*. The present invention also relates to the use of such polypeptides in compositions and methods for the prevention, the treatment and diagnosis of *S. suis*-associated diseases and infections caused by *S. suis*.

SEQUENCE LISTING

In accordance with 37 CFR §1.52(e)(5), the present specification makes reference to a Sequence Listing (submitted electronically as a .txt file named "SeqListing.txt" on Jan. 31, 2011). The .txt file was generated on Jan. 20, 2011 and is 40 kb in size. The entire contents of the Sequence Listing are herein incorporated by reference.

BACKGROUND OF THE INVENTION

*Streptococcus suis* is an important swine pathogen that causes many pathological conditions such as arthritis, endocarditis, meningitis, pneumonia and septicemia (13, 14). It is also an important zoonotic agent for people in contact with contaminated pigs or their by-products, causing meningitis and endocarditis (1, 36). Thirty-three serotypes (types 1 to 31, 33 and 1/2) based on capsular antigens are currently known (9-11, 15, 17, 31). Type 2 is considered the most virulent and prevalent type in diseased pigs. The mechanisms involved in the pathogenesis and virulence of *S. suis* are not completely understood (13) and attempts to control the infection are hampered by the lack of effective vaccines.

Several approaches have been made to develop vaccines for *S. suis*. However, little success was achieved because the protection was either serotype or strain dependent and results, in most instances, were equivocal (16, 30). For example, some protection with killed whole cells and live avirulent vaccines were reported, but this required repeated immunization and the protection against heterologous challenges was not determined (18, 38). Exposure of young pigs with live virulent strains showed a positive effect in reducing clinical signs characteristics of *S. suis* infection, but not in central nervous sign and mortality (35). Since the *S. suis* capsule plays an important role in virulence, attempts have been made to develop a vaccine based on capsular material. However, this vaccination was unsatisfactory because the capsular polysaccharide is poorly immunogenic (7). More recently, interest has shifted toward protein antigens of *S. suis* as vaccine candidates. Subunit vaccines using suilysin (20), or MRP (muramidase-released protein) and EF (extracellular proteins factor) (39) have been shown to protect pigs from homologous and heterologous serotype 2 strains, but their use is hindered by the fact that a substantial number of the virulent strains in some geographical regions do not express these proteins (8, 12, 29). Thus, identification of other antigenic factors, especially surface proteins, could contribute to the development of a subunit vaccine.

There is thus a need for the discovery and use of new targets for the prevention, the treatment and the diagnosis of *S. suis*-associated diseases and infections caused by *S. suis*.

SUMMARY OF THE INVENTION

An object of the invention is to fulfill the above-mentioned need. More specifically, the object is achieved by providing an isolated polypeptide comprising at least 15 contiguous amino acids in the N-terminal region of the amino acid sequence set forth in SEQ ID NO: 1.

Another object of the invention also concerns an polynucleotide encoding a polypeptide as defined above.

The present invention is further concerned with an antibody which specifically binds to a polypeptide of the invention.

A further object of the invention is to provide a vector comprising the polynucleotide as defined above.

Yet another object of the invention is to provide a composition for preventing or treating *Streptococcus suis*-associated diseases or infection caused by *S. suis*, comprising an acceptable carrier and at least one of the following elements:
  a polypeptide as defined above;
  a polypeptide as defined above;
  an antibody as defined above;
  a vector as defined above.

Another object of the invention concerns a method for treating and/or preventing a *Streptococcus suis*-associated disease or infection in an animal, the method comprising the step of administering to the animal a composition as defined above.

A further object concerns a method for detecting the presence or absence of a *Streptococcus suis* strain in a sample, comprising the steps of:
  a) contacting the sample with an antibody of the invention for a time and under conditions sufficient to form an immune complex; and
  b) detecting the presence or absence of the immune complex formed in a).

Another object of the invention concerns a method for detecting the presence or absence of antibodies raised against a *Streptococcus suis* strain in a sample, comprising the steps of:
  a) contacting the sample with a polypeptide of the invention for a time and under conditions sufficient to form an immune complex; and
  b) detecting the presence or absence of the immune complex formed in a).

The present invention also provide in another object a diagnostic kit for the detection of the presence or absence of antibodies indicative of *Streptococcus* suis strain, comprising:
  a polypeptide according to the invention;
  a reagent to detect polypeptide-antibody immune complex;
  a biological reference sample lacking antibodies that immunologically bind with said peptide; and
  a comparison sample comprising antibodies which can specifically bind to said peptide;
wherein said polypeptide, reagent, biological reference sample, and comparison sample are present in an amount sufficient to perform said detection.

Yet another object is to provide a diagnostic kit for the detection of the presence or absence of antibodies indicative of *Streptococcus suis* strain, comprising:
  an antibody of the invention;
  a reagent to detect polypeptide-antibody immune complex;
  a biological reference sample polypeptides that immunologically bind with said antibody; and
  a comparison sample comprising polypeptides which can specifically bind to said peptide;

wherein said antibody, reagent, biological reference sample, and comparison sample are present in an amount sufficient to perform said detection.

Further objects are to provide an isolated polypeptide comprising an amino acid sequence substantially identical to the sequence as set forth in SEQ ID NO 11 or functional derivative thereof, and an isolated polynucleotide encoding said polypeptide, and their use in a composition and/or a method for treating and/or preventing a *Streptococcus suis*-associated disease or infection in an animal.

BRIEF DESCRIPTION OF THE FIGURES

Unless specifically indicated to the contrary, the terms "SP1" and "Sao" are used interchangeably.

FIG. 2: Nucleotide sequence (SEQ ID NO: 5) and deduced amino acid sequence (SEQ ID NO: 1) of the gene encoding a preferred polypeptide of a first embodiment of the invention, namely the SP1 (or Sao) protein of *S. suis*. The Shine-Dalgarno sequence is in italic letters and underlined. The initiation codon, ATG, and the stop codon, TAA, are shown in bold type. The two hydrophobic segments at the both N- and C-terminal ends of SP1 are underlined. The vertical arrow indicates the cleavage site of potential signal peptidase. R1 to R10 indicate the beginning of the repeating units. The potential cell wall-associated region is underlined with dash line. The LPVTG (SEQ ID NO: 10) membrane anchor motif is boxed, and the charged C-terminal tail is indicated.

FIG. 3: Amino acid sequence alignment of the region $Lys^{319}$ to $Val^{601}$ of SP1 (SEQ ID NO: 18) with the AvrXa7 avirulence factor of *Xanthomonas oryzae* pv. *oryzae* (SEQ ID NO: 17). The vertical lines indicate positions with identical residues. Double dots represent conserved substitutions and single dots represent functional substitutions.

FIG. 4: Expression of MBP-SP1 fusion protein in *E. coli* XL1-Blue and purification of the recombinant mature SP1. The Coomassie-stained gel (A) and Western blot analysis (B) of the corresponding samples probed with convalescent swine serum show *E. coli* whole cell lysate before (lane 1) and after (lane 2) induction of IPTG, extract of cytoplasm (lane 3), affinity purified MBP-SP1 fusion protein (lane 4), SP1 and MBP cleaved by factor X (lane 5) and recombinant SP1 devoid of MBP purified using ion-exchange chromatography (lane 6). The molecular masses of standard proteins are indicated on the left.

FIG. 11: Nucleotide sequence (SEQ ID NO: 8) of a preferred functional polynucleotide fragment of the invention, namely the SP1A gene fragment and the deduced amino acid sequences (SEQ ID NO: 4).

FIG. 13: Nucleotide sequence (SEQ ID NO: 12) and deduced amino acid sequence (SEQ ID NO: 11) of the gene encoding a preferred polypeptide of another embodiment of the invention, namely the SP2 protein of *S. suis*. The positive charge cluster at N-terminal end of SP2 is underlined. The potential N-terminal signal sequence is underlined with dash line. The LysM domain is boxed, and the arrows indicate the beginning of the repeating units.

FIG. 25: Amino acid sequence alignment between two SP1 polypeptides according to preferred embodiments of the invention, namely SEQ ID NO 1 and 2.

FIG. 26: Amino acid sequence alignment between two SP1 polypeptides according to preferred embodiments of the invention, namely SEQ ID NO 1 and 3.

FIG. 27: Amino acid sequence alignment between two SP1 polypeptides according to preferred embodiments of the invention, namely SEQ ID NO 2 and 3.

FIG. 28: Amino acid sequence alignment between three SP1 polypeptides according to preferred embodiments of the invention, namely SEQ ID NO 1, 2 and 3.

BRIEF DESCRIPTION OF THE INVENTION

Figure 1:
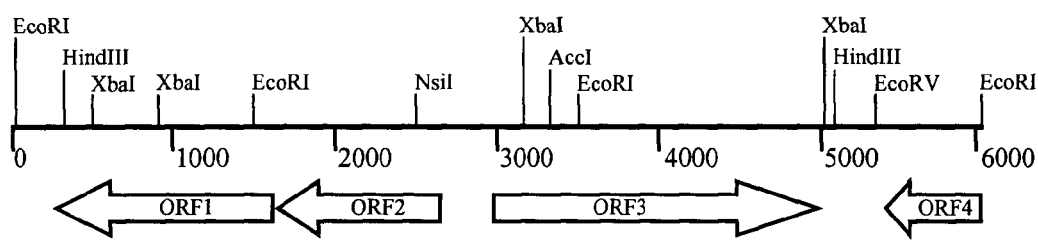
FIG. 1: Schematic representation and partial restriction map of a preferred polynucleotide of the invention, namely the DNA insert of recombinant plasmid pSS735. Numbers indicate the distance (in base pairs) from the 5' end.

The inventors have surprisingly found two novel *S. suis* polypeptides and polynucleotides encoding same that are involved during the *S. suis* pathogenic mechanism. In this connection, the present invention specifically relates to their identification and to the use of said polypeptides or polynucleotides in compositions and methods for the prevention, the treatment and the diagnosis of *Streptococcus suis*-associated diseases or infection caused by *S. suis*.

A non-exhaustive list of *Streptococcus suis*-associated diseases which the methods of the invention may be useful for, includes those, such as arthritis, endocarditis, meningitis, pneumonia and septicemia.

Definitions

The term "isolated" is meant to describe a polynucleotide, a polypeptide or an antibody that is in an environment different from that in which the polynucleotide, the polypeptide, the antibody, or the host cell naturally occurs.

The term "animal" refers to any animal susceptible to be infected by a *Streptococcus* strain, such as *S. suis*. Specifically, such an animal may be, but not limited to, mice, pig, sheep, horse and human. More specifically, the animal consists of a pig.

The term "treating" refers to a process by which the symptoms of an infection or a disease associated with a *Streptococcus* strain are alleviated or completely eliminated. As used herein, the term "preventing" refers to a process by which symptoms of an infection or a disease associated with a *Streptococcus* strain are obstructed or delayed.

The term "protective response" means prevention of onset of a *Streptococcus suis*-associated disease or an infection caused by *S. suis*. or lessening the severity of such a disease existing in an animal. The level of "protective response" may be evaluated, for instance, by the assignment of clinical scores such as those defined in Example 4.

The expression "an acceptable carrier" means a vehicle for containing the compounds obtained by the method of the invention that can be administered to an animal host without adverse effects. Suitable carriers known in the art include, but are not limited to, gold particles, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

The term "fragment", as used herein, refers to a polynucleotide sequence (e.g., cDNA) which is an isolated portion of the subject nucleic acid constructed artificially (e.g., by chemical synthesis) or by cleaving a natural product into multiple pieces, using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art.

1 Polynucleotides and Polypeptides of the Invention

In a first embodiment, the present invention concerns an isolated polypeptide which consists of a surface protein, and more particularly a C-terminal-anchored surface protein of *Streptococcus suis*, namely called SP1 or Sao. As shown in the Example section, the SP1 polypeptide advantageously elicits a protective response to a *Streptococcus suis* strain challenge when administered to an animal, such as a pig.

Specifically, the isolated polypeptide of the first embodiment of the invention comprises at least 15 or even preferably at least 25 or even more at least 35 contiguous amino acids in the N-terminal region of the amino acid sequence set forth in SEQ ID NO: 1. As one skilled in the art may appreciate, the term "N-terminal region" in the context of the present invention when referring to the Sao protein, preferably consists of the region spanning from amino acid residue 1 to 293 of the amino acid sequence set forth in SEQ ID NO: 1.

According to a preferred embodiment, the isolated polypeptide of the first embodiment may further comprises at least one repetitive amino acid sequence such as shown in FIG. 2. More particularly, a repetitive amino acid sequence contemplated by the present invention consists of the amino acid sequence shown in SEQ ID NO 9, wherein $Xaa_1$ is Val, Thr or Ile;
$Xaa_3$ is Lys or Glu;
$Xaa_4$ is Lys or Glu;
$Xaa_5$ is Ala or Gln;
$Xaa_7$ is Thr or Pro;
$Xaa_8$ is Gly, Ser or Val;
$Xaa_9$ is Lys, Val, Ile or Asn;
$Xaa_{10}$ is Glu or Val;
$Xaa_{11}$ is Lys or Asn;
$Xaa_{12}$ is Gly, Glu or Asp;
$Xaa_{13}$ is Asn or Met;
$Xaa_{14}$ is Ile, Ala or Val;
$Xaa_{15}$ is Glu or Val;
$Xaa_{16}$ is Pro or Thr;
$Xaa_{18}$ is Glu or Gln;
$Xaa_{19}$ is Lys or Glu;
$Xaa_{22}$ is Thr or Ala
$Xaa_{26}$ is Lys or Asn;
$Xaa_{27}$ is Asp or Glu;
$Xaa_{28}$ is Asn or Lys;
$Xaa_{29}$ is Ile or Val and
$Xaa_{30}$ is Glu or Val.

It will be understood that the preferred SP1 polypeptide of the invention may comprises only one of said repetitive sequence, whereas in some other cases, the preferred SP1 polypeptide of the invention may comprises at least two repetitive sequences or even more than ten of such repetitive sequences.

In accordance with another preferred embodiment of the invention, the isolated SP1 polypeptide advantageously comprises at least 15 or even preferably 25 or even more preferably 35 contiguous amino acids in the C-terminus region of the amino acid sequence set forth in SEQ ID NO: 1. Preferably, the C-terminus region comprises a membrane anchor motif, such as the one consisting of the amino acid sequence as set forth is SEQ ID NO 10, namely Leu Pro Val Thr Gly.

As one skilled in the art may appreciate, the term "C-terminus region" in the context of the present invention when referring to the SP1 protein, preferably consists of the region spanning from amino acid residue 593 to 670 of the amino acid sequence set forth in SEQ ID NO: 1.

In accordance with an even more preferred embodiment, a SP1 polypeptide of the invention comprises an amino acid sequence substantially identical to a sequence selected from the group consisting of SEQ ID NOS 1 to 3 or functional derivative thereof. Most preferably, a SP1 polypeptide of the invention consists of an amino acid sequence substantially identical to the sequence shown in SEQ ID NO 1, or a functional derivative thereof.

A "functional derivative", as is generally understood and used herein, refers to a protein/peptide sequence that possesses a functional biological activity that is substantially similar to the biological activity of the whole protein/peptide sequence. In other words, it preferably refers to a polypeptide or fragment(s) thereof that substantially retain(s) the capacity of eliciting an immune response, such as a protective response to a S. suis strain challenge when said functional derivative is administered to an animal. A preferred functional derivative contemplated by the present invention comprises an amino acid sequence substantially identical to the sequence as set forth in SEQ ID NO 4. More specifically, a preferred functional derivative consists of a 315-amino acids fragment ($S^{28}$-$K^{342}$) of SEQ ID NO 1. Such a fragment or polypeptide is designed as SP1A and its nucleotide and amino acid sequences are shown in FIG. 11. SP1A strongly reacted with a convalescent swine serum in immunoblots and immunization with recombinant SP1A elicits significant humoral antibody responses in pigs and mice, demonstrating that SP1A is highly immunogenic. (See Example 5)

According to a second embodiment, the present invention relates to another isolated *S. suis* polypeptide, namely called SP2, which advantageously elicits a protective response in an animal.

Specifically, the isolated polypeptide of the second embodiment of the invention comprises an amino acid sequence substantially identical to a sequence as set forth in SEQ ID NO: 11 or functional derivative thereof.

By "substantially identical" when referring to an amino acid sequence, it will be understood that the polypeptide of the present invention preferably has an amino acid sequence having at least 75% homology, or even preferably 85% homology, or even more preferably 95% homology to part or all of the sequence shown in SEQ ID NOS 1 to 4 and 11.

"Homology" in this context, means identical or similar to the referenced sequence while straightforward replacements/modifications of any of the amino acids provided, are included as well. A homology search in this respect can be performed with the BLAST-P (Basic Local Alignment Search Tool), a program well known to those of skill in the art. For the corresponding nucleic acid sequence, homology is referred to the BLASTX and BLASTN programs known in the art.

The present invention also concerns an isolated polynucleotide encoding a preferred SP1 or a preferred SP2 polypeptide of the invention. Preferably, the isolated polynucleotide of the invention comprises a nucleotide sequence substantially identical to the sequence shown in SEQ ID NOS 5 to 7 when referring to SP1 and SEQ ID NO 12 when referring to SP2 and their respective functional fragments thereof.

By "substantially identical" when referring to a nucleic acid sequence, it will be understood that the polynucleotide of the invention preferably has a nucleic acid sequence which is at least 65% identical, more particularly 80% identical and even more particularly 95% identical to part or all of the sequence shown in SEQ ID NOS 5 to 7 and 12 or functional fragments thereof.

A "functional fragment", as is generally understood and used herein, refers to a nucleic acid sequence that encodes for a functional biological activity that is substantially similar to the biological activity of the whole nucleic acid sequence. In other words, and within the context of the present invention, it preferably refers to a nucleic acid or fragment(s) thereof that substantially retains the capacity of encoding a polypeptide/protein which elicits an immune response, and more preferably a protective response, to a *Streptococcus suis* strain challenge when administered to an animal. For instance, such a fragment is the polynucleotide shown in SEQ ID NO 8, which codes for the SP1A polypeptide as defined above.

In another embodiment, the invention is further directed to vector (e.g., cloning or expression vector) comprising a polynucleotide of the invention as defined above.

As used herein, the term "vector" refers to a polynucleotide construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, or a "viral vector" which is designed to result in the production of a recombinant virus or virus-like particle, or "shuttle vectors", which comprise the attributes of more than one type of vector.

A number of vectors suitable for stable transfection of cells and bacteria are available to the public (e.g., plasmids, adenoviruses, baculoviruses, yeast baculoviruses, plant viruses, adeno-associated viruses, retroviruses, Herpes Simplex Viruses, Alphaviruses, Lentiviruses), as are methods for constructing such cell lines. It will be understood that the present invention encompasses any type of vector comprising any of the polynucleotide molecule of the invention.

2. Antibodies

In another embodiment, the invention features antibodies that specifically bind to the polypeptides of the invention. More specifically, the antibody is a purified polyclonal or monoclonal antibody that specifically binds to the preferred *S. suis* polypeptides as defined above.

The antibodies of the invention may be prepared by a variety of methods known to one skilled in the art. For example, the polypeptides of the invention may be administered to an animal in order to induce the production of polyclonal antibodies. Alternatively, and as mentioned above, antibodies used as described herein may be monoclonal antibodies, which are prepared using known hybridoma technologies (see, e.g., Hammerling et al., In Monoclonal Antibodies and T-Cell Hybridomas, Elsevier, N.Y., 1981; Charland, N., M. Jacques, S. Iacouture and M. Gottschalk. 1997. Characterization and protective activity of a monoclonal antibody against a capsular epitope shared by *Streptococcus suis* serotypes 1, 2 and ½. Microbiology 143 (Pt 11): 3607-14).

With respect to antibodies of the present invention, the term "specifically binds to" refers to antibodies that bind with a relatively high affinity to one or more epitopes of the SP1 or SP2 polypeptide of the invention, but which do not substantially recognize and bind molecules other than the SP1 or SP2 polypeptides of the invention. As used herein, the term "relatively high affinity" means a binding affinity between the antibody and the SP1 or SP2 polypeptides of at least $10^6$ $M^{-1}$, and preferably of at least about $10^7$ $M^{-1}$ and even more preferably $10^8$ $M^{-1}$ to $10^{10}$ $M^{-1}$. Determination of such affinity is preferably conducted under standard competitive binding immunoassay conditions which are common knowledge to one skilled in the art.

3. Methods of Treatment and Compositions

The SP1 and SP2 polypeptides, polynucleotides encoding same and antibodies of the invention may be used in many ways in the treatment and/or prevention of *Streptococcus suis*-associated diseases or infection caused by *S. suis*.

For instance, and according to an aspect of the invention, the SP1 and/or SP2 polypeptides of the invention may be used as immunogens for the production of specific antibodies for the treatment and/or prevention of *Streptococcus suis* infection. Suitable antibodies may be determined using appropriate screening methods, for example by measuring the ability of a particular antibody to passively protect against *Streptococcus suis* infection in a test model. Examples of an animal model are the mouse and pig models described in the examples herein.

According to another aspect, the polynucleotides encoding polypeptides of the invention or derivatives thereof may be used in a DNA immunization method. That is, they can be incorporated into a vector which is replicable and expressible upon injection thereby producing the antigenic polypeptide in vivo. For example polynucleotides may be incorporated into a plasmid vector under the control of the CMV promoter which is functional in eukaryotic cells. Preferably the vector is injected intramuscularly.

The use of a polynucleotide of the invention in genetic immunization will preferably employ a suitable delivery method or system such as direct injection of plasmid DNA into muscles [Wolf et al. H M G (1992) 1: 363, Turnes et al., Vaccine (1999), 17: 2089, Le et al., Vaccine (2000) 18: 1893, Alves et al., Vaccine (2001)19: 788], injection of plasmid DNA with or without adjuvants [Ulmer et al., Vaccine (1999) 18: 18, MacLaughlin et al., J. Control Release (1998) 56: 259, Hartikka et al., Gene Ther. (2000) 7: 1171-82, Benvenisty and Reshef, PNAS USA (1986) 83: 9551, Singh et al., PNAS USA (2000) 97: 811], targeting cells by delivery of DNA complexed with specific carriers [Wa et al., J Biol Chem (1989) 264: 16985, Chaplin et al., Infect. Immun. (1999) 67:6434], injection of plasmid complexed or encapsulated in various forms of liposomes [Ishii et al., AIDS Research and Human Retroviruses (1997) 13: 142, Perrie et al., Vaccine (2001) 19:3301], administration of DNA with different methods of bombardment [Tang et al., Nature (1992) 356: 152, Eisenbraun et al., DNA Cell Biol (1993) 12: 791, Chen et al., Vaccine (2001) 19:2908], and administration of DNA with lived vectors [Tubulekas et al., Gene (1997) 190: 191, Pushko et al., Virology (1997) 239: 389, Spreng et al. FEMS (2000) 27: 299, Dietrich et al., Vaccine (2001) 19: 2506].

A further aspect of the invention is the use of the antibodies directed to the polypeptides of the invention for passive immunization. One could use the antibodies described in the present application.

In this connection, another embodiment of the present invention relates to a composition for preventing or treating such diseases or infections. The composition of the present invention advantageously comprises an acceptable carrier and a SP1 and/or SP2 polypeptide(s) of the invention. Alternatively, the composition of the invention can comprise an antibody and/or a polynucleotide and/or an expression vector of the invention.

In a preferred embodiment, the composition of the invention further comprises an adjuvant. As used herein, the term "adjuvant" means a substance added to the composition of the invention to increase the composition's immunogenicity. The mechanism of how an adjuvant operates is not entirely known. Some adjuvants are believed to enhance the immune response (humoral and/or cellular response) by slowly releasing the antigen, while other adjuvants are strongly immunogenic in their own right and are believed to function synergistically. Known adjuvants include, but are not limited to, oil and water emulsions (for example, complete Freund's adjuvant and incomplete Freund's adjuvant), Corytzebactei-ium parvuin, Quil A, cytokines such as IL12, Emulsigen-Plus®, *Bacillus* Calmette Guerin, aluminum hydroxide, glucan, dextran sulfate, iron oxide, sodium alginate, Bacto Adjuvant, certain synthetic polymers such as poly amino acids and co-polymers of amino acids, saponin, paraffin oil, and muramyl dipeptide. Adjuvants also encompass genetic adjuvants such as immunomodulatory molecules encoded in a co-inoculated DNA, or as CpG oligonucleotides. The coinoculated DNA can be in the same plasmid construct as the plasmid immunogen or in a separate DNA vector.

Yet, a further embodiment of the present invention is to provide a method for treating and/or preventing a *Streptococcus suis*-associated disease or infection in an animal. The method of the invention comprises the step of administering to the animal a composition according to the invention.

Further agents can be added to the composition of the invention. For instance, the composition of the invention may also comprise agents such as drugs, immunostimulants (such as α-interferon, β-interferon, γ-interferon, granulocyte macrophage colony stimulator factor (GM-CSF), macrophage colony stimulator factor (M-CSF), and interleukin 2 (IL2)), antioxidants, surfactants, flavoring agents, volatile oils, buffering agents, dispersants, propellants, and preservatives. For preparing such compositions, methods well known in the art may be used.

The amount of the components or the elements of the composition of the invention is preferably a therapeutically effective amount. A therapeutically effective amount of the contemplated component is the amount necessary to allow the same to perform their immunological role without causing overly negative effects in the host to which the composition is administered. The exact amount of the components to be used and the composition to be administered will vary according to factors such as the type of condition being treated, the type and age of the animal to be treated, the mode of administration, as well as the other ingredients in the composition.

The composition of the invention may be given to an animal through various routes of administration. For instance, the composition may be administered in the form of sterile injectable preparations, such as sterile injectable aqueous or oleaginous suspensions. These suspensions may be formulated according to techniques known in the art using suitable dispersing or wetting agents and suspending agents. The sterile injectable preparations may also be sterile injectable solutions or suspensions in non-toxic parenterally-acceptable diluents or solvents. They may be given parenterally, for example intravenously, intramuscularly or sub-cutaneously by injection, by infusion or per os. Suitable dosages will vary, depending upon factors such as the amount of each of the components in the composition, the desired effect (short or long term), the route of administration, the age and the weight of the animal to be treated. Any other methods well known in the art may be used for administering the composition of the invention.

4. Methods of Detection or Diagnosis and Kits

The SP1 and/or SP2 polypeptides, polynucleotides encoding same and antibodies of the invention may also be used in different ways in the detection and diagnosis of *Streptococcus suis*-associated diseases or infections caused by *S. suis*.

In this connection and in a further embodiment, the present invention provides a method for detecting the presence or absence of a *Streptococcus suis* strain in a sample, comprising the steps of:

a) contacting the sample with an antibody of the invention as defined above for a time and under conditions sufficient to form a complex; and b) detecting the presence or absence of the complex formed in a).

As used herein, the term "sample" refers to a variety of sample types obtained from an animal and can be used in a diagnostic or detection assay. The definition encompasses blood and other liquid samples of biological origin, solid tissue samples such as a biopsy specimen or tissue culture or cells derived therefrom.

Yet, in another embodiment, the present invention provides a method for detecting the presence or absence of antibodies raised against a *Streptococcus* suis strain in a sample, comprising the steps of:
 a) contacting the sample with a polypeptide of the invention as defined above for a time and under conditions sufficient to form an immune complex; and
 b) detecting the presence or absence of the immune complex formed in a).

One skilled in the art will recognize that this diagnostic test may take several forms, including an immunological test such as an enzyme-linked immunosorbent assay (ELISA) or a radioimmunoassay, essentially to determine whether antibodies specific for the protein (such as SP1 and/or SP2) are present in an organism.

The present invention further provides kits for use within any of the above diagnostic methods. Such kits typically comprise two or more components necessary for performing a diagnostic assay. Components may be compounds, reagents, containers and/or equipment. For example, one container within a kit may contain an antibody or fragment thereof that specifically binds to a SP1 or SP2 polypeptide of the invention. One or more additional containers may enclose elements, such as reagents or buffers, to be used in the assay.

In this connection, the present invention also provides a diagnostic kit for the detection of the presence or absence of antibodies indicative of *Streptococcus* suis strain, comprising:
 a SP1 and/or SP2 polypeptide according to the invention;
 a reagent to detect polypeptide-antibody immune complex;
 a biological reference sample lacking antibodies that immunologically bind with said peptide; and
 a comparison sample comprising antibodies which can specifically bind to said peptide;
wherein said polypeptide, reagent, biological reference sample, and comparison sample are present in an amount sufficient to perform said detection.

Another diagnostic kit preferably contemplated is a kit for the detection of the presence or absence of polypeptides indicative of *Streptococcus* suis strain, comprising:
 an antibody according to the invention;
 a reagent to detect polypeptide-antibody immune complex;
 a biological reference sample polypeptides that immunologically bind with said antibody; and
 a comparison sample comprising polypeptides which can specifically bind to said peptide;
wherein said antibody, reagent, biological reference sample, and comparison sample are present in an amount sufficient to perform said detection.

EXAMPLES

The present invention will be more readily understood by referring to the following examples. These examples are illustrative of the wide range of applicability of the present invention and are not intended to limit its scope. Modifications and variations can be made therein without departing from the spirit and scope of the invention. Although any methods and materials similar or equivalent to those described herein can be used in the practice for testing of the present invention, preferred methods and materials are described hereinafter.

Example 1

Identification of a Surface Protein of *Streptococcus suis* and Evaluation of its Immunogenic and Protective Capacity in Pigs A new *Streptococcus suis* surface protein reacting with a convalescent serum from pigs clinically infected by *S. suis* type 2 was identified. The apparent 110 kDa protein designated SP1 exhibits typical features of membrane-anchored surface proteins of Gram-positive bacteria such as a signal sequence and a LPVTG (SEQ ID NO:10) membrane anchor motif. Moreover, a conserved avirulence domain that often found in plant pathogens has been detected. Electron microscopy using a SP1-specific antiserum has confirmed the surface location of SP1 protein on *S. suis*. The SP1-specific antibody reacts with the cell lysates of most *S. suis* serotypes and type 2 isolates in immunoblots, demonstrating its high conservation in *S. suis* species. Immunization of piglets with the recombinant SP1 by intramuscular route elicits a significant total immunoglobulin G (IgG) antibody response. However, the antibody response is not reflected in protection of pigs that are intratracheally challenged with a virulent strain in our conventional vaccination model.

Materials and Methods

Bacterial strains, phage, plasmids and media. Reference strain S735 of *S. suis* serotype 2 was used for the genomic library construction. Reference strains of the thirty-three serotypes (types 1 to 31, 33 and 1/2), 26 field strains of serotype 2 from different origin as well as five other Gram-positive organisms are listed in Table 1. Phage Lambda Zap II and *Escherichia coli* XL1-Blue MRF strain were obtained from a commercial source (Stratagene, La Jolla, Calif.). *S. suis* were grown in Todd-Hewitt broth (THB, Difco, Detroit, Mich.) or agar plates (Quelab Laboratories, Montreal, Canada) at 37° C. with 5% of $CO_2$, while other Gram-positive bacteria were grown as recommended by the ATCC catalogue. *E. coli* was grown in either Luria-Bertani (LB) medium alone or LB medium supplemented with 2 g of maltose/liter at 37° C. Where appropriate, *E. coli* was grown in the presence of 50 μg of ampicillin/ml and 0.8 mM isopropyl-β-D-thiogalactopyranoside (IPTG). pMal™-p vector (New England BioLabs) was used for generating the MBP-SP1 fusion protein.

Antisera. Convalescent swine sera were collected from pigs clinically infected with *S. suis* type 2 strain S735. Monospecific anti-SP1 serum was obtained by immunizing New Zealand White rabbits intravenously with 230 μg of purified SP1 emulsified with 0.5 ml of Freud's incomplete adjuvant. The rabbits received two booster injections with the same dose of the SP1 at 2-week intervals and then were bled 10 days after the last booster immunization. Sera were stored at −20° C. until used.

Identification, cloning, and sequencing of the sp1 gene. Chromosomal DNA from *S. suis* S735 strain was isolated as previously described (33). Purified chromosomal DNA was partially digested with the restriction enzyme EcoRI, and the resulting fragments were electrophoresed in 1% agarose gel. Fragments in the 6- to 10-kb size range were extracted from the gel and ligated to the EcoRI arms of λZAPII vector, and the vector was encapsidated using the Gigapack II packaging extract (Stratagene). The recombinant phages were used to infect *E. coli* XL1-Blue MRF', which was then plated onto LB agar. The resulting plaques were lifted onto nitrocellulose membranes (Bio-Rad, Mississauga, Ontario, Canada). The membranes were blocked using Tris-saline buffer (TBS) with 2% skim milk and sequentially incubated with the convalescent swine serum from *S. suis* serotype 2 infection, peroxidase-conjugated rabbit anti-swine immunoglobulin G (IgG) antisera (Jackson Immuno Research Laboratories, Inc., West Grove, Pa.), and O-phenylenediamine. The positive plaques were purified to homogeneity. The recombinant pBluescript plasmids were excised with ExAssist helper phage (Stratagene) according to the manufacturer's instructions. The sequence of the insert was determined using T3 and T7 promoters as primers in DNA Sequencing Facility, University of Maine (Orono, Me., USA). The nucleotide and amino acid sequences deduced from open reading frames (ORFs) were analyzed using programs available on the internet.

The sequence coding for mature SP1 was amplified from purified chromosomal DNA of strain S735 by PCR primers P1 (5'-ATGGATCCATTGAAGGCCGCTCGGCA-CAAGAAGTAAAA-3'; SEQ ID NO 13) and P2 (5'-CCAAGTCGACTTATAATTTACGTTTACGTGTA-3'; SEQ ID NO 14), which contained BamHI and Sal I restriction sites, respectively. The PCR was performed with 5 min at 94° C., followed by 30 cycles of 1 min at 94° C., 30 s at 56° C., and 1 min at 72° C. The resulting PCR fragment was cloned into Bam HI and Sal I sites of pMAL-p expression vector. The recombinant plasmid containing the sp1 gene was named pORF3.

Expression and purification of recombinant SP1 protein. The purified plasmid pORF3 was used to transform *E. coli* XL1-Blue strain by electroporation with Genepulse II apparatus (Bio-Rad) following the manufacturer's recommendations. This recombinant strain was grown in LB medium plus 2 g of glucose/L and 50 µg of ampicillin/ml. For over-expression, the culture was inoculated from an overnight culture with its starting $OD_{600}$ adjusted to 0.1. The culture was incubated with agitation until $OD_{600}$ of approximately 0.8, and then IPTG was added in order to induce production of the MBP-SP1 fusion protein. After 2 hours of the induction, the fusion protein was found in the bacterial periplasm as well as in the cytoplasm. It was decided to use extracts of the bacterial lysates for purification of the SP1 protein.

The fusion protein was purified by affinity chromatography using an amylose resin (New England BioLabs) following the manufacturer's instructions. The *E. coli* cell pellet was suspended in the affinity column binding buffer (20 mM Tris-HCl, 50 mM NaCl, pH 7.4) and cells were lysed using the French Pressure Cell Press (SLM Instruments, Inc.). After filtration with a 0.45 µm membrane, the supernatant was subjected to the amylose resin. The MBP-SP1 fusion protein was eluted with 1% maltose in the binding buffer and protein-containing fractions were determined by sodium dodecyl sulfate-polyacrylamide gel electrophoresis (SDS-PAGE). The purified fusion protein was cleaved with protease Factor Xa (New England BioLabs) at a concentration of 20 µg/mg protein, and applied to a mono-Q column (Amersham Pharmacia Biotech, Baie d'Urfee, Canada). The recombinant SP1 devoid of MBP carrier was eluted from the column by using a linear NaCl gradient (0 to 0.4 M NaCl in 20 mM Tris-HCl, pH 7.4). The SP1-containing fractions were combined and dialyzed against PBS buffer. The purity of the recombinant SP1 was evaluated by SDS-PAGE, and the concentration of the protein was determined by the Bradford protein assay (Bio-Rad) according to the manufacturer's instructions.

SDS-PAGE and western immunoblotting. SDS-PAGE was performed as described by Laemmli (21). Total cell extract or purified protein was separated on a 10% acrylamide gel and the gel was then stained with Coomassie brilliant blue R250 (Sigma, St. Louis, Mo.). Prestained low molecular mass markers (Bio-Rad) were used to determine the apparent molecular weights of proteins. Alternatively, Western blotting of proteins transferred to nitrocellulose membranes was performed essentially as described by Burnette (5).

Immunoelectron microscopy. *S. suis* S735 strain was grown in 5 ml of THB overnight, centrifuged, and resuspended in 500 µl of PBS (pH8.0). 20 µl of the bacterial suspension was placed on nickel-formvar grids (INRS, Institut Armand Frappier, Laval, Canada) and allowed to partially air dry. After blocking for 30 min with 10% normal donkey serum in dilution buffer (PBS-1% bovine albumin-1% Tween 20, pH8.0), the grids were soaked in 50 µl of SP1-specific rabbit serum or control rabbit anti-MBP serum (New England BioLabs) diluted 1/25 in the dilution buffer for 2 h at room temperature. The grids were washed three times in PBS-1% Tween20, and then transferred into 50 µl of 12 nm colloidal gold-affinipure donkey anti-rabbit IgG (Jackson ImmunoResearch Laboratories) diluted 1/30 in the dilution buffer and incubated for 1 h at room temperature. After three washes with PBS-1% tween20 and one wash with distilled water, bacteria were stained with 1% phosphotungstic acid and examined with an electron microscope (Philips 201) at an accelerating voltage of 60 kV.

Immunization and protection study. Pigs were used to perform the immunization and protection assay at VIDO (Saskatoon, Canada) in accordance with principles outlined in the "guide to the care and use of experimental animals" of the Canadian Council on Animal Care using a protocol that was approved by the University Committee on Animal Care (37). Three week-old piglets with average weight of 8.23 kg from a herd that is free of *S. suis* serotype 2 were randomly assigned to two groups of eight. The pigs were injected intramuscularly twice at a 3-week interval with 1 ml of either 100 µg purified SP1 mixed with 30% Emulsigen-Plus (MVP Laboratories, Ralston, Nebr.) adjuvant or 30% Emulsigen-Plus in physiological saline as a control. Eleven days after the second injection, the immunized and control animals were challenged by aerosol of 1 ml ($4.6 \times 10^6$ CFU) of a log-phase culture of *S. suis* virulent strain 166, which has been confirmed to be highly virulent (3). Blood samples were collected prior to each injection, challenge and the end of the experiment for determination of antibody responses. Pigs were monitored daily for clinical signs, body temperature and mortality for ten days after challenge. All pigs were examined postmortem for gross pathology and blood was cultured to detect the presence of *S. suis* bacteremia.

ELISA. Serum SP1-specific total IgG and IgG isotypes (IgG1 and IgG2) of immunized piglets were determined by enzyme-linked immunosorbent assay (ELISA). Polysorb plates (Nunc-Immunoplates, Rochester, N.Y., USA) were coated overnight at 4° C. with 100 µl per well of the purified recombinant SP1 at a concentration of 0.3 µg/ml in carbonate buffer. After three washes with PBS containing 0.05% Tween20 (PBST), the plates were blocked with 5% skim milk in PBST for 1 h at 37° C. For determination of total IgG, swine sera from the control and vaccine groups were diluted 1/5000 in PBST and added to appropriate wells in duplicate at 100 µl per well. After incubation for 1 h at 37° C. and washing three times, bound antibodies were detected by incubation for 1 h at 37° C. with peroxidase-conjugated goat anti-swine IgG(H+L) antisera (Jackson Immuno Research Laboratories). For IgG1 and IgG2 detection, 1/500 diluted swine sera from vaccine group were added at 100 µl per well. Mouse anti-porcine IgG1 or IgG2 (Serotec, Kidlington, Oxford, UK) was used as the primary antibody, and peroxidase-conjugated goat anti-mouse IgG(H+L) (Serotec) was used as the secondary antibody. The plates were developed with TMB substrate (Zymed, S. San Francisco, USA). Absorbance was measured at 450 nm in an ELISA reader (Power Wave 340, Bio-Tek Instruments, Inc.). Results were expressed as the means±S.D. Statistical significance was determined by Student's t test.

Nucleotide sequence accession number. The sequence of the gene encoding SP1 protein of *S. suis* is shown in FIG. 2 and has been assigned GenBank accession number AY864331.

Results

Identification of sp1 gene. The *S. suis* chromosomal library was constructed from the *S. suis* S735 strain in λZAPII and screened using convalescent swine sera from *S. suis* serotype 2 infected animals. One clone, which expressed a protein with an apparent molecular weight (MW) of 110 kDa that was strongly reactive against the convalescent swine serum, was selected for further characterization. The recombinant pBluescript plasmid, designated pSS735, was excised from the bacteriophage arms, and its schematic organization is presented in FIG. 1. DNA sequence analysis of the 6057-bp insert of the pSS735 revealed four ORFs. This gene cluster was found in the partially sequenced genomes of *S. suis* Canadian strain 89/1591 (NZ_AAFA00000000) and European strain P1/7 (NC_004549) with the same organization. The deduced amino acid sequences of both ORF1 and ORF2 showed identities ranging from 50-80% with a glycosyl transferase, and ORF4 showed identities ranging from 50-75% with a catabolite control protein A from many bacterial species, most of them belong to the genus *Streptococcus*. The ORF3 encodes a 670 amino acid protein, designed SP1, with a predicted pI of 6.0 and a calculated molecular mass of 74.8 kDa. Comparison of the amino acid sequence of SP1 with those in available databases revealed no significant homology with other proteins. Subcloning analysis of the sp1 sequence in pMal-p vector revealed that the SP1 strongly reacted with the convalescent swine serum, demonstrating that SP1 is the immunogenic protein.

SP1 is a novel C-terminal-anchored surface protein of *S. suis*. The 2010 bp of sp1 gene starts with an ATG codon which is preceded by putative Shine-Dalgarno sequence (GAAAGGA) 10 bp upstream of the start codon and terminates with a TAA codon (FIG. 2). Analysis of the predicted SP1 amino acid sequence revealed a hydrophobic core of 15 amino acids at the N-terminus and a putative signal-peptidase cleavage site between $Ala^{29}$ and $Gln^{30}$. Ten repeats of 27-amino-acid sequence with a strong consensus pattern, separated by 3-amino-acid residue spacers, were detected within the carboxyl half of the protein. Immediately C-terminal from the repeat region is a cell wall-associated region, which spans 49-amino-acid residues and is characterized by a high percentage of threonine residues (20.4%). This threonine-rich region is immediately followed by an LPVTG (SEQ ID NO:10) consensus motif typical of membrane-anchored surface proteins of many Gram-positive bacteria. Beginning four amino acids C-terminal from the membrane anchor motif, a second hydrophobic segment of 16 amino acids was identified, which is followed by four positive charged amino acid residues at the C-terminal end of the protein (FIG. 2).

Analysis of the amino acid composition revealed a region of absence of aromatic residues between $Glu^{272}$ and $Thr^{630}$, which spans all of the repeat sequences. Furthermore, a conserved domain search using BLAST identified an avirulence domain in $Lys^{319}$ to $Val^{601}$ region, which exhibits similarity with AvrXa7 avirulence factor from the plant pathogen *Xanthomonas oryzae* pv. *oryzae* (41) with 20% identity (FIG. 3). If conservative amino acid substitutions are taken into consideration, the similarity is 48%.

Production of the recombinant SP1. The sequence coding for mature SP1 protein was amplified by PCR and ligated into the IPTG-inducible pMAL-p vector. The resulting recombinant plasmid was expressed in *E. coli* XL1-Blue strain. As shown in FIG. 4A, induction of the *E. coli* recombinants harboring the malE-sp1 fusion gene led to the expression of an approximately 150 kDa of MBP-SP1 fusion protein (lane 2) which was absent in the non-induced *E. coli* cells (lane 1). The fusion protein was mostly found in the cytoplasm of the *E. coli* cells (lane 3). Interestingly, a truncated MBP-SP1 fusion protein in which the repeating region characterized by absence of aromatic substitutions was deleted was completely transported into the periplasmic space (data not shown), suggesting that this region somehow interfered with MBP localization.

The fusion protein was purified by using affinity matrix amylose column and eluting with maltose, and showed a single protein band of approximate 150 kDa on SDS-PAGE (lane 4). The purified fusion protein was proteolytically cleaved with Factor Xa, yielding the apparent 110 kDa of mature SP1 and the expected 45 kDa of MBP tag (lane 5). The mature SP1 devoid of MBP was obtained by subsequent purification with ion-exchange chromatography, with a purity>95% estimated by SDS-PAGE (lane 6). Both the MBP-SP1 fusion protein and the purified recombinant SP1 demonstrated specific reactivity in a western blot to the convalescent swine serum used for the initial screening of the genomic library (FIG. 4B). Identity of the purified SP1 was confirmed by N-terminal protein sequencing. The protein concentration was measured with Bradford protein assay and adjusted to 1 mg/ml.

Figure 5:
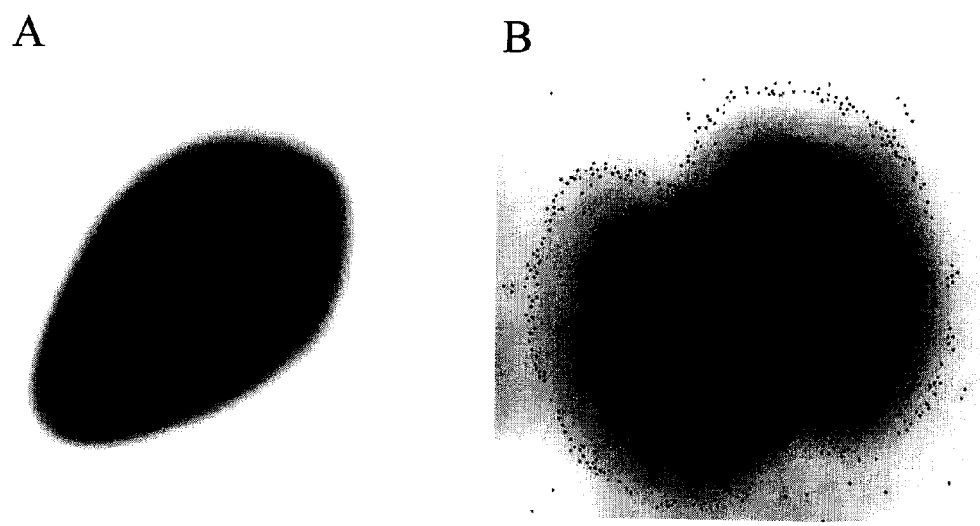
FIG. 5: Immunoelectron microscopy of *S. suis* (4500×). The surface location of SP1 on *S. suis* is demonstrated using a monospecific SP1 antiserum and a gold-conjugated secondary antibody (B). No labeling was found in the control bacterial cell (A). Bars, 200 nm.

Cell surface expression of SP1 in *S. suis*. To confirm the location of SP1 on the surface of *S. suis* cells, immunoelectron microscopy was conducted by using a monospecific polyclonal anti-SP1 antibody, R44. Immunogold particles were found to be evenly distributed on the surface of the *S. suis* S735 strain. This indicates that SP1 protein is homogeneously expressed on the cellular surface. Rabbit anti-MBP serum was used as control and did not show any labeling (FIG. 5).

Distribution of the SP1 among *S. suis*. To evaluate the conservation of SP1 among reference strains of deferent serotypes of *S. suis* and serotype 2 field strains, whole cell preparations of the bacteria were applied to western blots and detected by SP-specific antibody R44. As shown in Table 1, except for strains of serotypes 13, 16, 20, 22 and 24, R44 reacted with other 28 *S. suis* serotypes, while 25 of 26 tested type 2 isolates from different geographic origins reacted with the R44 antibody. Five strains from other species of Streptococci were used to verify the specificity of SP1 and no SP1 protein were detected.

Figure 6:
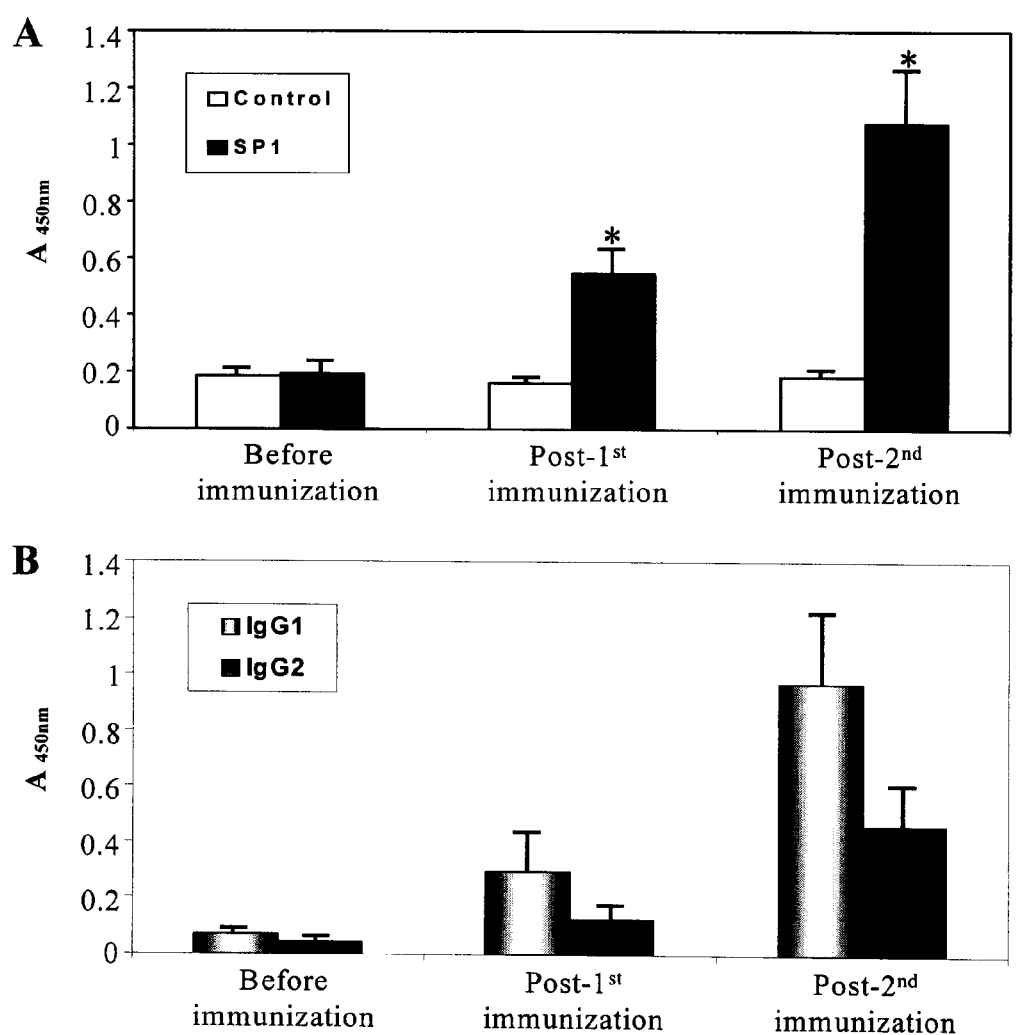
FIG. 6: Antibody responses after vaccination with the SP1 in piglets. (A) Total SP1-specific IgG in sera was measured by ELISA, showing that single injection of SP1 elicited a significant IgG response that was obviously enhanced by the booster. (B) ELISA for serum IgG isotypes in SP1 immunized pigs showed that IgG1 levels were consistently higher than IgG2 levels. The results are expressed as the means of absorbances and standard errors. *: $p \leq 0.05$.
Figure 7:
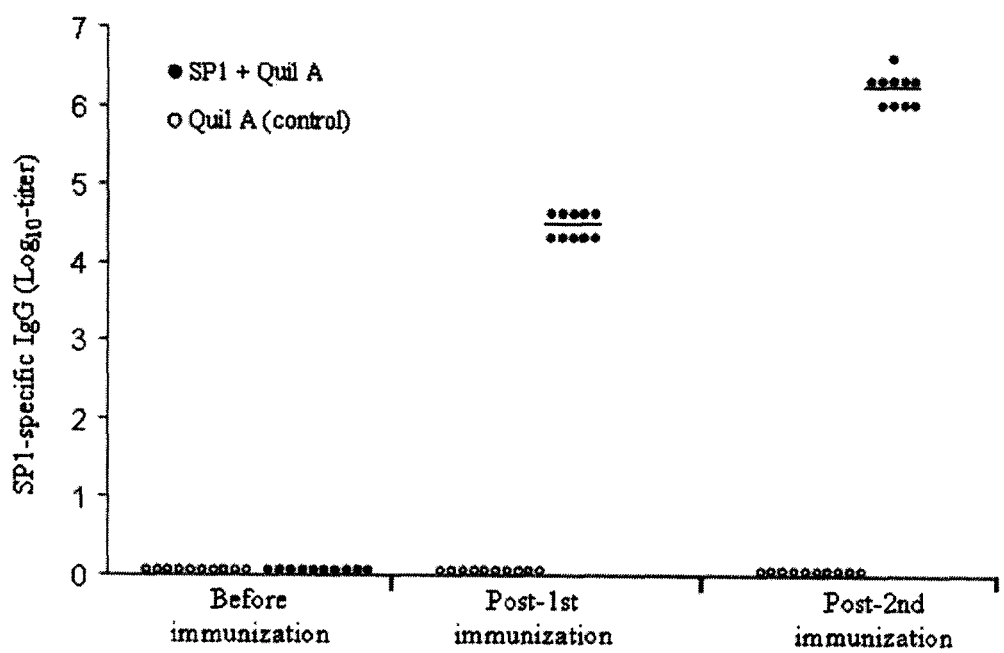
FIG. 7: SP1-specific total humoral IgG titres in mice immunized with Quil A and Quil A plus SP1.
Figure 8:
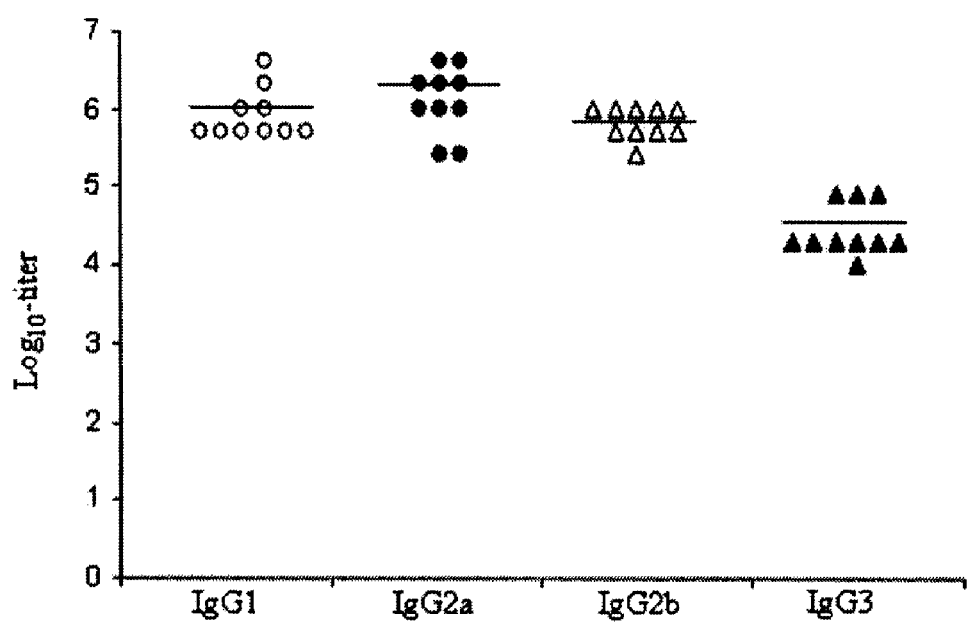
FIG. 8: IgG subclasses in sera from mice immunized with recombinant SP1.
Figure 9:
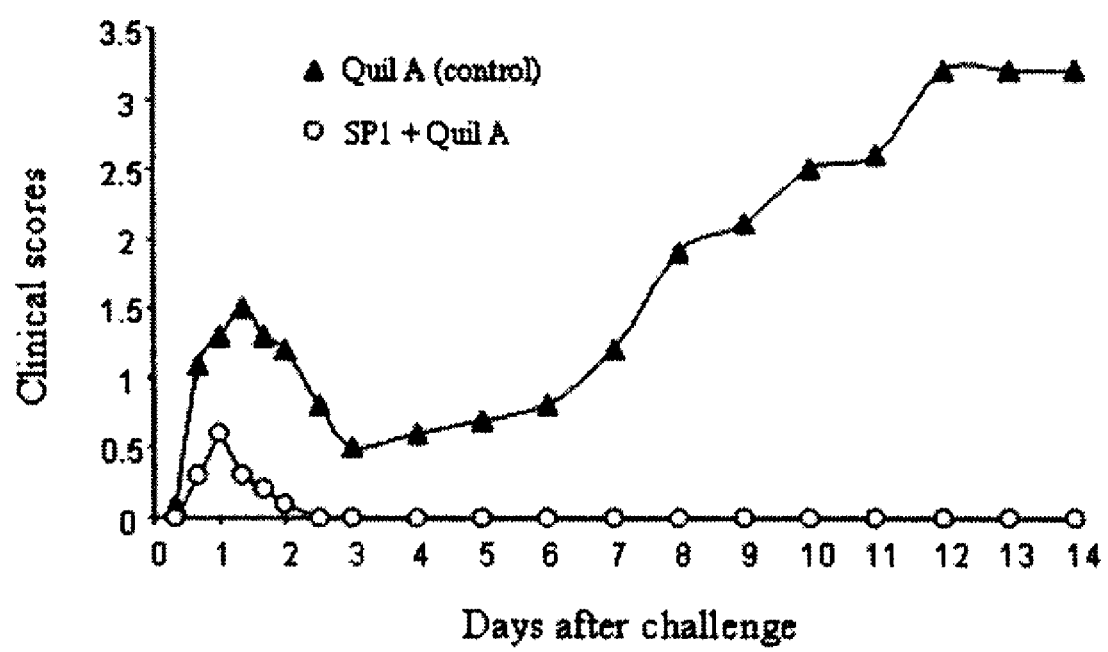
FIG. 9: Vaccination with recombinant SP1 protects mice against *S. suis* challenge infection.
Figure 10:
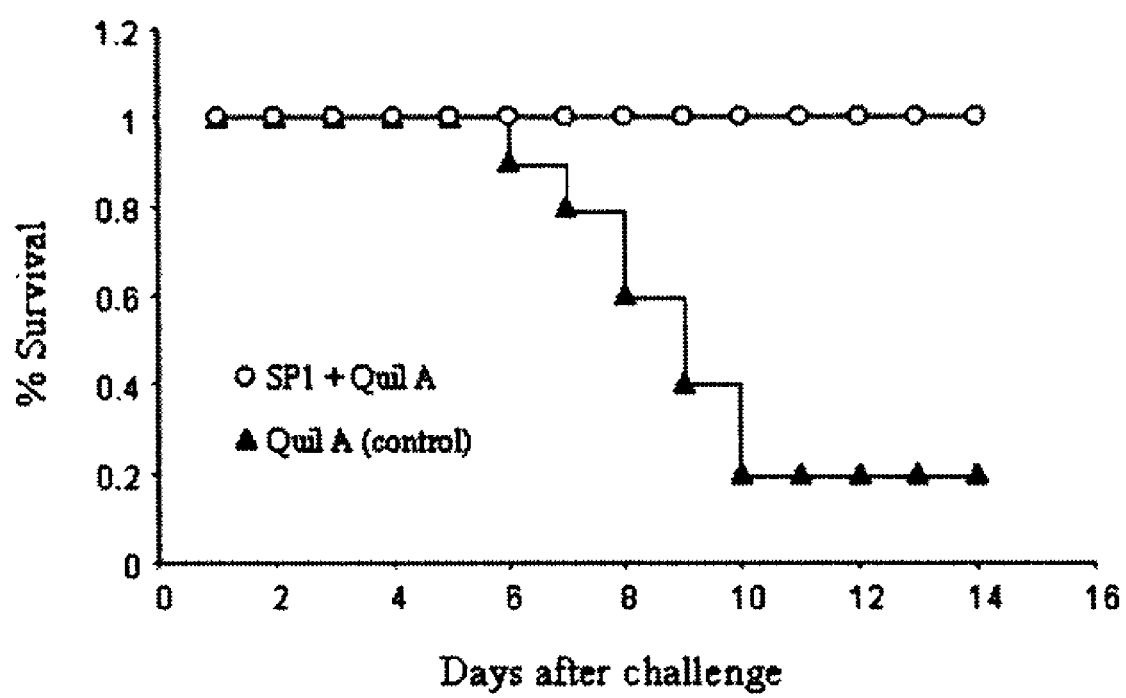
FIG. 10: Vaccination with recombinant SP1 protects mice from *S. suis* death.

Immunogenicity of SP1 and protection of pigs against challenge with *S. suis*. Groups of 8 piglets were immunized twice intramuscularly with either 100 μg of purified recombinant SP1 emulsified with the adjuvant or adjuvant only. Immunization of pigs with SP1 triggered an antigen-specific response (FIG. 6A). Analysis of corresponding sera obtained from the control animals and the animals before immunization clearly indicated that there was no SP1-specific antibody, since only background ELISA values were recorded. Only two weeks after the first injection, SP1 elicited a significant IgG response that was obviously enhanced by the boost immunization. Assessment of IgG isotypes demonstrated that sera from immunized pigs contained both IgG1 and IgG2 antibodies (FIG. 6B). However, IgG1 response dominated over IgG2, suggesting that vaccination with SP1 mainly induced the Th2-like immune response. Aerosol challenge of the pigs with *S. suis* 166 strain resulted in steady increases of clinical score starting from day 2 after the challenge and there was no significant effect of the vaccination. As summarized in Table 2, although fewer pigs suffered arthritis in the vaccinated group than in the control group, both groups showed similar symptoms after challenge. Three pigs from each group died or were euthanized due to high clinical scores prior to the end of the experiment. *S. suis* bacteremia was found in all dead pigs and was not detected in the surviving pigs.

Discussion

First immunization of pigs elicited rapid SP1-specific humoral antibody response that can be significantly boosted by a subsequent injection. However, the antibody to SP1 did not confer immunity against an heterologous challenge using *S. suis* strain 166. This discrepancy between antibody response and protection have been reported in some other surface antigens of Gram-positive bacteria, such as streptococcal fibronectin binding protein (Sfb1) (26), pneumococcal surface protein A (PspA) (27), group B polysaccharide (25) and M-like protein (SeM) of *Streptococcus equi* (34). The reason why antibodies against SP1 were not protective against the challenge by *S. suis* 166 is unclear. In a phagocytic killing study, presence of pooled serum from the SP1-immunized pigs did not promote *S. suis* killing by porcine neutrophils, suggesting that the antibodies are lacking opsonophagocytic function. Host protection against infection caused by *S. suis*, a highly encapsulated microorganism, is mediated primarily by phagocytosis (32). Therefore, total IgG levels generated in the Applicant's conventional vaccination model may not adequately reflect the presence of protective antibodies that are capable of triggering leukocyte effector functions. To further illustrate the immune response types trigged by SP1, IgG isotypes in immunized sera were assessed. IgG1 levels were consistently higher then IgG2 levels suggesting the induction of Th2-like responses. Although the concept of "Th1/Th2" balance is not yet well documented in pigs as in some other species, recent evidence showed that porcine IgG2 had greater complement activating ability than did IgG1 (6).

Emulsigen-Plus was used as an adjuvant in this study, because it was believed to be capable of creating an antigen depot at the site of inoculation from which the antigen is slowly released and thus providing prolonged stimulation to the immune system (23, 37). However, recent evidence showed that vaccine formulated with Emulsigen alone triggered predominantly an IgG1 response but very weak Th1-type immune response (19, 28). Evidence from vaccination using surface antigens of other Gram-positive bacteria has demonstrated that efficiency of opsonophagocytosis can be dramatically enhanced by using Th1-directing adjuvants, such as CpG and interleukin-12 (IL-12) (4, 22, 24). These adjuvants promote a Th1-type immune response characterized by enhanced production of opsonizing antibodies, specially IgG2 isotype. Furthermore, the enhanced antibody-mediated opsonization was clearly reflected in protection (2, 40).

In conclusion, SP1 is a novel C-terminal-anchored surface protein of *S. suis*, as demonstrated by analysis of the molecular features and electron microscopy. Vaccination with the recombinant SP1 elicited significant humoral antibody response in piglets, along with the fact that convalescent swine sera present high titers of antibody against this protein, suggesting that SP1 is an exposed antigen of *S. suis*. Taken together with its wide distribution in different *S. suis* serotypes, these findings made the SP1 a candidate for consideration in the development of a subunit vaccine. The potential of SP1 as a vaccine candidate will be demonstrated in the following Examples.

Example 2

Recombinant SP1 Protects Mice Against *S. suis* Challenge Infection

This study is to evaluate whether the SP1 recombinant protein is protective as a subunit vaccine candidate in a mouse model with a modified immunization route and adjuvant.

EXPERIMENTAL PROCEDURE: Mice (CD1) were randomly assigned to two groups of ten, and immunized subcutaneously twice at 2-week interval with either 20 µg of purified SP1 mixed with 20 µg of Quil A as a adjuvant or 20 µg of Quil A only as a control (Table 1). Ten days after the second vaccination, the animals were challenged i.p. with $1 \times 10^8$ CFU of a *S. suis* virulent strain (31533). The mice were monitored twice a day for clinical signs and mortality until day 14 after the infection. Blood samples were collected prior to each vaccination and challenge for determining antibody responses.

RESULTS: Vaccination with SP1 elicited significant humoral IgG responses in mice after primary immunization (mean titre $3 \times 10^4$) and a booster injection significantly increased the antibody titre ($1.8 \times 10^6$). In contrast, the SP1-specific IgG in sera of control group was at undetectable level (FIG. 1). Furthermore, all of four IgG subclasses were induced in SP1-immunized mice, with the IgG2a titre being the highest ($1.75 \times 10^6$) followed by IgG1 ($1.2 \times 10^6$), IgG2b ($7.25 \times 10^5$) and IgG3 ($3.7 \times 10^4$) (FIG. 2). Specificity of SP1-induced antibodies was demonstrated by Western blot in which pooled sera collected from SP1-immunized mice can recognize the purified SP1 and the SP1 protein in *S. suis* S735 and 31533 cell preparations.

Sixteen hours after administering the challenge infection, all mice in control group started to exhibit clinical signs (septicemia), such as the ruffled hair coat (suggesting fever) and slow response to stimuli. Starting from day 4 after the challenge, 8 of 10 mice in this group successively developed severe central nervous system symptoms (meningitis) such as running in circles and opisthotonos. All of the 8 ill mice died, or had to be euthanized due to the severity of the condition. In contrast, except for 6 of 10 mice in SP1-vaccinated group had transient clinical signs such as slight rough hair and reluctant to move during 16-40 hours after the challenge, all mice in this group remained healthy during the observation period (FIGS. 3 and 4).

DISCUSSION AND CONCLUSION: The difference in protection observed in mouse and pig models is explained by well-balanced IgG subclass levels evoked in the mouse vaccination model, especially the extremely high IgG2a titre. Among murine antibody isotypes, IgG2a has been shown to be the most effective at activating opsonophagocytic function of leukocytes (2, 42, 43)). Furthermore, *S. suis*, an encapsulated bacterial, is most effectively eliminated by opsonophagocytosis. Thus, it is likely that predominant IgG2 production contributed most to the observed protection. Nevertheless, these data indicate that immunization of mice with SP1 by using a Th1 inducing adjuvant, such as Quil A, can induce an efficient antigen-specific response, and protect mice against challenge infection with a lethal dose of a virulent *S. suis* strain and result in complete protection from *S. suis* death (FIG. 4).

Example 3

Identification of a Novel Gene Encoding a *Streptococcus suis* Protein with IgG-Binding Activity and Protective Capacity In the Applicant's continued effort to understand the pathogenic mechanism of *S. suis* and search for its protein(s) that may be useful in the development of a reliable diagnostic reagent or vaccine, a new protein which exhibits IgG-binding activity was identified from a virulent strain of *S. suis* serotype 2. This apparent 58-kDa protein designed SP2 contains a 23 amino acids cleavable N-terminal signal sequence and a lysine M motif near the N-terminus, and six identical repeats of 13 amino acids each within the C-terminal part. SP2 is highly conserved among different *S. suis* serotypes as demonstrated by PCR amplification of the SP2 gene. Recombinant SP2 strongly reacted with a convalescent swine serum collected from pigs clinically infected by *S. suis* type 2. Immunization of mice with the purified recombinant SP2 elicits a significant antibody response that conferred a partial protection against challenge infection with a virulent *S. suis* strain.

These results show that SP2 is a potential diagnostic agent and vaccine candidate for *S. suis* infection.

Experimental Procedures and Results

Identification of SP2 Gene

Figure 12:
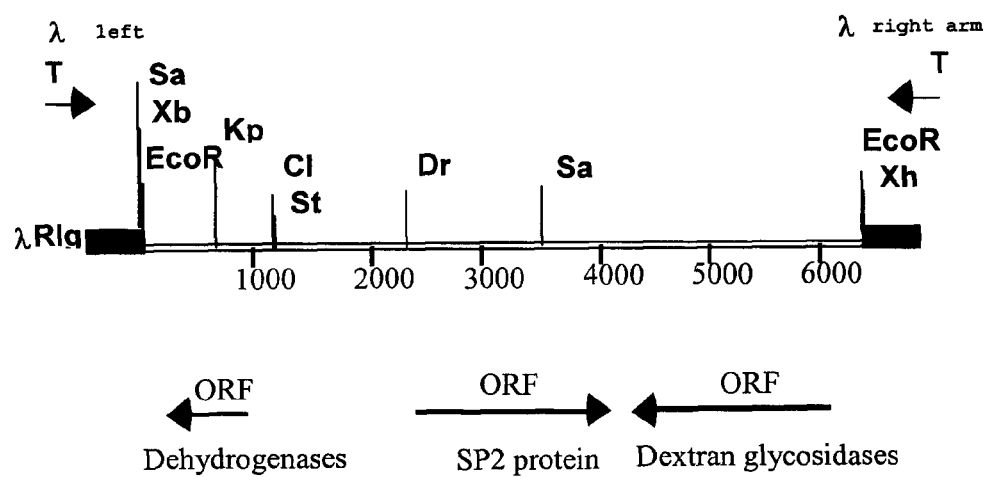
FIG. 12: Schematic representation and partial restriction map of the 6.3 kb insert of recombinant phage. Numbers indicate the distance (in base pairs) from the 5' end.

A positive phage which reacted by non immune mechanism with different classes and species of Ig (Pig IgG, Human IgG and IgA) was identified by screening the constructed *S. suis* serotype 2 genomic library. Sequence of the DNA insert revealed a 6.3 kb insert which contains three ORFs coding for dehydrogenases, SP2 and dextran glycosidases (44), respectively (FIG. 12). This gene cluster was found in the partially sequenced genomes of *S. suis* Canadian strain 89/1591 (NZ_AAFA00000000) and European strain P1/7 (NC_004549) with the same organization. The SP2 amino acid sequence presented similarities with some streptococcal proteins usually exhibiting Ig-binding activity. An identity of 45% in a 395-amino acid stretch was observed with a Conserved hypothetical protein of *Streptococcus pneumoniae* (AAL00677). Other homologies were found with a putative 42 kDa protein of *Streptococcus pyogenes* (45% identity over 388-amino acid stretch) (AAK33481) and with a group B streptococcal surface immunogenic protein (40% identity over 434-amino acid stretch) (60) (AAG 18474).

Characterization of SP2 Protein

The 1158 bp SP2 gene encodes a 386-aa SP2 protein, with a theoretical pI of 4.40 and molecular mass of 42.5 kDa. This protein was rich in valine (15%), glutamic acid (10%), and alanine (9%). Charge distribution analysis of SP2 revealed one positive charge cluster ($K^2$-$K^{26}$) at the N-terminus and one negative charge cluster ($D^{168}$-$E^{242}$) in middle of the protein (FIG. 13). The positive charge cluster was followed by a putative signal sequence of 23 amino acids. The amino acid sequence of SP2 contains a LysM (lysine) motif at positions 71 through 109. This LysM domain is found in a variety of enzymes involved in bacterial cell wall degradation and has a general peptidoglycan binding function, suggesting that SP2 may be a surface protein of *S. suis*. Thus, the N-terminal constitution of SP2 outlined a possibility that the positive charge cluster remained in the cytoplasm functions as a temporary stop and helps in formation of mature SP2 by cleaving the signal sequence and in location of SP2 on the bacterial surface via binding of LysM domain to peptidoglycan. Furthermore, six identical repeating sequences of 13 amino acids were identified in the middle part of SP2 (FIG. 13).

Distribution of SP2 Gene in Different *S. suis* Serotypes

To evaluate the conservation level of SP2, PCR were performed using primers covering the full-length SP2 gene. PCR was performed with an initial denaturing at 94° C. for 5 min followed by 30-cycles of 1 min at 94° C., 1 min at 52° C. and 2 min at 72° C., and a final elongation period of 10 min at 72° C.

The forward and reverse primers used for SP2 distribution in different serotypes were respectively:

(5'-TTTAAAAGAACGGTTGAAGGC-3'; SEQ ID NO: 15)
and

5'-GCATAAGCTGCCACTTGATCT-3'; SEQ ID NO: 16).

Figure 14:
FIG. 14: Distribution of SP2 gene in different *S. suis* serotypes. The SP2 genes were amplified by PCR from 31 of the 33 *S. suis* serotype reference strains.

SP2 gene was amplified from 31 of the 33 serotype reference strains with some size variations (FIG. 14). Sequence analysis of selected variant fragments suggested that the number of repeats in the SP2 gene is responsible for the size variations.

Production and Purification of Recombinant SP2

The gene coding for mature SP2 was generated by PCR from *S. suis* S735 chromosome and subcloned to a pET32+ vector (New England BioLabs). The construct was used to transform *E. coli* DE3 strain by electroporation with Genepulse II apparatus (Bio-Rad) following the manufacturer's recommendations. For over-expression, the culture was inoculated from an overnight culture with its starting $OD_{600}$ adjusted to 0.1. The culture was incubated with agitation until $OD_{600}$ of approximately 0.8, and then IPTG (0.5 mM) was added in order to induce production of the Trx-His-SP2 fusion protein. After 2 hours of the induction, bacterial cytoplasm were prepared and used for purification of the SP2 protein.

Figure 15:
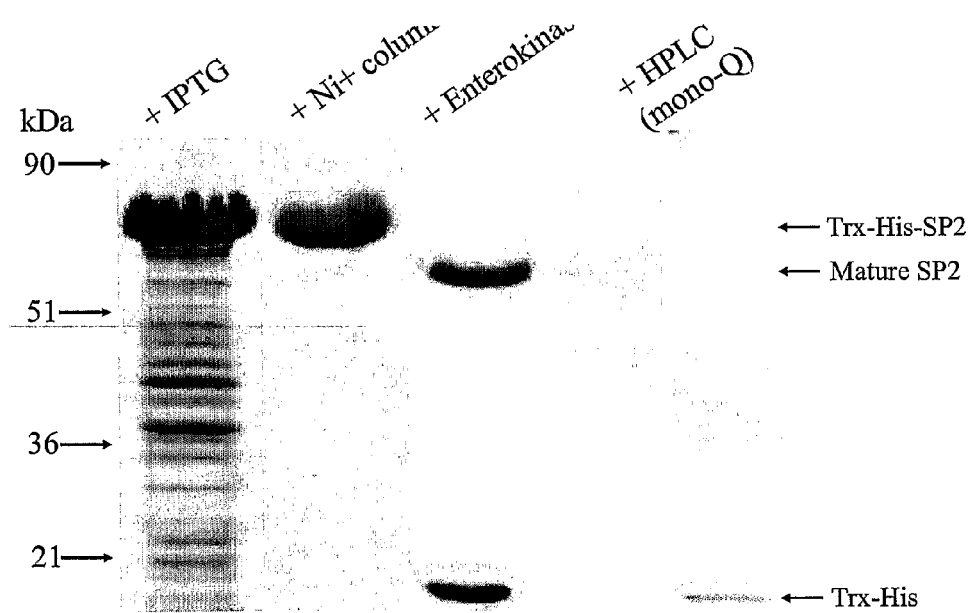
FIG. 15: Expression of Trx-His-SP2 fusion protein in *E. coli* and purification of the recombinant mature SP2. The Coomassie-stained gel shows *E. coli* whole cell lysate after induction of IPTG, affinity purified Trx-His-SP2 fusion protein, SP2 and Trx-His cleaved by enterokinase, separated mature SP2 and Trx-His tag by an anion-exchange chromatography. The molecular masses are indicated on the left.

The Trx-His-SP2 fusion protein was purified from the cytoplasm by affinity chromatography using Ni+ column (Amersham Pharmacia Biotech, Baie d'Urfee, Canada). The cytoplasm was filtered with a 0.45 μm membrane and subjected to the column. The fusion protein was eluted with 500 mM imidazole in binding buffer and protein-containing fractions were determined by SDS-PAGE. The purified fusion protein was cleaved by 0.001% (w/w) of enterokinase (New England BioLabs), yielding an apparent 58 kDa SP2 and the expected 20 kDa Trx-His tag (FIG. 15), and then applied to a mono-Q column (Amersham Pharmacia Biotech, Baie d'Urfee, Canada). The recombinant SP2 devoid of Trx-His tag was obtained from elution of the column by using a linear NaCl gradient, with an estimated purity greater than 95% as visualized by SDS-PAGE (FIG. 15). The protein concentration was determined by the Bio-Rad protein assay kit (Bio-Rad) according to the manufacturer's instructions. Identity of the purified SP2 was confirmed by N-terminal protein sequencing.

SP2 is an Immunogenic Protein of *S. suis* and Exhibits IgG-Binding Activity

Figure 16:
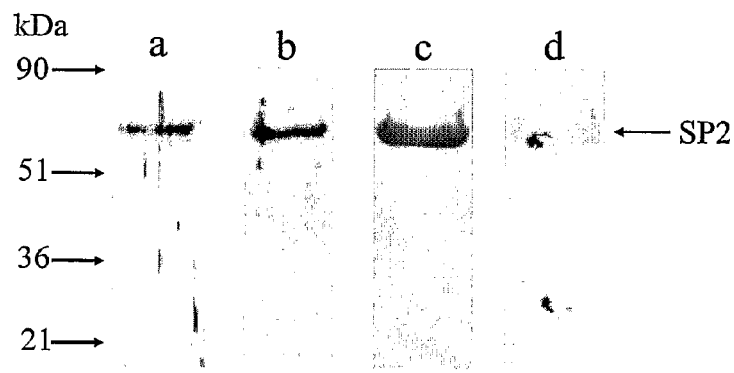
FIG. 16: Immunogenic and IgG-binding activity of recombinant SP2. a) SP2-specific rabbit serum reacts with the cell preparation of *S. suis* S735. b) Recombinant SP2 reacts with the convalescent swine serum. Recombinant SP2 binds to human (c) and pig (d) IgG.

SP2-specific antibody was generated by immunizing New Zealand White rabbits intramuscularly with 100 μg of recombinant SP2 protein emulsified with 0.5 ml of Freud's incomplete adjuvant. The rabbits received two booster injections with the same dose of the SP2 at 2-week intervals and then were bled 10 days after the last booster immunization. The SP2 specific antibody conversely recognized SP2 in *S. suis* cell preparation in a western blot (FIG. 16a). Moreover, recombinant SP2 reacted with a convalescent swine serum (FIG. 16b), demonstrating that the anti-SP2 antibody exists in the serum of pigs clinically infected by *S. suis*.

The binding activities of the recombinant SP2 to human and pig IgG were demonstrated in FIGS. 16c and 16d.

Recombinant SP2 Partially Protects Mice Against *S. Suis* Challenge Infection

Mice (CD1) were randomly assigned to two groups of eleven (vaccine group) and ten (control), and immunized subcutaneously twice at 2-week interval with either 50 μg of purified SP2 mixed with 20 μg of Quil A as a Th1 inducing adjuvant or 20 μg of Quil A only as a control. Ten days after the second vaccination, the animals were challenged i.p. with $1 \times 10^8$ CFU of a S. suis virulent strain (31533). The mice were monitored twice a day for clinical signs and mortality until day 14 after the infection. Blood samples were collected prior to each vaccination and challenge for determining antibody responses.

Figure 17:
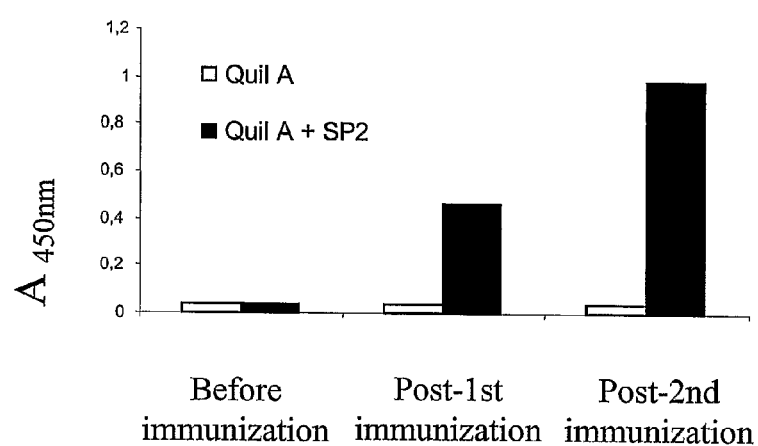
FIG. 17: Antibody response after vaccination with recombinant SP2 in mice. SP2-specific IgG in sera was measured by ELISA.
Figure 18:
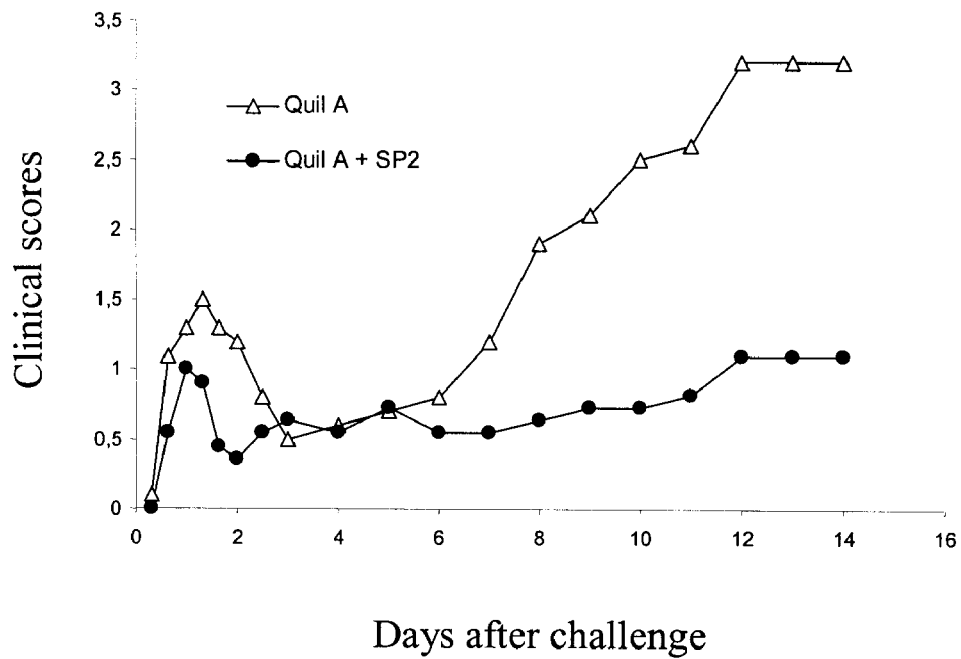
FIG. 18: Vaccination with recombinant SP2 alleviates clinical signs of the mice challenged with a virulent *S. suis* strain.
Figure 19:
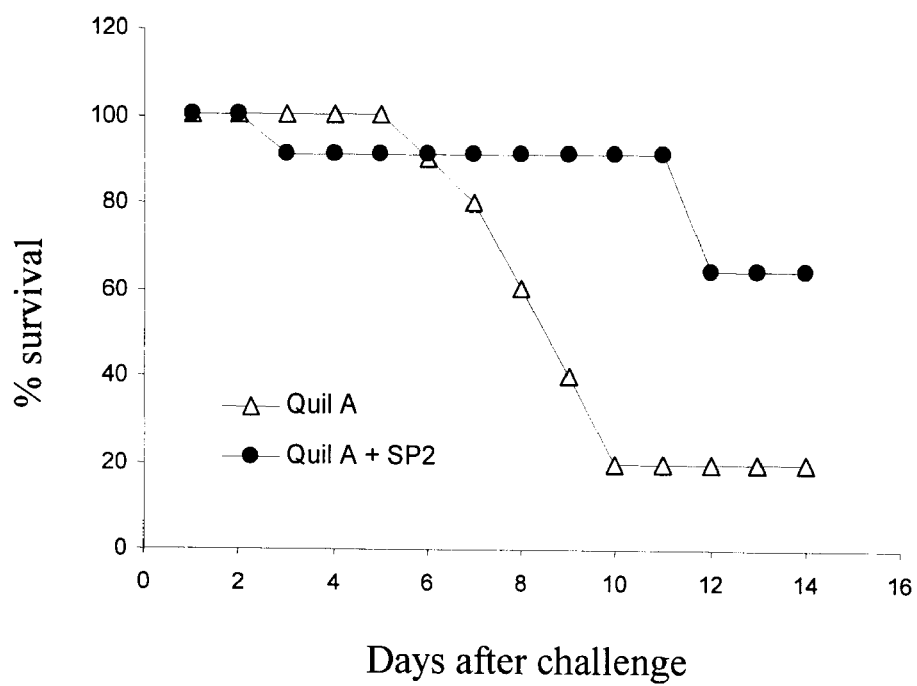
FIG. 19: Vaccination with recombinant SP2 protects mice from *S. suis* death.

Vaccination with SP2 elicited significant humoral IgG responses in mice. In contrast, the SP2-specific IgG in sera of control group was at undetectable level (FIG. 17). Both groups showed clinical signs of septicemia and meningitis, however, the clinical scores in SP2 vaccination group are lighter than in the control group (FIG. 18). 4 of 11 mice in SP2 vaccination group died or had to be euthanized due to the severity of the condition (survivor rate=64%). In contrast, 8 of 10 mice in control group died (survivor rate=20%) (FIG. 19). These results show that SP2 protects mice against S. suis challenge infection.

Conclusion

SP2 is a new described S. suis immunogenic protein which shares little identity with other known sequences. Convalescent swine sera present antibody against this protein, demonstrating that SP2 is a potent antigen that is expressed during S. suis infection. These findings, along with its wide distribution in different S. suis serotypes, make the SP2 a candidate for consideration in the development of a diagnostic reagent. Since vaccination of mice with recombinant SP2 resulted in protection, it is thus clear that SP2 is a potential vaccine candidate against S. suis infection.

Example 4

Effect of Immunization of Piglets with Experimental *Streptococcus Suis* Vaccine This study evaluates the protective effect of recombinant Sao protein on S. suis serotype 2 challenge infection in piglets.

Materials and Methods

Animals, Allocation to Treatment and Exclusion Criteria:

A total of 24 crossbred piglets from S. suis disease-free herd (H & M Fast Farms Inc.) without any previous vaccination against S. suis were used. The pigs were kept under commercial conditions at the herd of origin from birth until they were weaned at an average weight of 7.79 kg at 23.5 days of age. Pigs were housed with controlled temperature (27 to 30° C.) and ventilation, on vinyl-covered metal flooring, and were provided with water via nipple waterers and had free access to commercially-prepared, nutritionally balanced, antibiotic-free feed. A veterinarian examined the pigs prior to the beginning of the study. All were healthy. At weaning, the piglets were randomly assigned to two groups, balanced by body weight.

Group 1: 200 μg Sao and 400 μg Quil A in 1 mL Saline
Group 2: 400 μg Quil A in 1 mL Saline (control)

Any animals that receive an unintended treatment or succumb to an unrelated disease will be excluded from analysis.

Vaccination and Challenge:

All pigs were vaccinated IM with 1 ml twice at 2-week interval. Blood samples were collected before each injection and challenge. There were no adverse events as a result of these treatments.

Two weeks after the second vaccination, the pigs were anesthetized with halothane and challenged by aerosol of 1 ml of a suspension of S. suis 166. The bacteria were from a log-phase culture grown in filter sterilized Todd-Hewitt Yeast Broth to an $OD_{620}$ of 0.8 and diluted 1:100 in saline (0.85% NaCl). The bacterial concentration administered to pigs was later measured to be $6.8 \times 10^6$ CFU/ml.

Clinical Observations:

A veterinarian or trained animal care technician clinically evaluated the pigs once daily and measured body temperatures during assignment of clinical scores each morning for ten days after challenge. A daily clinical score (from 0 to 4) was derived as the sum of attitude and locomotion scores for each animal based upon signs of nervous, musculoskeletal or respiratory disease as follows:

Attitude:
0=Normal attitude and response to stimuli
1=Inactive and slow to respond; oculo-nasal secretions
2=Only responsive to repeated stimuli, apathetic
3=Recumbent, nonresponsive, unaware of surroundings
4=Dead Locomotion:
0=Normal gait and posture
1=Slight in coordination, lameness and/or joint swelling but rises without assistance
2=Clearly uncoordinated or lame but stands without assistance
3=Severe lameness, severe ataxia, does not remain standing
4=Dead Pigs having a clinical score greater than 2 on either scale were euthanized by lethal injection. Pigs with rectal temperatures equal to or greater than 40.6° C. and a clinical score greater than 0, as well as those pigs that were dead, were recorded as sick on that day. Pigs that died or were euthanized prior to the end of the experiment on day 9 were recorded as dead for evaluation of the effect of treatment on mortality rate. All individuals making judgements about animals, evaluating clinical signs of disease, or performing laboratory assays were blind to the identity of the treatment.

Haemotologic Condition:

A heparin-treated blood sample was obtained by venipuncture for detection of S. suis bacteremia (by culture on days 0 and 3 after challenge and postmortem).

Antibody Titre:

Titers of Sao-specific total IgG and IgG subclasses (IgG1 and IgG2) in sera were determined by ELISA. The serum dilution that resulted in an OD450 reading of 0.1 after background subtration was considered the titer of this serum.

Necropsy:

All pigs were examined postmortem and the following tissues were cultured for bacteria: cerebellum swab, tracheobronchial lymph node, a joint swab (an affected joint if lesions are present; otherwise a stifle joint), and blood. The number of S. suis bacteria that were recovered was recorded on an ordinal scale from 0 to 4 (approximating the $\log_{10}$ number of colonies). In addition, the extent (percentage) of pulmonary involvement was estimated by visual examination.

Statistical Analysis

The significance of differences between groups in nominal data (mortality, presence or absence of S. suis in the tissues, days sick or well) was determined using contingency table analysis and Likelihood-Ratio Fisher Exact Test. The significance of differences between groups in ordinal data (clinical score) was transformed by ranking and determined by t-test. The significance of differences between groups in survival curves was determined by survival analysis using the logrank test (equivalent to the Mantel-Haenszel test). The significance of differences among groups in continuous data (length of survival after challenge, body temperature, $\log_2$ CFU/ml of blood) was determined using t-test (after appropriate transformation to normality as required).

Results
Excluded Animals:
One pig was humanely killed on day 5 after the challenge because of persistent; worsening prolapsed rectum. This pig will be excluded from analysis.

Figure 20:
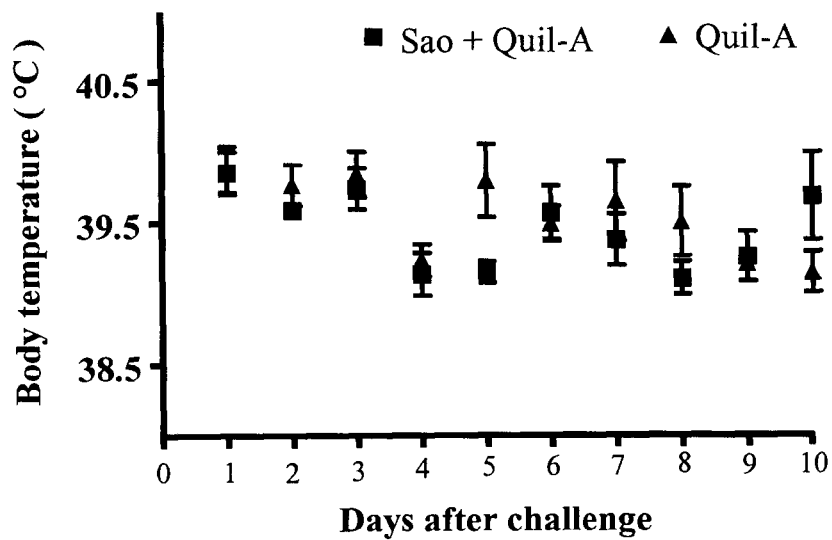
FIG. 20: Body temperature of pigs vaccinated with the composition according to a preferred embodiment of the invention, after challenge.
Figure 21:
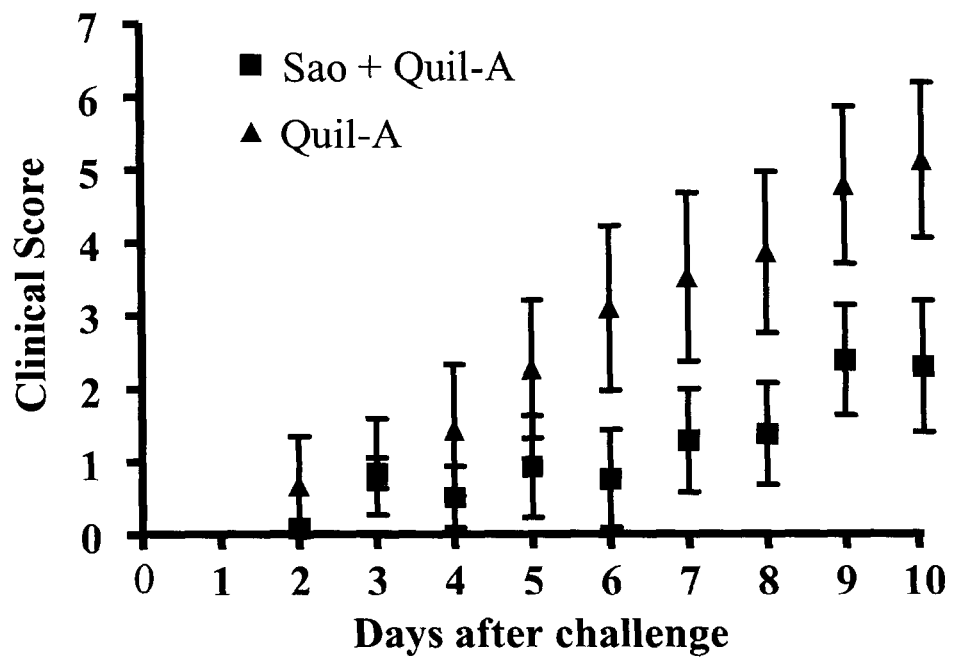
FIG. 21: Clinical disease of pigs vaccinated with the composition according to a preferred embodiment of the invention, after challenge.
Figure 22:
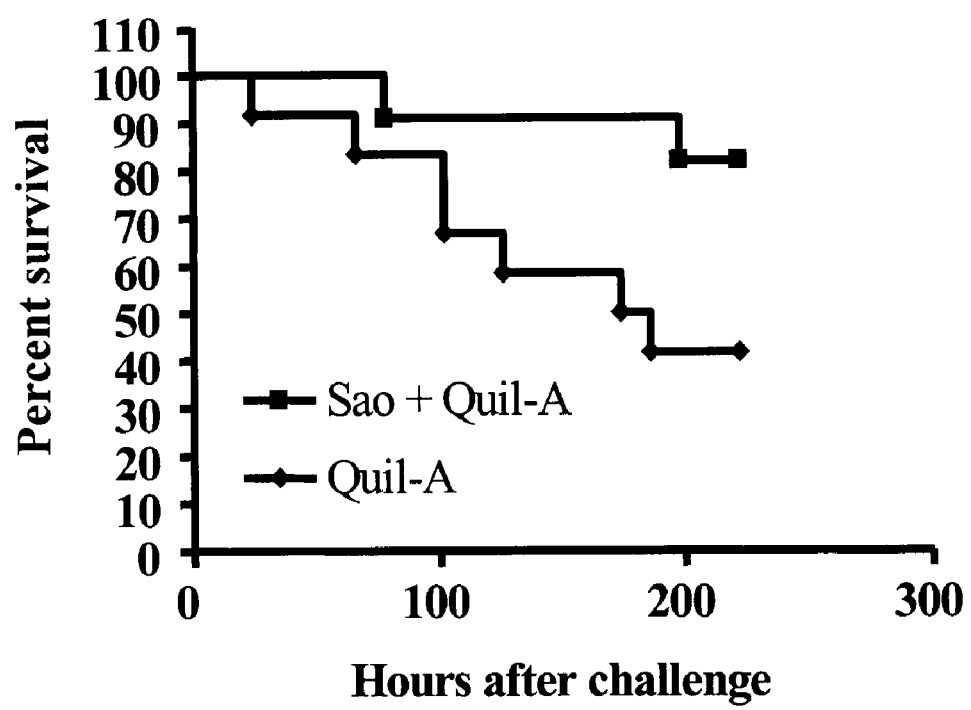
FIG. 22: Survival of pigs vaccinated with the composition according to a preferred embodiment of the invention, after challenge.

Clinical Observations:
1. Response to immunisation: There were no unusual reactions attributable to vaccination.
2. Body temperature: The body temperature data as analysed by t-test, showed no significant difference between the two group (p>0.05). Generally the vaccinated pigs tended to have lower temperatures (FIG. 20)
3. Clinical disease: The "clinical score" is a measure of the amount of disease and incorporates both mortality and morbidity. The two groups were compared using Mann-Whitney analysis of an effect of vaccine on clinical score, and the clinical disease in vaccinated group was significantly less than that in control (p=0.024) (FIG. 21).
4. Survival of pigs after *S. suis* challenge: The survival rate is 82% in vaccination group and 42% in control group, respectively. Comparison of survival curves using the two data sets, shows that the survival time of vaccinated pigs was significantly longer than that of control (p=0.048) (FIG. 22).

Bacteriology
1. Bacteremia: Bacteria in the blood of piglets were not detected (ND) before challenge. The bacteremia pigs after challenge and postmortem were not significant different between the two groups. However, the vaccinated pigs had less bacteremia (table 3).
2. Infection postmortem: Microbiologic culture of samples from the brain, tracheobronchial lymph node, and joint of all of the pigs that were challenged was done to monitor the level of infection. Number of tissues from that bacteria with colonial morphology typical of the challenge strain were recovered was shown in table 4. The Wilcoxon Rank Sum test for the effect of vaccinated group on the median bacteriology score (median of the sum of scores for all tissues of each pig) showed that this difference was significant (p=0.007).

Pathology (Post-Mortem)
Pathologic lesions of arthritis or pneumonia were detected in only 6 pigs (2 in vaccinated group and 4 in control). Other dead or euthanized pigs had no gross pathologic signs. One of characterizations of *S. suis* infection is that acute infection can be fatal without appreciable gross signs of pathology. The tracheobronchial lymph node was enlarged. There was a trace of fibrin on the mesentery, indicating a mild peritonitis. There was evidence of arthritis in both stifles, in which there was a small amount of purulent material, and in the left shoulder, where there was a trace of purulent exudate.

Figure 23:
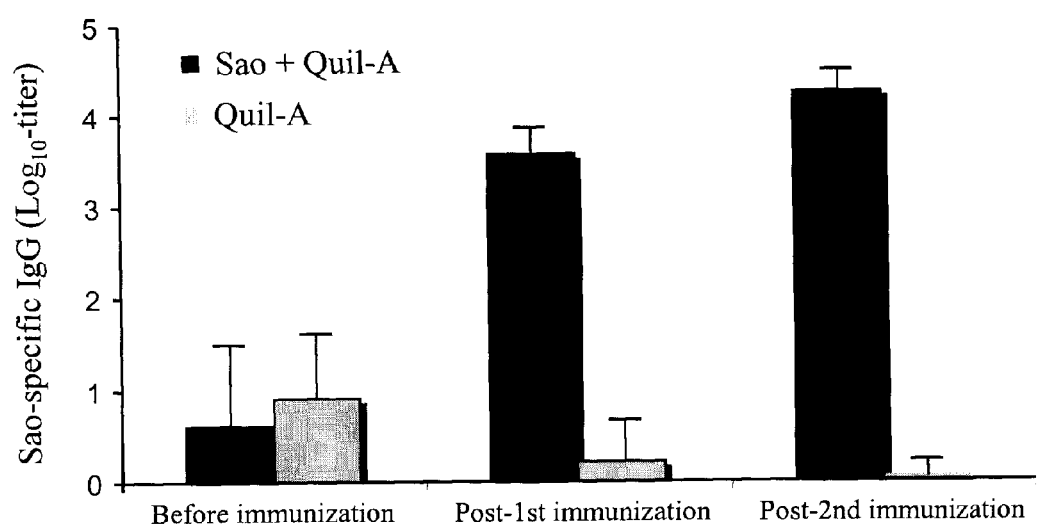
FIG. 23: Serum total IgG titers of pigs vaccinated with the composition according to a preferred embodiment of the invention.
Figure 24:
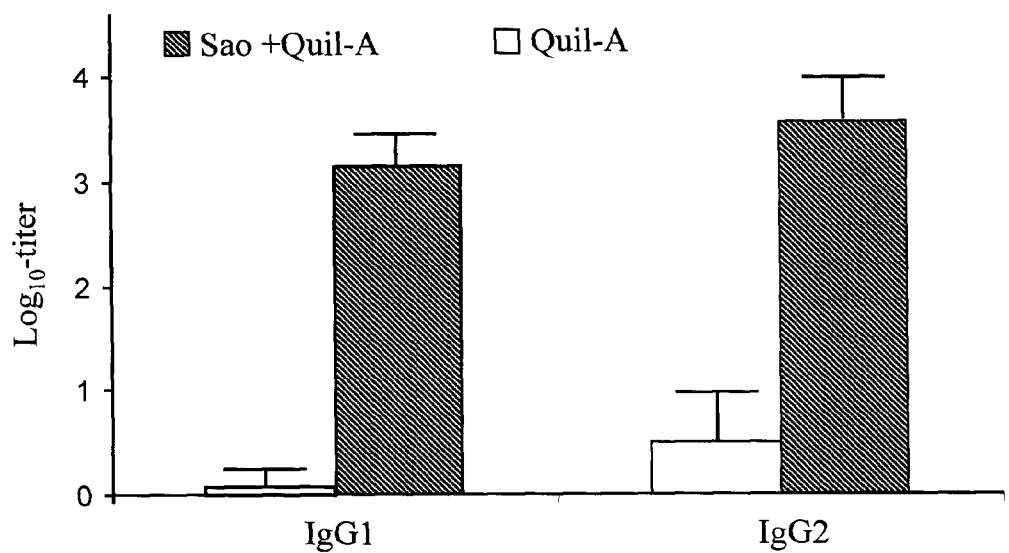
FIG. 24: IgG subclasses induced from pigs vaccinated with the composition according to a preferred embodiment of the invention.

Antibody Response
Immunization of pigs with Sao in combination with Quil A elicited significant humoral IgG responses after primary immunization and a booster injection significantly enhanced the antibody titre (FIG. 23). Furthermore, while both IgG1 and IgG2 subclasses were induced, IgG2 titer dominated over IgG1 as measured in the sera 2 weeks after the second vaccination (FIG. 24).

Summary and Discussion
The vaccine was shown to be safe since pigs that were vaccinated twice did not have any adverse reaction. Immunization of pigs with Sao in combination with Quil A elicited significant IgG titres with a dominant IgG2 production, suggesting a predominant Th1-type immune response. Aerosol challenge of pigs resulted in disease with an overall mortality rate of approximately 58% in controls. The survival of vaccinated pigs after challenge was significantly better than controls (p<0.05). Some pigs in each group became ill after challenge, and there was significantly less disease (lower clinical score) in the vaccinated pigs. Vaccination had no significant effect on the occurrence of gross pathology post-mortem; however acute streptococcal septicaemia can be fatal without appreciable gross signs of pathology. Less *S. suis* bacteria were recovered from vaccinated pigs than control pigs post mortem (p<0.01).

Example 5

Immunization of Mice and Piglets with Fragment SP1A

Immunization of Mice
Three groups of 10 mice were immunized two times (Day 1 and Day 17) via i.p. with 40 µg of purified SP1A-maltose-binding protein (MBP) fusion protein, 20 µg of MBP or only PBS, using Freund Incomplete as an adjuvant. The sera were obtained before each immunization or 10 days after the second injection, and were 1:5000 diluted for ELISA assay. (See Table 5)

Immunization of Pigs
Three groups of 3 pigs were immunized two times (Day 1 and Day 17) via i.m. with 200 µg of purified SP1A-MBP fusion protein, 100 µg of MBP or only PBS, using Emulsigen as an adjuvant. The sera were obtained before each immunization or 10 days after the second injection, and were 1:5000 diluted for ELISA assay. (See Table 6)

TABLE 1

Distributions of SP1 in *S. suis* reference strains, isolates of serotype 2 and other organisms detected by SP1-specific antibody R44 in Western blots.

| *S. suis* serotype (reference strain) | Origin | SP1 | *S. suis* isolate of serotype 2 | Origin | SP1 |
|---|---|---|---|---|---|
| 1 (5428) | The Netherlands | + | 89-999 | Canada | + |
| ½ (2651) | The Netherlands | + | 90-1330 | Canada | + |
| 2 (NCTC 10234) | The Netherlands | + | 95-8242 | Canada | + |
| 3 (4961) | Denmark | + | Man 25 | Canada | + |
| 4 (6407) | Denmark | + | Man 50 | Canada | + |
| 5 (11538) | Denmark | + | Man 63 | Canada | + |
| 6 (2524) | Denmark | + | AAH4 | USA | + |
| 7 (8074) | Denmark | + | AAH5 | USA | + |
| 8 (14636) | Denmark | + | AAH6 | USA | + |
| 9 (22083) | Denmark | + | 1309 | USA | + |
| 10 (4417) | Denmark | + | 88-5955 | USA | + |
| 11 (12814) | Denmark | + | 95-13626 | USA | + |

TABLE 1-continued

Distributions of SP1 in *S. suis* reference strains, isolates of serotype 2
and other organisms detected by SP1-specific antibody R44 in Western blots.

| 12 | (8830) | Denmark | + | 95-16426 | USA | + |
| 13 | (10581) | Denmark | − | 95-7220 | USA | + |
| 14 | (13730) | The Netherlands | + | 97-8506 | USA | + |
| 15 | (NCTC 1046) | The Netherlands | + | SX-332 | USA | + |
| 16 | (2726) | Denmark | − | JL 590 | Mexico | + |
| 17 | (93A) | Canada | + | 166 | France | + |
| 18 | (NT77) | Canada | + | 96-39247 | France | + |
| 19 | (42A) | Canada | + | 96-49808 | France | + |
| 20 | (86-5192) | USA | − | 96-53405 | France | + |
| 21 | (14A) | Canada | + | Italie 57 | Italy | + |
| 22 | (88-1861) | Canada | − | Italie 68 | Italy | + |
| 23 | (89-2479) | Canada | + | Italie 69 | Italy | − |
| 24 | (88-5299A) | Canada | − | Italie 228 | Italy | + |
| 25 | (89-3576-3) | Canada | + | S735[a] | The Netherlands | + |
| 26 | (89-4109-1) | Canada | + | | | |
| 27 | (89-5259) | Canada | + | | | |
| 28 | (89-590) | Canada | + | | | |
| 29 | (92-1191) | Canada | + | | | |
| 30 | (92-1400) | Canada | + | | | |
| 31 | (92-4172) | Canada | + | | | |
| 33 | (EA1832.92) | Canada | + | | | |

| | | Organnism | Strain | SP1 |
|---|---|---|---|---|
| 1 | 2 | *S. bovis* | ATCC 9809 | − |
| 3 | 4 | *S. equisimilis* | ATCC 9542 | − |
| 5 | 6 | *S. intestinalis* | ATTC 43492 | − |
| 7 | 8 | *S. pyogenes* | ATCC 14289 | − |
| 9 | 10 | *S. uberis* | ATCC 6580 | − |

[a]Strain used as reference in this work.

TABLE 2

Protection of pigs following challenge with *S. suis* strain 166

| Groups (n = 8) | Arthritic pigs | Bacteremic pigs | Surviving pigs |
|---|---|---|---|
| Emulsigen-Plus (Control) | 6 | 3 | 5 |
| Emulsigen-Plus + SP1 | 4 | 3 | 5 |

TABLE 3

Level of *S. suis* bacteremia.

| | Groups | | |
|---|---|---|---|
| | Sao + Quil-A | Quil-A | Significance (p) |
| Before challenge | ND (12) | ND (12) | N/A |
| 3 days after challenge | 1/11 | 2/12 | 0.6 |
| Postmorterm | 1/11 | 4/9 | 0.13 |

TABLE 4

Level of infection postmortem.

| Groups | Brain | Lymph node | Joint | Median bacteriology score |
|---|---|---|---|---|
| Sao + Quil-A | 2/11 | 6/11 | 2/11 | 1.0 |
| Quil-A | 10/12 | 8/12 | 4/12 | 4.5 |

TABLE 5

SP1A-specific IgG response in mouse sera (A450 nm)

| Group | SP1A-MBP | MBP | PBS |
|---|---|---|---|
| Before Immunization | 0.006 | 0.016 | 0.0 |
| After 1$^{st}$ Immunization | 2.809 | 0.015 | 0.005 |
| After 2$^{nd}$ Immunization | 3.153 | 0.015 | 0.004 |

TABLE 6

SP1A-specific IgG response in pigs (A450 nm)

| Group | SP1A-MBP | MBP | PBS |
|---|---|---|---|
| Before Immunization | 0.024 | 0.018 | 0.024 |
| After 1$^{st}$ Immunization | 0.254 | 0.026 | 0.015 |
| After 2$^{nd}$ Immunization | 0.501 | 0.047 | 0.033 |

REFERENCES

1. Arends, J. P., and H. C. Zanen. 1988. Meningitis caused by *Streptococcus suis* in humans. Rev Infect Dis 10:131-7.
2. Arulanandam, B. P., J. M. Lynch, D. E. Briles, S. Hollingshead, and D. W. Metzger. 2001. Intranasal vaccination with pneumococcal surface protein A and interleukin-12 augments antibody-mediated opsonization and protective immunity against *Streptococcus pneumoniae* infection. Infect Immun 69:6718-24.
3. Berthelot-Herault, F., R. Cariolet, A. Labbe, M. Gottschalk, J. Y. Cardinal, and M. Kobisch. 2001. Experimental infection of specific pathogen free piglets with French strains of *Streptococcus suis* capsular type 2. Can J Vet Res 65:196-200.
4. Buchanan, R. M., D. E. Briles, B. P. Arulanandam, M. A. Westerink, R. H. Raeder, and D. W. Metzger. 2001. IL-12- mediated increases in protection elicited by pneumococcal and meningococcal conjugate vaccines. Vaccine 19:2020-8.
5. Burnette, W. N. 1981. "Western blotting": electrophoretic transfer of proteins from sodium dodecyl sulfate—polyacrylamide gels to unmodified nitrocellulose and radiographic detection with antibody and radioiodinated protein A. Anal Biochem 112:195-203.
6. Crawley, A., and B. N. Wilkie. 2003. Porcine Ig isotypes: function and molecular characteristics. Vaccine 21:2911-22.
7. Elliott, S. D., F. Clifton-Hadley, and J. Tai. 1980. Streptococcal infection in young pigs. V. An immunogenic polysaccharide from Streptococcus suis type 2 with particular reference to vaccination against streptococcal meningitis in pigs. J Hyg (Lond) 85:275-85.
8. Galina, L., U. Vecht, H. J. Wisselink, and C. Pijoan. 1996. Prevalence of various phenotypes of Streptococcus suis isolated from swine in the U.S.A. based on the presence of muraminidase-released protein and extracellular factor. Can J Vet Res 60:72-4.
9. Gottschalk, M., R. Higgins, M. Jacques, M. Beaudoin, and J. Henrichsen. 1991. Characterization of six new capsular types (23 through 28) of Streptococcus suis. J Clin Microbiol 29:2590-4.
10. Gottschalk, M., R. Higgins, M. Jacques, M. Beaudoin, and J. Henrichsen. 1991. Isolation and characterization of Streptococcus suis capsular types 9-22. J Vet Diagn Invest 3:60-5.
11. Gottschalk, M., R. Higgins, M. Jacques, K. R. Mittal, and J. Henrichsen. 1989. Description of 14 new capsular types of Streptococcus suis. J Clin Microbiol 27:2633-6.
12. Gottschalk, M., A. Lebrun, H. Wisselink, J. D. Dubreuil, H. Smith, and U. Vecht. 1998. Production of virulence-related proteins by Canadian strains of Streptococcus suis capsular type 2. Can J Vet Res 62:75-9.
13. Gottschalk, M., and M. Segura. 2000. The pathogenesis of the meningitis caused by Streptococcus suis: the unresolved questions. Vet Microbiol 76:259-72.
14. Higgins, R., and M. Gottschalk. 1998. Distribution of Streptococcus suis capsular types in 1997. Can Vet J 39:299-300.
15. Higgins, R., M. Gottschalk, M. Boudreau, A. Lebrun, and J. Henrichsen. 1995. Description of six new capsular types (29-34) of Streptococcus suis. J Vet Diagn Invest 7:405-6.
16. Higgins, R., M. Gottschalk. 2005. Streptococcal diseases (In press). In B. E. Straw, S. D'Allaire, W. L. Mengeling, and D. J. Taylor (9th ed), Diseases of swine. Iowa State University Press, Ames.
17. Hill, J. E., M. Gottschalk, R. Brousseau, J. Harel, S. M. Hemmingsen, and S. H. Goh. 2005. Biochemical analysis, cpn60 and 16S rDNA sequence data indicate that Streptococcus suis serotypes 32 and 34, isolated from pigs, are Streptococcus orisratti. Vet Microbiol 107:63-9.
18. Holt, M. E., M. R. Enright, and T. J. Alexander. 1988. Immunisation of pigs with live cultures of Streptococcus suis type 2. Res Vet Sci 45:349-52.
19. Ioannou, X. P., P. Griebel, R. Hecker, L. A. Babiuk, and S. van Drunen Littel-van den Hurk. 2002. The immunogenicity and protective efficacy of bovine herpesvirus 1 glycoprotein D plus Emulsigen are increased by formulation with CpG oligodeoxynucleotides. J Virol 76:9002-10.
20. Jacobs, A. A., A. J. van den Berg, and P. L. Loeffen. 1996. Protection of experimentally infected pigs by suilysin, the thiol-activated haemolysin of Streptococcus suis. Vet Rec 139:225-8.
21. Laemmli, U. K. 1970. Cleavage of structural proteins during the assembly of the head of bacteriophage T4. Nature 227:680-5.
22. Lefeber, D. J., B. Benaissa-Trouw, J. F. Vliegenthart, J. P. Kamerling, W. T. Jansen, K. Kraaijeveld, and H. Snippe. 2003. Th1-directing adjuvants increase the immunogenicity of oligosaccharide-protein conjugate vaccines related to Streptococcus pneumoniae type 3. Infect Immun 71:6915-20.
23. Lofthouse, S. A., A. E. Andrews, A. D. Nash, and V. M. Bowles. 1995. Humoral and cellular responses induced by intradermally administered cytokine and conventional adjuvants. Vaccine 13:1131-7.
24. Lynch, J. M., D. E. Briles, and D. W. Metzger. 2003. Increased protection against pneumococcal disease by mucosal administration of conjugate vaccine plus interleukin-12. Infect Immun 71:4780-8.
25. Marques, M. B., D. L. Kasper, A. Shroff, F. Michon, H. J. Jennings, and M. R. Wessels. 1994. Functional activity of antibodies to the group B polysaccharide of group B streptococci elicited by a polysaccharide-protein conjugate vaccine. Infect Immun 62:1593-9.
26. McArthur, J., E. Medina, A. Mueller, J. Chin, B. J. Currie, K. S. Sriprakash, S. R. Talay, G. S. Chhatwal, and M. J. Walker. 2004. Intranasal vaccination with streptococcal fibronectin binding protein Sfb1 fails to prevent growth and dissemination of Streptococcus pyogenes in a murine skin infection model. Infect Immun 72:7342-5.
27. Miyaji, E. N., D. M. Ferreira, A. P. Lopes, M. C. Brandileone, W. O. Dias, and L. C. Leite. 2002. Analysis of serum cross-reactivity and cross-protection elicited by immunization with DNA vaccines against Streptococcus pneumoniae expressing PspA fragments from different clades. Infect Immun 70:5086-90.
28. Nichani, A. K., R. S. Kaushik, A. Mena, Y. Popowych, D. Dent, H. G. Townsend, G. Mutwiri, R. Hecker, L. A. Babiuk, and P. J. Griebel. 2004. CpG oligodeoxynucleotide induction of antiviral effector molecules in sheep. Cell Immunol 227:24-37.
29. Okwumabua, O., O. Abdelmagid, and M. M. Chengappa. 1999. Hybridization analysis of the gene encoding a hemolysin (suilysin) of Streptococcus suis type 2: evidence for the absence of the gene in some isolates. FEMS Microbiol Lett 181:113-21.
30. Pallares, F. J., C. S. Schmitt, J. A. Roth, R. B. Evans, J. M. Kinyon, and P. G. Halbur. 2004. Evaluation of a ceftiofur-washed whole cell Streptococcus suis bacterin in pigs. Can J Vet Res 68:236-40.
31. Perch, B., K. B. Pedersen, and J. Henrichsen. 1983. Serology of capsulated streptococci pathogenic for pigs: six new serotypes of Streptococcus suis. J Clin Microbiol 17:993-6.
32. Segura, M., M. Gottschalk, and M. Olivier. 2004. Encapsulated Streptococcus suis inhibits activation of signaling pathways involved in phagocytosis. Infect Immun 72:5322-30.
33. Serhir, B., D. Dugourd, M. Jacques, R. Higgins, and J. Harel. 1997. Cloning and characterization of a dextranase gene (dexS) from Streptococcus suis. Gene 190:257-61.
34. Sheoran, A. S., S. Artiushin, and J. F. Timoney. 2002. Nasal mucosal immunogenicity for the horse of a SeM peptide of Streptococcus equi genetically coupled to cholera toxin. Vaccine 20:1653-9.
35. Torremorell, M., C. Pijoan, and S. Dee. 1999. Experimental exposure of young pigs using a pathogenic strain of Streptococcus suis serotype 2 and evaluation of this method for disease prevention. Can J Vet Res 63:269-75.

36. Trottier, S., R. Higgins, G. Brochu, and M. Gottschalk. 1991. A case of human endocarditis due to *Streptococcus suis* in North America. Rev Infect Dis 13:1251-2.
37. Willson, P. J., A. Rossi-Campos, and A. A. Potter. 1995. Tissue reaction and immunity in swine immunized with *Actinobacillus pleuropneumoniae* vaccines. Can J Vet Res 59:299-305.
38. Wisselink, H. J., N. Stockhofe-Zurwieden, L. A. Hilgers, and H. E. Smith. 2002. Assessment of protective efficacy of live and killed vaccines based on a non-encapsulated mutant of *Streptococcus suis* serotype 2. Vet Microbiol 84:155-68.
39. Wisselink, H. J., U. Vecht, N. Stockhofe-Zurwieden, and H. E. Smith. 2001. Protection of pigs against challenge with virulent *Streptococcus suis* serotype 2 strains by a muramidase-released protein and extracellular factor vaccine. Vet Rec 148:473-7.
40. Wortham, C., L. Grinberg, D. C. Kaslow, D. E. Briles, L. S. McDaniel, A. Lees, M. Flora, C. M. Snapper, and J. J. Mond. 1998. Enhanced protective antibody responses to PspA after intranasal or subcutaneous injections of PspA genetically fused to granulocyte-macrophage colony-stimulating factor or interleukin-2. Infect Immun 66:1513-20.
41. Yang, B., W. Zhu, L. B. Johnson, and F. F. White. 2000. The virulence factor AvrXa7 of *Xanthomonas oryzae* pv. *oryzae* is a type III secretion pathway-dependent nuclear-localized double-stranded DNA-binding protein. Proc Natl Acad Sci USA 97:9807-12.
42. Pollack, M., N. L. Koles, M. J. Preston, B. J. Brown, and G. B. Pier. 1995. Functional properties of isotype-switched immunoglobulin M (IgM) and IgG monoclonal antibodies to *Pseudomonas aeruginosa* lipopolysaccharide. Infect Immun 63:4481-8.
43. Unkeless, J. C., E. Scigliano, and V. H. Freedman. 1988. Structure and function of human and murine receptors for IgG. Annu Rev Immunol 6:251-81.
44. Serhir, B., D. Dugourd, M. Jacques, R. Higgins, and J. Harel. 1997. Cloning and characterization of a dextranase gene (dexS) from *Streptococcus suis*. Gene 190:257-61.

The invention claimed is:

1. An isolated polypeptide comprising an amino acid sequence having at least 75% identity to the amino acid sequence set forth in SEQ ID NO: 1 or in SEQ ID NO: 4.

2. The isolated polypeptide of claim 1, comprising at least one repetitive amino acid sequence consisting of the amino acid sequence Xaa$_1$ Ser Xaa$_3$ Xaa$_4$ Xaa$_5$ Met Xaa$_7$ Xaa$_8$ Xaa$_9$ Xaa$_{10}$ Xaa$_{11}$ Xaa$_{12}$ Xaa$_{13}$ Xaa$_{14}$ Xaa$_{15}$ Xaa$_{16}$ Pro Xaa$_{18}$ Xaa$_{19}$ Gln Met Xaa$_{22}$ Asn Lys Glu Xaa$_{26}$ Xaa$_{27}$ Xaa$_{28}$ Xaa$_{29}$ Xaa$_{30}$ (SEQ ID NO 9) wherein Xaa$_1$ is Val, Thr or Ile;
Xaa$_3$ is Lys or Glu;
Xaa$_4$ is Lys or Glu;
Xaa$_5$ is Ala or Gln;
Xaa$_7$ is Thr or Pro;
Xaa$_8$ is Gly, Ser or Val;
Xaa$_9$ is Lys, Val, Ile or Asn;
Xaa$_{10}$ is Glu or Val;
Xaa$_{11}$ is Lys or Asn;
Xaa$_{12}$ is Gly, Glu or Asp;
Xaa$_{13}$ is Asn or Met;
Xaa$_{14}$ is Ile, Ala or Val;
Xaa$_{15}$ is Glu or Val;
Xaa$_{16}$ is Pro or Thr;
Xaa$_{18}$ is Glu or Gln;
Xaa$_{19}$ is Lys or Glu;
Xaa$_{22}$ is Thr or Ala;
Xaa$_{26}$ is Lys or Asn;
Xaa$_{27}$ is Asp or Glu;
Xaa$_{28}$ is Asn or Lys;
Xaa$_{29}$ is Ile or Val and
Xaa$_{30}$ is Glu or Val.

3. The isolated polypeptide of claim 1, comprising the amino acid sequence as set forth in SEQ ID NO 10.

4. The isolated polypeptide of claim 1, comprising an amino acid having at least 85% identity to the amino acid sequence set forth in SEQ ID NO 1 or in SEQ ID NO 4.

5. The isolated polypeptide of claim 1, comprising an amino acid sequence having at least 95% identity to the amino acid sequence set forth in SEQ ID NO 1.

6. The isolated polypeptide of claim 1, comprising an amino acid sequence having at least 95% identity to the amino acid sequence set forth in SEQ ID NO 4.

7. The isolated polypeptide of claim 1, wherein it elicits a protective response to a *Streptococcus suis* strain challenge when administered to an animal.

8. The isolated polypeptide of claim 3, comprising at least one repetitive amino acid sequence consisting of the amino acid sequence Xaa$_1$ Ser Xaa$_3$ Xaa$_4$ Xaa$_5$ Met Xaa$_7$ Xaa$_8$ Xaa$_9$ Xaa$_{10}$ Xaa$_{11}$ Xaa$_{12}$ Xaa$_{13}$ Xaa$_{14}$ Xaa$_{15}$ Xaa$_{16}$ Pro Xaa$_{18}$ Xaa$_{19}$ Gln Met Xaa$_{22}$ Asn Lys Glu Xaa$_{26}$ Xaa$_{27}$ Xaa$_{28}$ Xaa$_{29}$ Xaa$_{30}$ (SEQ ID NO 9) wherein Xaa$_1$ is Val, Thr or Ile;
Xaa$_3$ is Lys or Glu;
Xaa$_4$ is Lys or Glu;
Xaa$_5$ is Ala or Gln;
Xaa$_7$ is Thr or Pro;
Xaa$_8$ is Gly, Ser or Val;
Xaa$_9$ is Lys, Val, Ile or Asn;
Xaa$_{10}$ is Glu or Val;
Xaa$_{11}$ is Lys or Asn;
Xaa$_{12}$ is Gly, Glu or Asp;
Xaa$_{13}$ is Asn or Met;
Xaa$_{14}$ is Ile, Ala or Val;
Xaa$_{15}$ is Glu or Val;
Xaa$_{16}$ is Pro or Thr;
Xaa$_{18}$ is Glu or Gln;
Xaa$_{19}$ is Lys or Glu;
Xaa$_{22}$ is Thr or Ala;
Xaa$_{26}$ is Lys or Asn;
Xaa$_{27}$ is Asp or Glu;
Xaa$_{28}$ is Asn or Lys;
Xaa$_{29}$ is Ile or Val and
Xaa$_{30}$ is Glu or Val.

9. The isolated polypeptide of claim 4, comprising at least one repetitive amino acid sequence consisting of the amino acid sequence Xaa$_1$ Ser Xaa$_3$ Xaa$_4$ Xaa$_5$ Met Xaa$_7$ Xaa$_8$ Xaa$_9$ Xaa$_{10}$ Xaa$_{11}$ Xaa$_{12}$ Xaa$_{13}$ Xaa$_{14}$ Xaa$_{15}$ Xaa$_{16}$ Pro Xaa$_{18}$ Xaa$_{19}$ Gln Met Xaa$_{22}$ Asn Lys Glu Xaa$_{26}$ Xaa$_{27}$ Xaa$_{28}$ Xaa$_{29}$ Xaa$_{30}$ (SEQ ID NO 9) wherein Xaa$_1$ is Val, Thr or Ile;
Xaa$_3$ is Lys or Glu;
Xaa$_4$ is Lys or Glu;
Xaa$_5$ is Ala or Gln;
Xaa$_7$ is Thr or Pro;
Xaa$_8$ is Gly, Ser or Val;
Xaa$_9$ is Lys, Val, Ile or Asn;
Xaa$_{10}$ is Glu or Val;
Xaa$_{11}$ is Lys or Asn;
Xaa$_{12}$ is Gly, Glu or Asp;
Xaa$_{13}$ is Asn or Met;
Xaa$_{14}$ is Ile, Ala or Val;
Xaa$_{15}$ is Glu or Val;
Xaa$_{16}$ is Pro or Thr;
Xaa$_{18}$ is Glu or Gln;
Xaa$_{19}$ is Lys or Glu;
Xaa$_{22}$ is Thr or Ala;
Xaa$_{26}$ is Lys or Asn;
Xaa$_{27}$ is Asp or Glu;
Xaa$_{28}$ is Asn or Lys;
Xaa$_{29}$ is Ile or Val and
Xaa$_{30}$ is Glu or Val.

10. The isolated polypeptide of claim 5, comprising at least one repetitive amino acid sequence consisting of the amino acid sequence Xaa$_1$ Ser Xaa$_3$ Xaa$_4$ Xaa$_5$ Met Xaa$_7$ Xaa$_8$ Xaa$_9$ Xaa$_{10}$ Xaa$_{11}$ Xaa$_{12}$ Xaa$_{13}$ Xaa$_{14}$ Xaa$_{15}$ Xaa$_{16}$ Pro Xaa$_{18}$ Xaa$_{19}$ Gln Met Xaa$_{22}$ Asn Lys Glu Xaa$_{26}$ Xaa$_{27}$ Xaa$_{28}$ Xaa$_{29}$ Xaa$_{30}$ (SEQ ID NO 9) wherein Xaa$_1$ is Val, Thr or Ile;
Xaa$_3$ is Lys or Glu;
Xaa$_4$ is Lys or Glu;
Xaa$_5$ is Ala or Gln;
Xaa$_7$ is Thr or Pro;
Xaa$_8$ is Gly, Ser or Val;
Xaa$_9$ is Lys, Val, Ile or Asn;
Xaa$_{10}$ is Glu or Val;

Xaa₁₁ is Lys or Asn;
Xaa₁₂ is Gly, Glu or Asp;
Xaa₁₃ is Asn or Met;
Xaa₁₄ is Ile, Ala or Val;
Xaa₁₅ is Glu or Val;
Xaa₁₆ is Pro or Thr;
Xaa₁₈ is Glu or Gln;
Xaa₁₉ is Lys or Glu;
Xaa₂₂ is Thr or Ala;
Xaa₂₆ is Lys or Asn;
Xaa₂₇ is Asp or Glu;
Xaa₂₈ is Asn or Lys;
Xaa₂₉ is Ile or Val and
Xaa₃₀ is Glu or Val.

11. The isolated polypeptide of claim 6, comprising at least one repetitive amino acid sequence consisting of the amino acid sequence Xaa₁ Ser Xaa₃ Xaa₄ Xaa₅ Met Xaa₇ Xaa₈ Xaa₉ Xaa₁₀ Xaa₁₁ Xaa₁₂ Xaa₁₃ Xaa₁₄ Xaa₁₅ Xaa₁₆ Pro Xaa₁₈ Xaa₁₉ Gln Met Xaa₂₂ Asn Lys Glu Xaa₂₆ Xaa₂₇ Xaa₂₈ Xaa₂₉ Xaa₃₀ (SEQ ID NO 9) wherein
Xaa₁ is Val, Thr or Ile;
Xaa₃ is Lys or Glu;
Xaa₄ is Lys or Glu;
Xaa₅ is Ala or Gln;
Xaa₇ is Thr or Pro;
Xaa₈ is Gly, Ser or Val;
Xaa₉ is Lys, Val, Ile or Asn;
Xaa₁₀ is Glu or Val;
Xaa₁₁ is Lys or Asn;
Xaa₁₂ is Gly, Glu or Asp;
Xaa₁₃ is Asn or Met;
Xaa₁₄ is Ile, Ala or Val;
Xaa₁₅ is Glu or Val;
Xaa₁₆ is Pro or Thr;
Xaa₁₈ is Glu or Gln;
Xaa₁₉ is Lys or Glu;
Xaa₂₂ is Thr or Ala;
Xaa₂₆ is Lys or Asn;
Xaa₂₇ is Asp or Glu;
Xaa₂₈ is Asn or Lys;
Xaa₂₉ is Ile or Val and
Xaa₃₀ is Glu or Val.

12. The isolated polypeptide of claim 1, comprising an amino acid sequence having 100% identity to the amino acid sequence set forth in SEQ ID NO 1.

13. The isolated polypeptide of claim 1, comprising an amino acid sequence having 100% identity to the amino acid sequence set forth in SEQ ID NO 4.

14. An isolated polypeptide, comprising an amino acid sequence having at least 95% identity to the amino acid sequence set forth in SEQ ID NO 2.

15. The isolated polypeptide of claim 14, comprising an amino acid sequence having 100% identity to the amino acid sequence set forth in SEQ ID NO 2.

16. An isolated polypeptide, comprising an amino acid sequence having at least 95% identity to the amino acid sequence set forth in SEQ ID NO 3.

17. The isolated polypeptide of claim 16, comprising an amino acid sequence having 100% identity to the amino acid sequence set forth in SEQ ID NO 3.

18. A composition comprising an acceptable carrier and at least one of the following elements:
   a polypeptide as defined in any one of claims 1, 2, 3, 4, 5, 6, 7, and 8 to 17.

19. A composition for eliciting an immune response to *Streptococcus* or treating *Streptococcus suis*-associated diseases or infection caused by *S. suis*, comprising an acceptable carrier and at least one of the following elements:
   a polypeptide as defined in any one of claims 1, 2, 3, 4, 5, 6, 7, and 8 to 17.

20. The composition of claim 19, further comprising an adjuvant.

* * * * *

SEQUENCE LISTING

```
<160> NUMBER OF SEQ ID NOS: 18

<210> SEQ ID NO 1
<211> LENGTH: 670
<212> TYPE: PRT
<213> ORGANISM: Streptococcus suis

<400> SEQUENCE: 1

Met Asn Thr Lys Lys Trp Arg Thr Ser Leu Leu Ile Pro Gly Ile Val
1               5                   10                  15

Leu Phe Gly Thr Val Ala Leu Val Asn Asn Val Ser Ala Gln Glu Val
                20                  25                  30

Lys Asn Thr Ile Ile Ser Ala Lys Gln Pro Asp Gly Gly Gln Ala Thr
            35                  40                  45

Ser Lys Ala Val Asn Val Lys Ile Pro Ala Val Val Arg Leu Phe Gly
    50                  55                  60

Arg Glu Leu Leu Glu Asn Glu Phe Lys Phe Glu Leu Arg Glu Ala Asn
65                  70                  75                  80

Gly Glu Glu Leu Pro Val Leu Asp Thr Ala Gln Asn Thr Lys Glu Gly
                85                  90                  95

Gln Val Arg Phe Lys Asn Leu Ser Phe Asp Lys Pro Gly Lys Tyr Trp
            100                 105                 110

Tyr Thr Ile Ser Glu Val Lys Asp Glu Leu Gly Gly Ile Glu Tyr Asp
        115                 120                 125

Ser Lys Tyr Ile Val Ala Lys Ile Thr Val Glu Asp Arg Asn Gly Gln
    130                 135                 140

Leu Gln Ala Met Ile Glu Phe Ile Asp Asn Asp Asn Val Phe Asn Asn
145                 150                 155                 160

Phe Tyr Thr Pro Ala Pro Ala Ala Ser Leu Ser Ile Lys Lys Val
                165                 170                 175

Leu Glu Gly Arg Thr Leu Asn Thr Gly Glu Phe Glu Phe Val Leu Lys
            180                 185                 190

Asn Glu Lys Gly Asp Glu Ile Glu Lys Val Ser Asn Gln Ala Asp Gly
        195                 200                 205

Ser Val Asn Phe Ser Ala Leu Thr Phe Thr Lys Glu Gly Thr Tyr Thr
    210                 215                 220
```

-continued

```
Tyr Thr Val Ser Glu Val Asp Gly Gly Leu Gly Asp Ile Ile Tyr Asp
225                 230                 235                 240

Lys Ser Asp Ile Lys Ala Thr Val Thr Val Lys Asp Asn Asn His Gly
                245                 250                 255

Gln Leu Val Ser Thr Val Thr Tyr Glu Asn Ser Asp Gln Ile Phe Glu
            260                 265                 270

Asn Ile Leu Asn Pro Gly Lys Leu Ile Ala Pro Thr Thr Asp Ser Val
        275                 280                 285

Ile Thr Asp Asn Glu Val Ser Lys Glu Ala Met Ala Gly Lys Glu Lys
    290                 295                 300

Gly Asn Ile Glu Pro Pro Lys Glu Gln Ile Ala Asn Glu Glu Lys Asp
305                 310                 315                 320

Asn Ile Glu Ala Ser Glu Lys Gln Met Pro Ser Ile Val Asn Asp Met
                325                 330                 335

Val Val Thr Pro Glu Lys Gln Met Thr Asn Lys Glu Asn Asp Lys Val
            340                 345                 350

Val Ile Ser Glu Lys Gln Met Pro Ser Val Val Asn Glu Asn Ala Val
        355                 360                 365

Thr Pro Glu Lys Gln Met Thr Asn Lys Glu Asn Asp Asn Ile Glu Thr
    370                 375                 380

Ser Glu Lys Gln Met Pro Ser Val Val Asn Glu Asn Ala Val Thr Pro
385                 390                 395                 400

Glu Lys Gln Met Thr Asn Lys Glu Lys Asp Asn Ile Glu Thr Ser Glu
                405                 410                 415

Lys Gln Met Pro Ser Val Val Asn Glu Asn Ala Val Thr Pro Glu Lys
            420                 425                 430

Gln Met Thr Asn Lys Glu Lys Asp Asn Ile Glu Thr Ser Glu Lys Gln
        435                 440                 445

Met Pro Ser Ile Val Asn Asp Met Val Val Thr Pro Gln Glu Gln Met
    450                 455                 460

Ala Asn Lys Glu Asn Asp Lys Val Val Ile Ser Glu Lys Gln Met Pro
465                 470                 475                 480

Ser Ile Val Asn Asp Met Val Val Thr Pro Gln Glu Gln Met Ala Asn
                485                 490                 495

Lys Glu Asn Asp Lys Val Val Ile Ser Glu Lys Gln Met Pro Ser Ile
            500                 505                 510

Val Asn Asp Met Val Val Thr Pro Gln Glu Gln Met Ala Asn Lys Glu
        515                 520                 525

Asn Asp Lys Val Val Ile Ser Glu Lys Gln Met Pro Ser Ile Val Asn
    530                 535                 540

Asp Met Val Val Thr Pro Gln Glu Gln Met Ala Asn Lys Glu Asn Asp
545                 550                 555                 560

Lys Val Glu Thr Ser Glu Lys Gln Met Pro Val Asn Glu Lys Asp Asn
                565                 570                 575

Ala Val Thr Pro Glu Lys Gln Met Ala Asn Lys Glu Lys Glu Asn Ile
            580                 585                 590

Glu Thr Ser Lys Lys Gln Ile Pro Val Asn Glu Asn Gln Asn Gly
        595                 600                 605

Thr Val Glu Glu Asn Ser Asn Thr Lys Pro Thr Thr Glu Lys Thr Asp
    610                 615                 620

Lys Gln Glu Thr Ser Thr Phe Lys Thr Glu Thr Ala Lys Gln Ile Leu
625                 630                 635                 640

Pro Val Thr Gly Glu Lys Gly Ser Leu Trp Leu Leu Thr Ser Gly Ile
                645                 650                 655
```

Ile Gly Leu Ala Ile Ala Leu Phe Thr Arg Lys Arg Lys Leu
            660                 665                 670

<210> SEQ ID NO 2
<211> LENGTH: 580
<212> TYPE: PRT
<213> ORGANISM: Streptococcus suis

<400> SEQUENCE: 2

Met Asn Thr Lys Lys Trp Arg Thr Ser Leu Leu Ile Pro Gly Ile Val
1               5                   10                  15

Leu Phe Gly Thr Val Ala Leu Val Asn Asn Val Ser Ala Gln Glu Val
            20                  25                  30

Lys Asn Thr Ile Ile Ser Ala Lys Gln Pro Asp Gly Gly Gln Ala Thr
        35                  40                  45

Ser Lys Ala Val Asn Val Lys Ile Pro Ala Val Val Arg Leu Phe Gly
    50                  55                  60

Arg Glu Leu Leu Glu Asn Glu Phe Lys Phe Glu Leu Arg Glu Ala Asn
65                  70                  75                  80

Gly Glu Glu Leu Pro Val Leu Asp Thr Ala Gln Asn Thr Lys Glu Gly
                85                  90                  95

Gln Val Arg Phe Lys Asn Leu Ser Phe Asp Lys Pro Gly Lys Tyr Trp
            100                 105                 110

Tyr Thr Ile Ser Glu Val Lys Asp Glu Leu Gly Gly Ile Glu Tyr Asp
        115                 120                 125

Ser Lys Tyr Ile Val Ala Lys Ile Thr Val Glu Asp Arg Asn Gly Gln
    130                 135                 140

Leu Gln Ala Met Ile Glu Phe Ile Asp Asn Asp Asn Val Phe Asn Asn
145                 150                 155                 160

Phe Tyr Thr Pro Ala Pro Ala Ala Ser Leu Ser Ile Lys Lys Val
                165                 170                 175

Leu Glu Gly Arg Thr Leu Asn Thr Gly Glu Phe Glu Phe Val Leu Lys
            180                 185                 190

Asn Glu Lys Gly Asp Glu Ile Glu Lys Val Ser Asn Gln Ala Asp Gly
        195                 200                 205

Ser Val Asn Phe Ser Ala Leu Thr Phe Thr Lys Glu Gly Thr Tyr Thr
    210                 215                 220

Tyr Thr Val Ser Glu Val Asp Gly Gly Leu Gly Asp Ile Ile Tyr Asp
225                 230                 235                 240

Lys Ser Asp Ile Lys Ala Thr Val Thr Val Lys Asp Asn Asn His Gly
                245                 250                 255

Gln Leu Val Ser Thr Val Thr Tyr Glu Asn Ser Asp Gln Ile Phe Glu
            260                 265                 270

Asn Ile Leu Asn Pro Gly Lys Leu Ile Ala Pro Thr Thr Asp Ser Val
        275                 280                 285

Ile Thr Asp Asn Glu Val Ser Lys Glu Ala Met Ala Gly Lys Glu Lys
    290                 295                 300

Gly Asn Ile Glu Pro Pro Lys Glu Gln Ile Ala Asn Glu Glu Lys Asp
305                 310                 315                 320

Asn Ile Glu Ala Ser Glu Lys Gln Met Pro Ser Val Val Asn Glu Asn
                325                 330                 335

Ala Val Thr Pro Glu Lys Gln Met Thr Asn Lys Glu Lys Asp Asn Ile
            340                 345                 350

Glu Thr Ser Glu Lys Gln Met Pro Ser Ile Val Asn Asp Met Val Val
        355                 360                 365

Thr Pro Gln Glu Gln Met Ala Asn Lys Glu Asn Asp Lys Val Val Ile
    370                 375                 380

Ser Glu Lys Gln Met Pro Ser Ile Val Asn Asp Met Val Val Thr Pro
385                 390                 395                 400

Gln Glu Gln Met Ala Asn Lys Glu Asn Asp Lys Val Val Ile Ser Glu
            405                 410                 415

Lys Gln Met Pro Ser Ile Val Asn Asp Met Val Val Thr Pro Gln Glu
        420                 425                 430

Gln Met Ala Asn Lys Glu Asn Asp Lys Val Val Ile Ser Glu Lys Gln
    435                 440                 445

Met Pro Ser Ile Val Asn Asp Met Val Val Thr Pro Gln Glu Gln Met
450                 455                 460

Ala Asn Lys Glu Asn Asp Lys Val Glu Thr Ser Glu Lys Gln Met Pro
465                 470                 475                 480

Val Asn Glu Lys Asp Asn Ala Val Thr Pro Glu Lys Gln Met Ala Asn
            485                 490                 495

Lys Glu Lys Glu Asn Ile Glu Thr Ser Lys Lys Gln Ile Pro Val Asn
        500                 505                 510

Glu Asn Gln Asn Gly Thr Val Glu Glu Asn Ser Asn Thr Lys Pro
    515                 520                 525

Thr Thr Glu Lys Thr Asp Lys Gln Glu Thr Ser Thr Phe Lys Thr Glu
530                 535                 540

Thr Ala Lys Gln Ile Leu Pro Val Thr Gly Glu Lys Gly Ser Leu Trp
545                 550                 555                 560

Leu Leu Thr Ser Gly Ile Ile Gly Leu Ala Ile Ala Leu Phe Thr Arg
            565                 570                 575

Lys Arg Lys Leu
        580

<210> SEQ ID NO 3
<211> LENGTH: 520
<212> TYPE: PRT
<213> ORGANISM: Streptococcus suis

<400> SEQUENCE: 3

Met Asn Thr Lys Lys Trp Arg Thr Ser Leu Leu Ile Pro Gly Ile Val
1               5                   10                  15

Leu Phe Gly Thr Val Ala Leu Val Asn Asn Val Ser Ala Gln Glu Val
            20                  25                  30

Lys Asn Thr Ile Ile Ser Ala Lys Gln Pro Asp Gly Gly Gln Ala Thr
        35                  40                  45

Ser Lys Ala Val Asn Val Lys Ile Pro Ala Val Val Arg Leu Phe Gly
    50                  55                  60

Arg Glu Leu Leu Glu Asn Glu Phe Lys Phe Glu Leu Arg Glu Ala Asn
65                  70                  75                  80

Gly Glu Glu Leu Pro Val Leu Asp Thr Ala Gln Asn Thr Lys Glu Gly
            85                  90                  95

Gln Val Arg Phe Lys Asn Leu Ser Phe Asp Lys Pro Gly Lys Tyr Trp
        100                 105                 110

Tyr Thr Ile Ser Glu Val Lys Asp Glu Leu Gly Gly Ile Glu Tyr Asp
    115                 120                 125

Ser Lys Tyr Ile Val Ala Lys Ile Thr Val Glu Asp Arg Asn Gly Gln
130                 135                 140

Leu Gln Ala Met Ile Glu Phe Ile Asp Asn Asp Asn Val Phe Asn Asn
145                 150                 155                 160

```
Phe Tyr Thr Pro Ala Pro Ala Ala Ala Ser Leu Ser Ile Lys Lys Val
                165                 170                 175

Leu Glu Gly Arg Thr Leu Asn Thr Gly Glu Phe Glu Phe Val Leu Lys
            180                 185                 190

Asn Glu Lys Gly Asp Glu Ile Glu Lys Val Ser Asn Gln Ala Asp Gly
        195                 200                 205

Ser Val Asn Phe Ser Ala Leu Thr Phe Thr Lys Glu Gly Thr Tyr Thr
    210                 215                 220

Tyr Thr Val Ser Glu Val Asp Gly Gly Leu Gly Asp Ile Ile Tyr Asp
225                 230                 235                 240

Lys Ser Asp Ile Lys Ala Thr Val Thr Val Lys Asp Asn Asn His Gly
                245                 250                 255

Gln Leu Val Ser Thr Val Thr Tyr Glu Asn Ser Asp Gln Ile Phe Glu
            260                 265                 270

Asn Ile Leu Asn Pro Gly Lys Leu Ile Ala Pro Thr Thr Asp Ser Val
        275                 280                 285

Ile Thr Asp Asn Glu Val Ser Lys Glu Ala Met Ala Gly Lys Glu Lys
    290                 295                 300

Gly Asn Ile Glu Pro Pro Lys Glu Gln Ile Ala Asn Glu Glu Lys Asp
305                 310                 315                 320

Asn Ile Glu Ala Ser Glu Lys Gln Met Pro Ser Ile Val Asn Asp Met
                325                 330                 335

Val Val Thr Pro Glu Lys Gln Met Thr Asn Lys Glu Asn Asp Lys Val
            340                 345                 350

Val Ile Ser Glu Lys Gln Met Pro Ser Val Val Asn Glu Asn Ala Val
        355                 360                 365

Thr Pro Glu Lys Gln Met Thr Asn Lys Glu Asn Asp Asn Ile Glu Thr
    370                 375                 380

Ser Glu Lys Gln Met Pro Ser Val Val Asn Glu Asn Ala Val Thr Pro
385                 390                 395                 400

Glu Lys Gln Met Thr Asn Lys Glu Lys Asp Asn Ile Glu Thr Ser Glu
                405                 410                 415

Lys Gln Met Pro Ser Val Val Asn Glu Asn Ala Val Thr Pro Glu Lys
            420                 425                 430

Gln Met Thr Asn Lys Glu Lys Asp Asn Ile Glu Thr Ser Glu Lys Gln
        435                 440                 445

Ile Pro Val Asn Glu Asn Asn Gln Asn Gly Thr Val Glu Glu Asn Ser
    450                 455                 460

Asn Thr Lys Pro Thr Thr Glu Lys Thr Asp Lys Gln Glu Thr Ser Thr
465                 470                 475                 480

Phe Lys Thr Glu Thr Ala Lys Gln Ile Leu Pro Val Thr Gly Glu Lys
                485                 490                 495

Gly Ser Leu Trp Leu Leu Thr Ser Gly Ile Ile Gly Leu Ala Ile Ala
            500                 505                 510

Leu Phe Thr Arg Lys Arg Lys Leu
        515                 520

<210> SEQ ID NO 4
<211> LENGTH: 315
<212> TYPE: PRT
<213> ORGANISM: Streptococcus suis

<400> SEQUENCE: 4

Ser Ala Gln Glu Val Lys Asn Thr Ile Ile Ser Ala Lys Gln Pro Asp
1               5                   10                  15
```

```
Gly Gly Gln Ala Thr Ser Lys Ala Val Asn Val Lys Ile Pro Ala Val
         20                  25                  30

Val Arg Leu Phe Gly Arg Glu Leu Leu Glu Asn Glu Phe Lys Phe Glu
             35                  40                  45

Leu Arg Glu Ala Asn Gly Glu Leu Pro Val Leu Asp Thr Ala Gln
 50                  55                  60

Asn Thr Lys Glu Gly Gln Val Arg Phe Lys Asn Leu Ser Phe Asp Lys
 65                  70                  75                  80

Pro Gly Lys Tyr Trp Tyr Thr Ile Ser Glu Val Lys Asp Glu Leu Gly
                 85                  90                  95

Gly Ile Glu Tyr Asp Ser Lys Tyr Ile Val Ala Lys Ile Thr Val Glu
                100                 105                 110

Asp Arg Asn Gly Gln Leu Gln Ala Met Ile Glu Phe Ile Asp Asn Asp
            115                 120                 125

Asn Val Phe Asn Asn Phe Tyr Thr Pro Ala Pro Ala Ala Ser Leu
130                 135                 140

Ser Ile Lys Lys Val Leu Glu Gly Arg Thr Leu Asn Thr Gly Glu Phe
145                 150                 155                 160

Glu Phe Val Leu Lys Asn Glu Lys Gly Asp Glu Ile Glu Lys Val Ser
                165                 170                 175

Asn Gln Ala Asp Gly Ser Val Asn Phe Ser Ala Leu Thr Phe Thr Lys
            180                 185                 190

Glu Gly Thr Tyr Thr Tyr Thr Val Ser Glu Val Asp Gly Gly Leu Gly
        195                 200                 205

Asp Ile Ile Tyr Asp Lys Ser Asp Ile Lys Ala Thr Val Thr Val Lys
        210                 215                 220

Asp Asn Asn His Gly Gln Leu Val Ser Thr Val Thr Tyr Glu Asn Ser
225                 230                 235                 240

Asp Gln Ile Phe Glu Asn Ile Leu Asn Pro Gly Lys Leu Ile Ala Pro
            245                 250                 255

Thr Thr Asp Ser Val Ile Thr Asp Asn Glu Val Ser Lys Glu Ala Met
            260                 265                 270

Ala Gly Lys Glu Lys Gly Asn Ile Glu Pro Pro Lys Glu Gln Ile Ala
        275                 280                 285

Asn Glu Glu Lys Asp Asn Ile Glu Ala Ser Glu Lys Gln Met Pro Ser
290                 295                 300

Ile Val Asn Asp Met Val Val Thr Pro Glu Lys
305                 310                 315
```

<210> SEQ ID NO 5
<211> LENGTH: 2036
<212> TYPE: DNA
<213> ORGANISM: Streptococcus suis

<400> SEQUENCE: 5

```
ctttgagaaa ggaaaaaagg ataatgaata ctaagaaatg agaacatcg ctcctaatac      60 caggaatagt attatttgga actgttgctc tagtgaataa tgtatcggca caagaagtaa    120
aaaataccat catcagcgca aaacaacctg atggggaca ggctacttca aaggcggtta    180
atgtcaaaat accagcagta gtacgactat ttggtcgtga gcttctagaa atgaattta     240 aatttgagct tagagaagcg aatggcgagg aactccctgt ccttgataca gctcaaaata    300
caaaagaggg tcaagttaga tttaaaaatc tatcattcga taagcctggc aaatactggt    360
atacaatttc agaagtaaaa gatgagcttg gtggtattga gtatgattcg aaatatattg    420
```

-continued

```
tagcaaaaat aactgtagaa gatcgaaacg ggcaattaca ggcaatgatc gaatttattg      480
ataatgacaa tgtctttaac aatttctata cacctgctcc agctgctgct agtctttcga      540 taaaaaagt cctcgaggga cgtaccttaa acaccggtga attcgaattt gttttaaaaa       600 atgaaaagg cgatgaaatc gaaaaggtaa gcaatcaagc agatggttct gtaaacttta      660
gtgccctaac atttacaaaa gagggaacct ataccctacac tgtttcagaa gttgatggtg    720
gacttggcga tattatctat gacaaatcag atattaaggc cactgttact gtgaaagata     780
acaatcacgg acaactagtc tcaacagtga cttatgaaaa tagcgatcaa atcttcgaga     840
atattttgaa tcctgggaag ttaatagcgc caaccacgga tagcgttatt actgataatg    900
aagtctctaa ggaagcaatg gccggtaaag agaagggaaa tatcgaaccc cctaaagagc     960
aaatagctaa tgaagagaag gataatattg aagcctctga aaacagatg ccaagcattg     1020 tgaacgacat ggtcgtaaca cctgaaaagc aaatgactaa taagagaac gataaggttg     1080 taatctctga aaacaaatg ccgagtgttg tgaacgaaaa tgccgtaaca cctgaaaagc     1140
aaatgactaa taagagaac gataatattg aaacctctga aaacagatg ccgagtgttg     1200 tgaacgaaaa tgccgtaaca cctgaaaagc aaatgactaa taagagaag gataatattg    1260 aaacctctga aaacagatg ccgagtgttg tgaacgaaaa tgccgtaaca cctgaaaagc     1320
aaatgactaa taagagaag gataatattg aaacctctga aaacaaatg ccaagcattg     1380 tgaacgacat ggtcgtaaca cctcaagaac aatggctaa taagagaac gataaggttg     1440 taatctctga aaacagatg ccaagcattg tgaacgacat ggtcgtaaca cctcaagaac    1500
aaatggctaa taagagaac gataaggttg taatctctga aaacagatg ccaagcattg    1560 tgaacgacat ggtcgtaaca cctcaagaac aaatggctaa taagagaac gataaggttg    1620 taatctctga aaacagatg ccaagcattg tgaacgacat ggtcgtaaca cctcaagaac    1680
aaatggctaa taagagaac gataaggttg aaacctctga aaacagatg cctgttaatg    1740 agaaggacaa tgccgtaaca cctgaaaagc aaatggctaa taagagaag gaaaatatcg    1800 aaacctctaa aaacagata cctgttaatg agaacaacca aaatggtaca gtcgaagaaa    1860
attcaaacac taaccaaca actgaaaaaa cagacaagca ggagacttca acatttaaaa    1920
ccgaaactgc taagcaaatc ttaccagtaa ctggtgagaa aggaagttta tggttattga    1980
caagtggtat tatcgggctt gcaattgcgt tatttcacg taaacgtaaa ttataa        2036
```

<210> SEQ ID NO 6
<211> LENGTH: 1742
<212> TYPE: DNA
<213> ORGANISM: Streptococcus suis

<400> SEQUENCE: 6

```
atgaatacta agaaatggag aacatcgctc ctaataccag gaatagtatt atttggaact      60
gttgctctag tgataatgt atcggcacaa gaagtaaaaa ataccatcat cagcgcaaaa      120
caacctgatg ggggacaggc tacttcaaag gcggttaatg tcaaaatacc agcagtagta     180
cgactatttg gtcgtgagct tctagaaaat gaatttaaat ttgagcttag agaagcgaat    240
ggcgaggaac tccctgtcct tgatacagct caaaatacaa agagggtca agttagattt     300 aaaaatctat cattcgataa gcctggcaaa tactggtata caatttcaga agtaaaagat    360
gagcttggtg gtattgagta tgattcgaaa tatattgtag caaaaataac tgtagaagat    420
cgaaacgggc aattacaggc aatgatcgaa tttattgata atgacaatgt ctttaacaat    480
ttctatacac ctgctccagc tgctgctagt ctttcgataa aaaaagtcct cgagggacgt    540
```

```
acctttaaaca ccggtgaatt cgaatttgtt ttaaaaaatg aaaaaggcga tgaaatcgaa    600
aaggtaagca atcaagcaga tggttctgta aactttagtg ccctaacatt tacaaaagag    660
ggaacctata cctacactgt ttcagaagtt gatggtggac ttggcgatat tatctatgac    720
aaatcagata ttaaggccac tgttactgtg aaagataaca atcacggaca actagtctca    780
acagtgactt atgaaaatag cgatcaaatc ttcgagaata ttttgaatcc tgggaagtta    840
atagcgccaa ccacggatag cgttattact gataatgaag tctctaagga agcaatggcc    900
ggtaaagaga agggaaatat cgaaccccct aaagagcaaa tagctaatga gagaaggat     960
aatattgaag cctctgaaaa acagatgccg agtgttgtga acgaaaatgc cgtaacacct   1020
gaaaagcaaa tgactaataa agagaaggat aatattgaaa cctctgaaaa acaaatgcca   1080
agcattgtga acgacatggt cgtaacacct caagaacaaa tggctaataa agagaacgat   1140
aaggttgtaa tctctgaaaa acagatgcca agcattgtga acgacatggt cgtaacacct   1200
caagaacaaa tggctaataa agagaacgat aaggttgtaa tctctgaaaa acagatgcca   1260
agcattgtga acgacatggt cgtaacacct cagaacaaat ggctaataaa gagaacgata   1320
aggttgtaat ctctgaaaaa cagatgccaa gcattgtgaa cgacatggtc gtaacacctc   1380
aagaacaaat ggctaataaa gagaacgata aggttgaaac ctctgaaaaa cagatgcctg   1440
ttaatgagaa ggacaatgcc gtaacacctg aaaagcaaat ggctaataaa gagaaggaaa   1500
atatcgaaac ctctaaaaaa cagatacctg ttaatgagaa caaccaaaat ggtacagtcg   1560
aagaaaattc aaacactaaa ccaacaactg aaaaaacaga caagcaggag acttcaacat   1620
ttaaaaccga aactgctaag caaatcttac cagtaactgg tgagaaagga agtttatggt   1680
tattgacaag tggtattatc gggcttgcaa ttgcgttatt tacacgtaaa cgtaaattat   1740
aa                                                                 1742

<210> SEQ ID NO 7
<211> LENGTH: 1563
<212> TYPE: DNA
<213> ORGANISM: Streptococcus suis

<400> SEQUENCE: 7
atgaatacta agaaatggag aacatcgctc ctaataccag gaatagtatt atttggaact    60
gttgctctag tgaataatgt atcggcacaa gaagtaaaaa ataccatcat cagcgcaaaa   120
caacctgatg ggggacaggc tacttcaaag gcggttaatg tcaaaatacc agcagtagta   180
cgactatttg gtcgtgagct tctagaaaat gaatttaaat ttgagcttag agaagcgaat   240
ggcgaggaac tccctgtcct tgatacagct caaaatacaa agagggtca gttagattt    300
aaaaatctat cattcgataa gcctggcaaa tactggtata caatttcaga agtaaaagat   360
gagcttggtg gtattgagta tgattcgaaa tatattgtag caaaaataac tgtagaagat   420
cgaaacgggc aattacaggc aatgatcgaa tttattgata atgacaatgt ctttaacaat   480
ttctatacac ctgctccagc tgctgctagt ctttcgataa aaaaagtcct cgagggacgt   540
acccttaaaca ccggtgaatt cgaatttgtt ttaaaaaatg aaaaaggcga tgaaatcgaa   600
aaggtaagca atcaagcaga tggttctgta aactttagtg ccctaacatt tacaaaagag   660
ggaacctata cctacactgt ttcagaagtt gatggtggac ttggcgatat tatctatgac   720
aaatcagata ttaaggccac tgttactgtg aaagataaca atcacggaca actagtctca   780
acagtgactt atgaaaatag cgatcaaatc ttcgagaata ttttgaatcc tgggaagtta   840
atagcgccaa ccacggatag cgttattact gataatgaag tctctaagga agcaatggcc   900
```

```
ggtaaagaga agggaaatat cgaacccct aaagagcaaa tagctaatga agagaaggat      960
aatattgaag cctctgaaaa acagatgcca agcattgtga acgacatggt cgtaacacct     1020
gaaaagcaaa tgactaataa agagaacgat aaggttgtaa tctctgaaaa acaaatgccg     1080
agtgttgtga acgaaaatgc cgtaacacct gaaaagcaaa tgactaataa agagaacgat     1140
aatattgaaa cctctgaaaa acagatgccg agtgttgtga acgaaaatgc cgtaacacct     1200
gaaaagcaaa tgactaataa agagaaggat aatattgaaa cctctgaaaa acagatgccg     1260
agtgttgtga acgaaaatgc cgtaacacct gaaaagcaaa tgactaataa agagaaggat     1320
aatattgaaa cctctgaaaa acaaatacct gttaatgaga caaccaaaa tggtacagtc      1380 gaagaaaatt caaacactaa accaacaact gaaaaacag acaagcagga gacttcaaca      1440
tttaaaaccg aaactgctaa gcaaatctta ccagtaactg gtgagaaagg aagtttatgg     1500
ttattgacaa gtggtattat cgggcttgca attgcgttat ttacacgtaa acgtaaatta     1560
taa                                                                   1563

<210> SEQ ID NO 8
<211> LENGTH: 945
<212> TYPE: DNA
<213> ORGANISM: Streptococcus suis

<400> SEQUENCE: 8
tcggcacaag aagtaaaaaa taccatcatc agcgcaaaac aacctgatgg gggacaggct       60
acttcaaagg cggttaatgt caaaatacca gcagtagtac gactatttgg tcgtgagctt      120
ctagaaaatg aatttaaatt tgagcttaga gaagcgaatg cgaggaact ccctgtcctt       180 gatacagctc aaaatacaaa agagggtcaa gttagattta aaaatctatc attcgataag      240
cctggcaaat actggtatac aatttcagaa gtaaagatg agcttggtgg tattgagtat       300
gattcgaaat atattgtagc aaaaataact gtagaagatc gaaacgggca attacaggca      360
atgatcgaat ttattgataa tgacaatgtc tttaacaatt tctatacacc tgctccagct      420
gctgctagtc tttcgataaa aaaagtcctc gagggacgta ccttaaacac cggtgaattc      480
gaatttgttt taaaaatga aaaaggcgat gaaatcgaaa aggtaagcaa tcaagcagat      540
ggttctgtaa actttagtgc cctaacattt acaaagagg gaacctatac ctacactgtt       600
tcagaagttg atggtggact tggcgatatt atctatgaca aatcagatat taaggccact      660
gttactgtga aagataacaa tcacggacaa ctagtctcaa cagtgactta tgaaaatagc      720
gatcaaatct tcgagaatat tttgaatcct gggaagttaa tagcgccaac cacggatagc      780
gttattactg ataatgaagt ctctaaggaa gcaatggccg gtaaagagaa gggaaatatc      840 gaaccccta aagagcaaat agctaatgaa gagaaggata atattgaagc ctctgaaaaa       900
cagatgccaa gcattgtgaa cgacatggtc gtaacacctg aaaag                      945

<210> SEQ ID NO 9
<211> LENGTH: 30
<212> TYPE: PRT
<213> ORGANISM: Streptococcus suis
<220> FEATURE:
<221> NAME/KEY: SITE
<222> LOCATION: (1)..(1)
<223> OTHER INFORMATION: Xaa is Val, Thr or Ile
<220> FEATURE:
<221> NAME/KEY: SITE
<222> LOCATION: (3)..(3)
<223> OTHER INFORMATION: Xaa is Lys or Glu
<220> FEATURE:
<221> NAME/KEY: SITE
<222> LOCATION: (4)..(4)
```

-continued

```
<223> OTHER INFORMATION: Xaa is Lys or Glu
<220> FEATURE:
<221> NAME/KEY: SITE
<222> LOCATION: (5)..(5)
<223> OTHER INFORMATION: Xaa is Ala or Gln
<220> FEATURE:
<221> NAME/KEY: SITE
<222> LOCATION: (7)..(7)
<223> OTHER INFORMATION: Xaa is Thr or Pro
<220> FEATURE:
<221> NAME/KEY: SITE
<222> LOCATION: (8)..(8)
<223> OTHER INFORMATION: Xaa is Gly, Ser or Val
<220> FEATURE:
<221> NAME/KEY: SITE
<222> LOCATION: (9)..(9)
<223> OTHER INFORMATION: Xaa is Lys, Val, Ile or Asn
<220> FEATURE:
<221> NAME/KEY: SITE
<222> LOCATION: (10)..(10)
<223> OTHER INFORMATION: Xaa is Glu or Val
<220> FEATURE:
<221> NAME/KEY: SITE
<222> LOCATION: (11)..(11)
<223> OTHER INFORMATION: Xaa is Lys or Asn
<220> FEATURE:
<221> NAME/KEY: SITE
<222> LOCATION: (12)..(12)
<223> OTHER INFORMATION: Xaa is Gly, Glu or Asp
<220> FEATURE:
<221> NAME/KEY: SITE
<222> LOCATION: (13)..(13)
<223> OTHER INFORMATION: Xaa is Asn or Met
<220> FEATURE:
<221> NAME/KEY: SITE
<222> LOCATION: (14)..(14)
<223> OTHER INFORMATION: Xaa is Ile, Ala or Val
<220> FEATURE:
<221> NAME/KEY: SITE
<222> LOCATION: (15)..(15)
<223> OTHER INFORMATION: Xaa is Glu or Val
<220> FEATURE:
<221> NAME/KEY: SITE
<222> LOCATION: (16)..(16)
<223> OTHER INFORMATION: Xaa is Pro or Thr
<220> FEATURE:
<221> NAME/KEY: SITE
<222> LOCATION: (18)..(18)
<223> OTHER INFORMATION: Xaa is Glu or Gln
<220> FEATURE:
<221> NAME/KEY: SITE
<222> LOCATION: (19)..(19)
<223> OTHER INFORMATION: Xaa is Lys or Glu
<220> FEATURE:
<221> NAME/KEY: SITE
<222> LOCATION: (22)..(22)
<223> OTHER INFORMATION: Xaa is Thr or Ala
<220> FEATURE:
<221> NAME/KEY: SITE
<222> LOCATION: (26)..(26)
<223> OTHER INFORMATION: Xaa is Lys or Asn
<220> FEATURE:
<221> NAME/KEY: SITE
<222> LOCATION: (27)..(27)
<223> OTHER INFORMATION: Xaa is Asp or Glu
<220> FEATURE:
<221> NAME/KEY: SITE
<222> LOCATION: (28)..(28)
<223> OTHER INFORMATION: Xaa is Asn or Lys
<220> FEATURE:
<221> NAME/KEY: SITE
<222> LOCATION: (29)..(29)
<223> OTHER INFORMATION: Xaa is Ile or Val
<220> FEATURE:
<221> NAME/KEY: SITE
<222> LOCATION: (30)..(30)
<223> OTHER INFORMATION: Xaa is Glu or Val

<400> SEQUENCE: 9
```

```
Xaa Ser Xaa Xaa Xaa Met Xaa Xaa Xaa Xaa Xaa Xaa Xaa Xaa Xaa
 1               5                  10                  15

Pro Xaa Xaa Gln Met Xaa Asn Lys Glu Xaa Xaa Xaa Xaa Xaa
         20                  25                  30
```

<210> SEQ ID NO 10
<211> LENGTH: 5
<212> TYPE: PRT
<213> ORGANISM: Streptococcus suis

<400> SEQUENCE: 10

```
Lys Pro Val Thr Gly
 1               5
```

<210> SEQ ID NO 11
<211> LENGTH: 386
<212> TYPE: PRT
<213> ORGANISM: Streptococcus suis

<400> SEQUENCE: 11

```
Met Lys Arg Lys Arg Thr Asn Lys Pro Gln His Met Arg Lys Arg
 1               5                  10                  15

Lys Thr Pro Ile Met Lys Asn Asn Lys Lys Met Leu Tyr Thr Ser Ser
                 20                  25                  30

Leu Ala Leu Ser Leu Phe Ser Thr Gly Met Ile Ser Thr Asn Val Leu
                 35                  40                  45

Ala Ile Glu Trp Ala Pro Arg Thr Val Ser Glu Ile Ser Pro Glu Ile
         50                  55                  60

Val Gln Glu Glu Gly Arg Met Thr Tyr Thr Val Gln Tyr Gly Asp Thr
 65              70                  75                  80

Leu Ser Ala Ile Ala Ser Ala Met Asn Ile Asp Met Asp Leu Leu Ala
                 85                  90                  95

Lys Ile Asn Gln Ile Ala Asp Val Asn Leu Ile Phe Pro Asp Thr Val
                100                 105                 110

Leu Thr Thr Thr Val Asp Gln Asn Asn Gln Val Thr Gln Val Glu Ile
                115                 120                 125

Glu Ala Pro Val Gln Gly Asn Thr Asn Glu Thr Val Gln Ala Thr Val
                130                 135                 140

Asp Leu Thr Thr Asn Gln Val Thr Val Glu Asp Thr Val Val Pro Leu
145                 150                 155                 160

Asp Gln Ile Ser Ser Val Thr Asp Ser Ala Pro Val Glu Glu Val Val
                165                 170                 175

Glu Gln Pro Val Ala Glu Ala Pro Val Glu Val Val Glu Gln Pro
                180                 185                 190

Val Val Glu Ala Pro Val Glu Val Val Glu Gln Pro Val Val Glu
                195                 200                 205

Ala Pro Val Glu Glu Val Ala Glu Gln Pro Val Val Glu Ala Pro Val
                210                 215                 220

Glu Glu Val Val Glu Gln Pro Val Val Glu Ala Pro Val Glu Val
225                 230                 235                 240

Ala Glu Gln Pro Val Val Glu Ala Pro Val Glu Gln Pro Val Val Glu
                245                 250                 255

Thr Pro Gln Val Thr Ala Leu Ser Thr Thr Thr Ser Thr Ser Ala
                260                 265                 270

Tyr Asp Val Gly Leu Gln Pro Gln Val Ala Ala Phe Arg Ala Glu Val
                275                 280                 285

Ala Asn Ala Phe Gly Ile Thr Ser Phe Ser Gly Tyr Arg Pro Gly Asp
```

```
                290                   295                   300
Ser Gly Asp His Gly Lys Gly Leu Ala Ile Asp Phe Met Val Pro Glu
305                   310                   315                   320

Ser Ser Ala Leu Gly Asp Gln Val Ala Ala Tyr Ala Val Ala Asn Leu
                325                   330                   335

Ala Ser Lys Asn Ile Asn Tyr Ile Ile Trp Lys Gln Arg Phe Tyr Ala
                340                   345                   350

Pro Tyr Asp Ser Ile Tyr Gly Pro Ala Tyr Thr Trp Asn Leu Met Pro
                355                   360                   365

Asp Arg Gly Ser Ile Thr Glu Asn His Tyr Asp His Val His Val Ser
    370                   375                   380

Phe Asn
385
```

<210> SEQ ID NO 12
<211> LENGTH: 1161
<212> TYPE: DNA
<213> ORGANISM: Streptococcus suis

<400> SEQUENCE: 12

```
atgaaacgta agagaacaaa taaccacaa catatgcgtc gcaagagaaa aacacctatc      60
atgaaaaaca ataagaagat gttatacaca tcttcattgg ctctttccct ctttagtaca     120
gggatgattt cgacaaatgt tttagccatc gaatgggctc cacgtactgt ttctgaaatt     180
agcccagaaa ttgtacaaga agaaggaagg atgacctata ctgttcagta tggagatacc     240
ttatctgcca tcgcctcagc tatgaatatt gatatggact tgctggcgaa aataaatcaa     300
attgcagatg tcaacttgat tttccctgat acggtactga cgacgactgt tgaccaaaac     360
aatcaagtga ctcaggttga gattgaagct cctgttcagg aaacacaaa tgagaccgtt      420 caggcaactg ttgacctaac aaccaatcaa gtaacggttg aggatacggt tgttcccttg     480
gatcaaattt catcagttac cgactcagcg cccgtagagg aagttgtaga acagcctgta     540
gcagaagcac ctgtagagga agttgtagaa caacctgtag tagaagcgcc cgtagaggaa     600
gttgtagaac agcctgtagt agaagcacct gtagaggaag ttgcagaaca cctgtggttg     660
aggcaacctg tagaggaagt ggtggagcaa cctgtggttg aggcacctgt agaggaagtt     720
gcagaacaac tgtagtaga agcacctgta gaacagcctg tagttgaaac tccacaagtg     780
acagccctat caactactac aacaagtaca agtgcttatg atgtcggttt gcaacctcag     840
gtagcagcct tccgcgcaga agtagctaat gccttcggta ttacttcttt ctcaggttac     900
cgtcctggtg attctggcga ccatggtaag ggattggcaa ttgactttat ggtgcctgag     960
agctcagctc taggagatca agtggcagct tatgcagttg caaacttagc ttctaaaaat    1020
atcaactaca tcatttggaa acagcgcttc tatkcgccgt atgacagtat ctatggtcca    1080
gcctatacat ggaatctgat gccagaccgt ggtagcatta cagaaaacca ctacgatcat    1140
gtgcatgtat cttttaatta g                                             1161
```

<210> SEQ ID NO 13
<211> LENGTH: 38
<212> TYPE: DNA
<213> ORGANISM: Artificial Sequence
<220> FEATURE:
<223> OTHER INFORMATION: Oligonucleotide primer

<400> SEQUENCE: 13

```
atggatccat tgaaggccgc tcggcacaag aagtaaaa                              38
```

<210> SEQ ID NO 14
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 14
ccaagtcgac ttataattta cgtttacgtg ta 32

<210> SEQ ID NO 15
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 15
tttaaaagaa cggttgaagg c 21

<210> SEQ ID NO 16
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 16
gcataagctg ccacttgatc t 21

<210> SEQ ID NO 17
<211> LENGTH: 319
<212> TYPE: PRT
<213> ORGANISM: Xanthomonas Oryzae

<400> SEQUENCE: 17

```
Lys Gln Ala Leu Glu Thr Val Gln Arg Leu Leu Pro Val Leu Cys Gln
1               5                   10                  15

Asp His Gly Leu Thr Pro Asp Gln Val Val Ala Ile Ala Ser His Asp
            20                  25                  30

Gly Gly Lys Gln Ala Leu Glu Thr Val Gln Arg Leu Leu Pro Val Leu
        35                  40                  45

Cys Gln Asp His Gly Leu Thr Pro Asp Gln Val Val Ala Ile Ala Ser
    50                  55                  60

Asn Ser Gly Gly Lys Gln Ala Leu Glu Thr Val Gln Arg Leu Leu Pro
65                  70                  75                  80

Val Leu Cys Gln Asp His Gly Leu Thr Pro Asp Gln Val Val Ala Ile
                85                  90                  95

Ala Ser Asn Asn Gly Gly Lys Gln Ala Leu Glu Thr Val Gln Arg Leu
            100                 105                 110

Leu Pro Val Leu Phe Gln Glu His Gly Leu Thr Pro Asp Gln Val Val
        115                 120                 125

Ala Ile Ala Ser Asn Ser Gly Gly Lys Gln Ala Leu Glu Thr Val Gln
    130                 135                 140

Arg Leu Leu Pro Val Leu Cys Gln Asp His Gly Leu Thr Pro Asp Gln
145                 150                 155                 160

Val Val Ala Ile Ala Asn Asn Asn Gly Gly Lys Gln Ala Leu Glu Thr
                165                 170                 175

Val Gln Arg Leu Leu Pro Val Leu Cys Gln Asp His Gly Leu Thr Pro
            180                 185                 190
```

```
Ala Gln Val Val Ala Ile Ala Ser Asn Ile Gly Gly Lys Gln Ala Leu
            195                 200                 205

Glu Thr Val Gln Arg Leu Leu Pro Val Leu Cys Gln Asp His Gly Leu
    210                 215                 220

Thr Leu Asp Gln Val Val Ala Ile Ala Ser Asn Gly Gly Ser Lys Gln
225                 230                 235                 240

Ala Leu Glu Thr Val Gln Arg Leu Leu Pro Val Leu Cys Gln Asp His
                245                 250                 255

Gly Leu Thr Pro Asp Gln Val Val Ala Ile Ala Asn Asn Asn Gly Gly
            260                 265                 270

Lys Gln Ala Leu Glu Thr Val Gln Arg Leu Leu Pro Val Leu Cys Gln
        275                 280                 285

Asp His Gly Leu Thr Pro Asp Gln Val Val Ala Ile Ala Ser Asn Ile
290                 295                 300

Gly Gly Lys Gln Ala Leu Glu Thr Val Gln Arg Leu Leu Pro Val
305                 310                 315

<210> SEQ ID NO 18
<211> LENGTH: 283
<212> TYPE: PRT
<213> ORGANISM: Streptococcus suis

<400> SEQUENCE: 18

Lys Asp Asn Ile Glu Ala Ser Glu Lys Gln Met Pro Ser Ile Val Asn
1               5                   10                  15

Asp Met Val Val Thr Pro Glu Lys Gln Met Thr Asn Lys Glu Asn Asp
            20                  25                  30

Lys Val Val Ile Ser Glu Lys Gln Met Pro Ser Val Val Asn Glu Asn
        35                  40                  45

Ala Val Thr Pro Glu Lys Gln Met Thr Asn Lys Glu Asn Asp Asn Ile
    50                  55                  60

Glu Thr Ser Glu Lys Gln Met Pro Ser Val Val Asn Glu Asn Ala Val
65                  70                  75                  80

Thr Pro Glu Lys Gln Met Thr Asn Lys Glu Lys Asp Asn Ile Glu Thr
                85                  90                  95

Ser Glu Lys Gln Met Pro Ser Val Val Asn Glu Asn Ala Val Thr Pro
            100                 105                 110

Glu Lys Gln Met Thr Asn Lys Glu Lys Asp Asn Ile Glu Thr Ser Glu
        115                 120                 125

Lys Gln Met Pro Ser Ile Val Asn Asp Met Val Val Thr Pro Gln Glu
130                 135                 140

Gln Met Ala Asn Lys Glu Asn Asp Lys Val Val Ile Ser Glu Lys Gln
145                 150                 155                 160

Met Pro Ser Ile Val Asn Asp Met Val Val Thr Pro Gln Glu Gln Met
                165                 170                 175

Ala Asn Lys Glu Asn Asp Lys Val Val Ile Ser Glu Lys Gln Met Pro
            180                 185                 190

Ser Ile Val Asn Asp Met Val Val Thr Pro Gln Glu Gln Met Ala Asn
        195                 200                 205

Lys Glu Asn Asp Lys Val Val Ile Ser Glu Lys Gln Met Pro Ser Ile
210                 215                 220

Val Asn Asp Met Val Val Thr Pro Gln Glu Gln Met Ala Asn Lys Glu
225                 230                 235                 240

Asn Asp Lys Val Glu Thr Ser Glu Lys Gln Met Pro Val Asn Glu Lys
                245                 250                 255
```

```
Asp Asn Ala Val Thr Pro Glu Lys Gln Met Ala Asn Lys Glu Lys Glu
            260                 265                 270
Asn Ile Glu Thr Ser Lys Lys Gln Ile Pro Val
            275                 280
```